United States Patent
Griffith et al.

(10) Patent No.: US 12,084,685 B2
(45) Date of Patent: Sep. 10, 2024

(54) SYNTHETIC HYDROGELS FOR ORGANOGENESIS

(71) Applicant: Massachusetts Institute of Technology, Cambridge, MA (US)

(72) Inventors: Linda G. Griffith, Cambridge, MA (US); Victor Hernandez-Gordillo, Cambridge, MA (US)

(73) Assignee: MASSAACHUSETTS INSTITUTE OF TECHNOLOGY, Cambridge, MA (US)

( * ) Notice: Subject to any disclaimer, the term of this patent is extended or adjusted under 35 U.S.C. 154(b) by 682 days.

(21) Appl. No.: 16/942,580

(22) Filed: Jul. 29, 2020

(65) Prior Publication Data
US 2021/0087534 A1  Mar. 25, 2021

Related U.S. Application Data

(60) Provisional application No. 62/879,920, filed on Jul. 29, 2019.

(51) Int. Cl.
C12N 5/071 (2010.01)
(52) U.S. Cl.
CPC ......... *C12N 5/0682* (2013.01); *C12N 5/0679* (2013.01); *C12N 2533/40* (2013.01);
(Continued)
(58) Field of Classification Search
CPC ............ C12N 2533/40; C12N 2533/50; C12N 2533/52; C12N 2533/54
See application file for complete search history.

(56) References Cited

U.S. PATENT DOCUMENTS

| | | |
|---|---|---|
| 2015/0352156 A1 | 12/2015 | Jha et al. |
| 2018/0010091 A1 | 1/2018 | Griffith |

(Continued)

FOREIGN PATENT DOCUMENTS

| | | |
|---|---|---|
| EP | 2946011 | 11/2015 |
| WO | 2016115410 | 7/2016 |

(Continued)

OTHER PUBLICATIONS

Cook et al., Local remodeling of synthetic extracellular matrix microenvironments by co-cultured endometrial epithelial and stromal cells enables long-term dynamic physiological function. Integrative Biology, vol. 9, No. 4 (Apr. 2017) pp. 271-289 (Year: 2017).*

(Continued)

*Primary Examiner* — Kara D Johnson
(74) *Attorney, Agent, or Firm* — PABST PATENT GROUP LLP

(57) ABSTRACT

Synthetic hydrogels for organogenesis support organogenesis from mammalian cells, including human cells. The synthetic hydrogels typically include a network of cross-linked branched biodegradable polymers. A portion of the branches of the branched biodegradable polymers are linked to binders which are generally synthetic peptides for cell and extracellular matrix attachment. The hydrogels may include an inhibitor of apoptosis. The synthetic hydrogels with the synthetic binders typically do not interfere with cellular, proteomic, genetic, and/or transcriptome analyses of organoids formed in the hydrogel. The synthetic hydrogels may be subject to on-demand dissolution to provide intact organoids substantially free of hydrogel polymers. Also provided are methods of making the synthetic hydrogels and methods of using the synthetic hydrogels for organogenesis.

30 Claims, 16 Drawing Sheets
Specification includes a Sequence Listing.

(52) U.S. Cl.
CPC ...... *C12N 2533/50* (2013.01); *C12N 2533/52* (2013.01); *C12N 2533/54* (2013.01)

(56) References Cited

U.S. PATENT DOCUMENTS

| | | |
|---|---|---|
| 2018/0010097 A1 | 1/2018 | Wälchli |
| 2019/0117782 A1 | 4/2019 | Schaffer et al. |
| 2019/0367869 A1 | 12/2019 | Angres et al. |

FOREIGN PATENT DOCUMENTS

| | | |
|---|---|---|
| WO | 2017036533 | 3/2017 |
| WO | 2018165565 | 9/2018 |

OTHER PUBLICATIONS

Kim et al., Characterization of the crosslinking kinetics of multi-arm poly(ethylene glycol) hydrogels formed via Michael-type addition. Soft Matter, vol. 12 (2016) 2076 (Year: 2016).*
Ovadia et al., Designing well-defined photopolymerized synthetic matrices for three-dimensional culture and differentiation of induced pluripotent stem cells. Biomaterials Science, vol. 6 (2018) 1358 (Year: 2018).*
Pakzad et al., Presence of a Rock inhibitor in extracellular matrix supports more undifferentiated growth of feeder-free human embryonic and induced pluripotent stem cells upon passaging. Stem Cell Reviews and Reports, vol. 6 (2010) pp. 96-107 (Year: 2010).*
Zhang, Cuiying. (May 2019) Organ-on-a-chip design for the small intestine modeling [Master's Thesis, Northeastern University]. Boston, Massachusetts : Northeastern University (Year: 2019).*
Ahmad, et al., "Optimization of 3-D organotypic primary colonic cultures for organ-on-chip applications", J. Biol. Eng., 8:9 (2014).
Almeqdadi, "Gut organoids: Mini-tissues in culture to study intestinal physiology and disease", Am. J. Physiol.—Cell Physiol., 317 C405-C419 (2019).
Arkenberg, et al., "Dynamic control of hydrogel crosslinking via sortase-mediated reversible transpeptidation", Acta Biomater., 83: 83-95 (2019).
Arkenberg, et al., "Othogonal enzymatic reactions for rapid crosslinking and dynamic tuning of PEG-peptide hydrogels", Biomater. Sci., 5: 2231-2240 (2017).
Attwood, et al., "Adhesive ligand tether length affects the size and length of focal adhesions and influences cell spreading and attachment", Sci. Rep., 6:34334, 11 pages (2016).
Aumailley, et al., "A simplified laminin nomenclature", Matrix Biology, 24(5):326-332 (2005).
Ayyaz, et al., "Single-cell transcriptomes of the regenerating intestine reveal a revival stem cell", Nature, 569:121-125 (2019).
Bankaitis, et al., "Reserve Stem Cells in Intestinal Homeostasis and Injury", Gastroenterology, 155(5):1348-1361 (2018).
Beaulieu, "Integrin α6β4 in colorectal cancer", World J. Gastrointest. Pathophysiol., 1(1):3-11 (2010).
Béliard, et al., Localization of laminin, fibronectin, E-cadherin, and integrins in endometrium and endometriosis, Fertil. Steril., 67: 266-272 (1997).
Belkin, et al., "Integrins as receptors for laminins", Microsc. Res. Tech., 51(3):280-301 (2000).
Benoit, et al., "Integrin α8β1 confers anoikis susceptibility to human intestinal epithelial crypt cells", Biochem. Biophys. Res. Commun., 399(3):434-439 (2010).
Benoit, et al., "RGD-Dependent Epithelial Cell-Matrix Interactions in the Human Intestinal Crypt", J. Signal Transduct., 2012:248759, 10 pages (2012).
Beumer, et al., "Regulation and plasticity of intestinal stem cells during homeostasis and regeneration", Development, 143(20):3639-3649 (2016).
Bischof, et al., Localization of alpha 2, alpha 5 and alpha 6 integrin subunits in human endometrium, decidua and trophoblast., Eur. J. Obstet. Gynecol. Reprod. Biol., 51(3):217-26 (1993).

Boj, et al., "Forskolin-induced swelling in intestinal organoids: An in vitro assay for assessing drug response in cystic fibrosis patients", J. Vis. Exp., (120):55159 (2017).
Boretto, et al., "Development of organoids from mouse and human endometrium showing endometrial epithelium physiology and long-term expandability", Development, 144(10):1775-1786 (2017).
Boretto, et al., "Patient-derived organoids from endometrial disease capture clinical heterogeneity and are amenable to drug screening", Nat. Cell Biol., 21(8):1041-1051 (2019).
Broguiere, et al., "Growth of Epithelial Organoids in a Defined Hydrogel", Adv. Mater., 30: 1801621 (2018).
Brown, et al., "Engineering PEG-based hydrogels to foster efficient endothelial network formation in free-swelling and confined microenvironments", Biomaterials, 243:119921 (2020).
Cambria, et al., "Covalent Modification of Synthetic Hydrogels with Bioactive Proteins via Sortase-Mediated Ligation", Biomacromolecules, 16(8):2316-26 (2015).
Capeling, et al., "Nonadhesive Alginate Hydrogels Support Growth of Pluripotent Stem Cell-Derived Intestinal Organoids", Stem Cell Reports, 12(2):381-394 (2019).
Carafoli, et al., "Crystal Structures of the Network-Forming Short-Arm Tips of the Laminin b1 and c1 Chains", PLoS ONE, 7(7):e42473, 9 pages (2012).
Casillas-Ituarte, et al., "Amino acid polymorphisms in the fibronectin-binding repeats of fibronectin-binding protein A affect bond strength and fibronectin conformation", J. Biol. Chem., 292(21):8797-8810 (2017).
Chan, et al., "Covalent Attachment of Proteins to Solid Supports and Surfaces via Sortase-Mediated Ligation", PLoS ONE, 2(11):e1164, 5 pages (2007).
Chen, et al., "A general strategy for the evolution of bond-forming enzymes using yeast display", PNAS, 108(28):11399-11404 (2011).
Cima, et al., "Network Structures of Radiation-Cross-Linked Star Polymer Gels", Macromolecules, 28:6787-6794 (1995).
Co, et al., "Controlling Epithelial Polarity: A Human Enteroid Model for Host-Pathogen Interactions", Cell Rep., 26(9):2509-2520. e4 (2019).
Cook, et al., "Local remodeling of synthetic extracellular matrix microenvironments by co-cultured endometrial epithelial and stromal cells enables long-term dynamic physiological function", Integrative Biology, 9(4):271-289 (2017).
Creff, et al., "Fabrication of 3D scaffolds reproducing intestinal epithelium topography by high-resolution 3D stereolithography", Biomaterials, 221:119404, 13 pages (2019).
Cruz-Acuña, et al., "PEG-4MAL hydrogels for human organoid generation, culture, and in vivo delivery", Nat Protoc., 13(9):2102-2119 (2018).
Cruz-Acuña, et al., "Synthetic hydrogels for human intestinal organoid generation and colonic wound repair", Nat. Cell Biol., 19(11):1326-1335 (2017a).
Cruz-Acuña, et al., "Synthetic hydrogels mimicking basement membrane matrices to promote cell-matrix interactions", Matrix Biol., 57-58:324-333 (2017b).
Darling, et al., "Controlling the kinetics of thiol-maleimide Michael-type addition gelation kinetics for the generation of homogenous poly(ethylene glycol) hydrogels", Biomaterials, 101:199-206 (2016).
Dasgupta, et al., "Physics of lumen growth", Proc. Natl. Acad. Sci., 115(21):E4751-E4757 (2018).
Date, et al., "Mini-Gut Organoids: Reconstitution of the Stem Cell Niche", Annu. Rev. Cell Dev. Biol., 313221:1-32 (2015).
Devaud, et al., "Label-Free Quantification Proteomics for the Identification of Mesenchymal Stromal Cell Matrisome Inside 3D Poly(Ethylene Glycol) Hydrogels", Adv. Healthc. Mater., 7:1800534 (2018).
DiMarco, et al., "Engineering of three-dimensional microenvironments to promote contractile behavior in primary intestinal organoids", Integr. Biol. (United Kingdom), 6:127-142 (2014).
Dorr, et al., "Reprogramming the specificity of sortase enzymes", Proc. Natl. Acad. Sci., 111(37): 13343-13348 (2014).
Drost, et al., "Organoids in cancer research", Nat. Rev. Cancer, 18(7): 407-418 (2018).

(56) References Cited

OTHER PUBLICATIONS

Ebara, et al., "The effect of extensible PEG tethers on shielding between grafted thermo-responsive polymer chains and integrin-RGD binding", Biomaterials, 29:3650-3655 (2008).
Ebnet, et al., "Regulation of cell polarity by cell adhesion receptors", Semin. Cell Dev. Biol., 81: 2-12 (2018).
Edington, et al., "Interconnected Microphysiological Systems for Quantitative Biology and Pharmacology Studies", Scientific Reports, 8(1):4530, 18 pages (2018).
Ekblom, et al., "Laminin isoforms and epithelial development", Ann. N. Y. Acad. Sci., New York Academy of Sciences, 1998:194-211 (1998).
Feng, et al., "The synergy peptide PHSRN and the adhesion peptide RGD mediate cell adhesion through a common mechanism", Biochemistry, 43:15811-15821 (2004).
Fonseca, et al., "Engineering proteolytically-degradable artificial extracellular matrices", Prog. in Poly. Sci., 39(12):2010-29 (2014).
Foulke-Abel, et al., "Human Enteroids as a Model of Upper Small Intestinal Ion Transport Physiology and Pathophysiology", Gastroenterology, 150(3): 638-649.e8 (2016).
Fujii, et al., "Human Intestinal Organoids Maintain Self-Renewal Capacity and Cellular Diversity in Niche-Inspired Culture Condition", Cell Stem Cell, 23:787-793.e6 (2018).
Gao, et al., "Fibronectin-binding peptides. I. Isolation and characterization of two unique fibronectin-binding peptides from gelatin", Eur. J. Pharm. Biopharm., 45:275-284 (1998).
Gjorevski, et al., "Lutolf, Designer matrices for intestinal stem cell and organoid culture", Nat. Publ. Gr., 539:560-564 (2016).
Hernandez-Gordillo, et al., "Engineering the intestinal basement membrane microenvironment using PEG-based hydrogels", Frontiers, Bioeng. Biotechnol. Conference Abstract: 10th World Biomaterials Congress, 2 pages (2016).
Hernandez-Gordillo, et al., "Mimicking the extracellular matrix with functionalized, metal-assembled collagen peptide scaffolds", Biomaterials, 35(26):7363-7373 (2014).
Houseman, et al., "The microenvironment of immobilized Arg-Gly-Asp peptides is an important determinant of cell adhesion", Biomaterials, 22(9):943-955 (2001).
Huettner, et al., "Discovering Cell-Adhesion Peptides in Tissue Engineering: Beyond RGD", Trends Biotechnol., 36(4):372-383 (2018).
Hughes, et al., "Mass Spectrometry-based Proteomic Analysis of the Matrix Microenvironment in Pluripotent Stem Cell Culture", Mol. Cell. Proteomics, 11(12): 1924-1936 (2012).
Hughes, et al., "Matrigel: a complex protein mixture required for optimal growth of cell culture", Proteomics, 10:1886-1890 (2010).
International Search Report for PCT/US2020/044067 dated Nov. 19, 2020.
Jansen, et al., "Control of thiol-maleimide reaction kinetics in PEG hydrogel networks", Acta Biomater., 70: 120-128 (2018).
Johnson, et al., "Identification of a structural site on acetylcholinesterase that promotes neurite outgrowth and binds laminin-1 and collagen IV", Biochem. Biophys. Res. Commun., 319:448-455 (2004).
Kadajji, et al., "Water Soluble Polymers for Pharmaceutical Applications", Polymers, 3:1972-2009 (2011).
Kao, et al., "Fibronectin modulates macrophage adhesion and FBGC formation: The role of RGD, PHSRN, and PRRARV domains", J. Biomed. Mater. Res., 55(1): 79-88 (2001).
Kasendra, et al., "Development of a primary human Small Intestine-on-a-Chip using biopsy-derived organoids", Sci. Rep., 8(1):2871 (2018).
Kassis, et al., "OrgaQuant: Human Intestinal Organoid Localization and Quantification Using Deep Convolutional Neural Networks", Sci. Rep., 9(1):12479 (2019).
Kaushik, et al., "Concise Review: Current Status of Three-Dimensional Organoids as Preclinical Models", Stem Cells, 36(9):1329-1340 (2018).
Kim, et al., "Characterization of the crosslinking kinetics of multi-arm poly(ethylene glycol) hydrogels formed via Michael-type addition", Soft Matter., 12(7):2076-2085 (2016).

Knight, et al., "The collagen-binding a-domains of integrins $\alpha1/\beta1$ and $\alpha2/\beta1$ recognize the same specific amino acid sequence, GFOGER, in native (triple-helical) collagens", J. Biol. Chem., 275(1):35-40 (2000).
Koo, et al., "Co-regulation of cell adhesion by nanoscale RGD organization and mechanical stimulus", J. Cell Sci., 115(Pt 7):1423-1433 (2002).
Koppes, et al., "Complex, multi-scale small intestinal topography replicated in cellular growth substrates fabricated via chemical vapor deposition of Parylene C", Biofabrication, 8(3):035011, 23 pages (2016).
Kraiczy, et al., "DNA methylation defines regional identity of human intestinal epithelial organoids and undergoes dynamic changes during development", Gut, 68(1):49-61 (2019).
Kratochvil, et al., "Engineered materials for organoid systems", Nat. Rev. Mater., 4(9):606-622 (2019).
Kuhlman, et al., "Interplay between PEO tether length and ligand spacing governs cell spreading on RGD-modified PMMA-g-PEO comb copolymers", Biomacromolecules, 8(10):3206-3213 (2007).
Kyburz, et al., "Synthetic Mimics of the Extracellular Matrix: How Simple is Complex enough?", Ann. Biomed. Eng., 43(3):489-500 (2015).
Lancaster, et al., "Organogenesisin a dish: Modeling development and disease using organoid technologies", Science, 345(6194): 1247125 (2014).
Lee, et al., "Collagen mimetic peptide-conjugated photopolymerizable PEG hydrogel", Biomaterials, 27(30):5268-5276 (2006).
Lessey, et al., "Integrin adhesion molecules in the human endometrium. Correlation with the normal and abnormal menstrual cycle", J. Clin. Invest., 90(1):188-195 (1992).
Lin, et al., "Controlling affinity binding with peptide-functionalized poly(ethylene glycol) hydrogels", Adv. Funct. Mater., 19:2325-2331 (2009).
Liu, et al., "Irreversible Sortase A-Mediated Ligation Driven by Diketopiperazine Formation", J. Org. Chem., 79(2):487-492 (2014).
Lopina, et al., "Hepatocyte culture on carbohydrate-modified star polyethylene oxide hydrogels", Biomaterials, 17:559-569 (1996).
Lupoli, et al., "Transpeptidase-mediated incorporation of D-amino acids into bacterial peptidoglycan", JACS, 133(28):10748-51 (2011).
Lutolf, et al., "Synthesis and Physicochemical Characterization of End-Linked Poly(ethylene glycol)-co-peptide Hydrogels Formed by Michael-Type Addition", Biomacromolecules, 4:713-722 (2003).
Maheshwari, et al., "Cell adhesion and motility depend on nanoscale RGD clustering", J. Cell. Sci., 113 (Pt 1):1677-1686 (2000).
Mao, et al., "Fibronectin fibrillogenesis, a cell-mediated matrix assembly process", Matrix Biology, 24:389-399 (2005).
McCauley, et al., "Pluripotent stem cell-derived organoids: Using principles of developmental biology to grow human tissues in a dish", Dev., 144(6):958-962 (2017).
Miyoshi, et al., "Prostaglandin E2 promotes intestinal repair through an adaptive cellular response of the epithelium", EMBO J., 36:5-24 (2017).
Muñoz, et al., "The Lgr5 intestinal stem cell signature: Robust expression of proposed quiescent '+4' cell markers", EMBO J., 31:3079-3091 (2012).
Nakamura, Advancing Intestinal Organoid Technology Toward Regenerative Medicine, CMGH, 5:51-60 (2018).
Nardo, et al., "Expression of alpha(v)beta3 and alpha4beta1 integrins throughout the putative window of implantation in a cohort of healthy fertile women", Acta Obstet. Gynecol. Scand., 81(18): 753-8 (2002).
Oesterhelt, et al., "Single molecule force spectroscopy by AFM indicates helical structure of poly(ethylene-glycol)in water", New J. Phys., 1:6 (1999).
Patey, et al., "Distribution of cell adhesion molecules in infants with intestinal epithelial dysplasia (tufting enteropathy)", Gastroenterology, 113(3):833-843 (1997).
Pepels, et al., "Self-healing systems based on disulfide-thiol exchange reactions", Polym. Chem., 4:4955-4965 (2013).
Pérez, et al., "A Collagen Peptide-Based Physical Hydrogel for Cell Encapsulation", Macromol. Biosci., 11(10): 1426-1431 (2011).

(56) References Cited

OTHER PUBLICATIONS

Pérez, et al., "Tuning the thermosensitive properties of hybrid collagen peptide-polymer hydrogels", Chem. Commun., 50(60):8174-8176 (2014).
Petrie, et al., "Tissue engineering: Multivalent integrin-specific ligands enhance tissue healing and biomaterial integration", Sci. Transl. Med., 2(45):45ra60 (2010).
Popp, et al., "Making and breaking peptide bonds: protein engineering using sortase", Angew. Chem. Int. Ed., 50(22):5024-5032 (2011).
Raeeszadeh-Sarmazdeh, et al., "Site-specific immobilization of protein layers on gold surfaces via orthogonal sortases", Colloids and Surfaces B: Biointerfaces, 128:457-463 (2015).
Rahil, et al., "Nanoscale mechanics guides cellular decision making", Integr. Biol., 8(9): 929-935 (2016).
Reddy, et al., "Engineering epidermal growth factor for enhanced mitogenic potency", Nat. Biotechnol., 14(13):1696-1699 (1996).
Reyes, et al.,"Engineering integrin-specific surfaces with a triple-helical collagen-mimetic peptide", J. Biomed. Mater. Res.—Part A., 65:511-523 (2003).
Ricard-Blum, "The Collagen family", Cold Spring Harb Perspect Biol, 3:a004978 (2011).
Rodríguez-Colman, et al., "Interplay between metabolic identities in the intestinal crypt supports stem cell function", Nature, 543(7645):424-427 (2017).
Rossi, et al., "Progress and potential in organoid research", Nat. Rev. Genet., 19(11):671-687 (2018).
Ruiz-Herrero, et al., "Organ size control via hydraulically gated oscillations", Development, 144(23):4422-4427 (2017).
Salinas, et al., "The influence of the RGD peptide motif and its contextual presentation in PEG gels on human mesenchymal stem cell viability", J Tissue Eng Regen Med., 2(5):296-304 (2008).
Sato, et al., "Long-term expansion of epithelial organoids from human colon, adenoma, adenocarcinoma, and Barrett's epithelium", Gastroenterology, 141:1762-1772 (2011).
Sato, et al., "Single Lgr5 stem cells build crypt-villus structures in vitro without a mesenchymal niche", Nature, 459:262-5 (2009).
Schindelin, et al., "Fiji: An open-source platform for biological-image analysis", Nat. Methods, 9(7):676-682 (2012).
Soofi, et al., "The elastic modulus of MatrigelTM as determined by atomic force microscopy", J. Struct. Biol., 167:216-219 (2009).
Sperinde, et al., "Synthesis and characterization of enzymatically-cross-linked poly(ethylene glycol) hydrogels", Macromolecules, 30: 5255-5264 (1997).
Stahl, et al., "PEG-based hydrogels with collagen mimetic peptide-mediated and tunable physical cross-links", Biomacromolecules, 11:2336-2344 (2010).
Stallmach, et al., "Diminished expression of integrin adhesion molecules on human colonic epithelial cells during the benign to malign tumour transformation", Gut,. 33:342-346 (1992).
Starchenko, et al., "Clustering of integrin α5 at the lateral membrane restores epithelial polarity in invasive colorectal cancer cells", Mol. Biol. Cell., 28:1288-1300 (2017).
Stelzner, et al., "A nomenclature for intestinal in vitro cultures", Am. J. Physiol.—Gastrointest. Liver Physiol., 302 (2012) G1359-63 (2012).
Sumigray, et al., "Morphogenesis and Compartmentalization of the Intestinal Crypt", Dev. Cell, 45(2): 183-197 (2018).
Suzuki, et al., "Single cell analysis of Crohn's disease patient-derived small intestinal organoids reveals disease activity-dependent modification of stem cell properties", J. Gastroenterol., 53(9):1035-1047 (2018).
Tabibzadeh, "Patterns of expression of integrin molecules in human endometrium throughout the menstrual cycle", Hum. Reprod., 7:876-882 (1992).
Tadaki, et al., "The functional importance of hydrophobicity of the tyrosine at position 13 of human epidermal growth factor in receptor binding", J Biol Chem., 268(14):10114-9 (1993).
Talbot, et al., "Proteome array identification of bioactive soluble proteins/peptides in Matrigel: relevance to stem cell responses", Cytotechnology, 67:873-883 (2015).
Tanrikulu, et al., "Optimal interstrand bridges for collagen-like biomaterials", J. Am. Chem. Soc., 136(39):13490-13493 (2014).
Tempest, et al., "Does human endometrial LGR5 gene expression suggest the existence of another hormonally regulated epithelial stem cell niche", Hum. Reprod., 33: 1052-1062 (2018).
Tong, et al., "Paneth cell multi-potency induced by Notch activation following injury", Cell Stem Cell., 23(1):46-59.e5 (2018).
Trachsel, et al., "Enzymatically crosslinked poly(2-alkyl-2-oxazoline) networks for 3D cell culture", J. Mater. Chem. B., 6:7568-7572 (2018).
Turco, et al., "Long-term, hormone-responsive organoid cultures of human endometrium in a chemically defined medium", Nat. Cell Biol., 19(5):568-577 (2017).
Valdez, et al., "On-demand dissolution of modular, synthetic extracellular matrix reveals local epithelial-stromal communication networks", Biomaterials, 130:90-103 (2017).
Vandussen, et al., "Development of an enhanced human gastrointestinal epithelial culture system to facilitate patient-based assays", Gut, 64(6):911-20 (2015).
Wang, et al., "A tough biodegradable elastomer", Nat. Biotechnol., 20(6):602-606 (2002).
Wang, et al., "Bioengineered Systems and Designer Matrices That Recapitulate the Intestinal Stem Cell Niche", CMGH, 5:440-453.e1 (2018).
Wilson, et al., "Hydrogels with well-defined peptide-hydrogel spacing and concentration: Impact on epithelial cell behavior", Soft Matter, 8(2):390-398 (2012).
Wojtowicz, et al., "Coating of Biomaterial Scaffolds with the Collagen-Mimetic Peptide GFOGER for Bone Defect Repair", Biomaterials, 31(9):2574-2582 (2010).
Yap, et al., "Laminins in Cellular Differentiation", Trends Cell Biol., 29(12):987-1000 (2019).
Yu, et al., "Paneth Cell Multipotency Induced by Notch Activation following Injury", Cell Stem Cell, 23:46-59.e5 (2018).
Zustiak, et al., "Hydrolytically degradable poly(ethylene glycol) hydrogel scaffolds with tunable degradation and mechanical properties", Biomacromolecules, 11(5):1348-1357 (2010).
International Search Report received for PCT Patent Application No. PCT/US2023/077081, mailed on May 14, 2024, 6 pages.

\* cited by examiner

PEG HYDROGEL NETWORK

SYNTHETIC HYDROGELS FOR ORGANOGENESIS

CROSS-REFERENCE TO RELATED APPLICATIONS

This application claims benefit of U.S. Provisional Application No. 62/879,920, filed Jul. 29, 2019, which is hereby incorporated herein by reference in its entirety.

STATEMENT REGARDING FEDERALLY SPONSORED RESEARCH

This invention was made with government support under EB0219080 awarded by the National Institutes of Health. The government has certain rights in the invention.

REFERENCE TO SEQUENCE LISTING

The Sequence Listing submitted Oct. 26, 2020, as a text file named "MIT_20047_ST25," created on Oct. 14, 2020, and having a size of 10,358 bytes is hereby incorporated by reference pursuant to 37 C.F.R. § 1.52(e)(5).

FIELD OF THE INVENTION

The invention is in the field of hydrogels for organogenesis, particularly synthetic hydrogels for culture of human organoids.

BACKGROUND OF THE INVENTION

Organoids are three-dimensional structures derived from stem cells with organ-specific cell types and microarchitecture similar to the tissue of origin. These models offer a closer look into organogenesis unique to human that are not possible with animal models. In addition, human organoids allow for personalized medicine and autologous transplants using patient-derived crypts or stem cells cultured and expanded in vitro. However, stem cell-derived organoids suffer several limitations, primary of which is the reliance on natural hydrogels as a 3D scaffold, such as MATRIGEL®.

MATRIGEL® is a commercial product widely used to provide the 3D scaffold for the growth of organoids of all cell types. However, the reliance on MATRIGEL®®, or similar naturally derived biopolymer matrices, as the scaffold for organoid growth introduces a number of significant limitations into the study and use of the resultant organoids, and severely limits further development of the field.

MATRIGEL® is derived from a basement membrane extracellular matrix (ECM)-rich mouse sarcoma and therefore introduces a significant risk of immunogen or pathogen transfer if given to a patient. Additionally, the batch-to-batch variability of MATRIGEL® may lead to inconsistent cell behaviors, introducing unknown and potentially confounding variables that complicate the interpretation of both basic and translational research. Further, the role of MATRIGEL® in organoid formation remains poorly understood. ECM is known to implicate in the regulation of tissue development and function. The specific roles of ECM factors are difficult to ascertain using MATRIGEL® given that its molecular components cannot be readily manipulated. It is unclear whether MATRIGEL® serves merely as a passive 3D scaffold providing physical support to the growing organoid, or actively influences organoid formation by providing essential biological cues. The cumbersome process to remove MATRIGEL® and recover the organoids for downstream analysis is an additional challenge.

Additionally, organoids derived from induced pluripotent stem cells (iPSC) result in complex tissue structures (for example, iPSC-derived intestinal organoids typically have smooth muscle and stroma surrounding epithelial cells (McCauley et al., Dev. 144:958-962 (2017)), but cell maturation is limited to fetal stages. There is great interest in organoids derived from postnatal tissue biopsies, as these capture features of (patho)-physiological states of mature tissues, such as epigenetic changes and somatic mutations associated with donor tissue's natural or diseased state.

There remains a need for fully-defined hydrogels supporting organogenesis, especially organogenesis from biopsied human cells, with control over complex cell-matrix interactions, which are not possible with complex natural hydrogels.

Therefore, it is an object of the present invention to provide synthetic hydrogels for organogenesis from mammalian cells, especially from human cells.

It is another object of the present invention to provide methods of making the synthetic hydrogels.

It is yet another object of the present invention to provide methods of using the synthetic hydrogels.

SUMMARY OF THE INVENTION

Synthetic hydrogels for organogenesis from mammalian cells, preferably biopsied human cells, and especially epithelial cells, have been developed. The synthetic hydrogels are tunable matrices with components select to support growth of cells of different origins (e.g., cells of mouse and human origin) and from different organs and tissues (e.g., endometrial cells, or intestinal cells). The synthetic hydrogels provide a matrix where the complex cell-matrix interactions can be controlled, which are not possible with complex natural hydrogels.

The synthetic hydrogel typically includes a plurality of biodegradable polymers and one or more binders. The biodegradable polymers are typically branched biodegradable polymers. The biodegradable polymers can be one or more polyalkylene glycols, preferably polyethylene glycols. The biodegradable polymers typically have molecular weight between about 2 kDa and about 100 kDa. The biodegradable polymers can be functionalized.

The binders are typically synthetic peptides and include adhesion ligands and extracellular matrix component binders (ECM binders). The adhesion ligands are typically cell-binding peptides, for example, integrin binding peptides. The integrin binding peptides can be derived from collagen, fibronectin, and/or laminin. For example, the adhesion ligands may contain the amino acid sequence GFOGER (SEQ ID NO:1) and/or amino acid sequence PHSRN (SEQ ID NO:2). The adhesion ligands may be linear or branched.

The ECM binders are typically synthetic peptides with affinity to extracellular matrix components, preferably the ECM proteins. For example, an ECM binder can be a peptide having affinity to fibronectin, collagen, laminin, other ECM components, or combinations thereof. The extracellular protein-binding peptides may contain the sequence $NH_2$-GCRE-ISAFLGIPFAEPPMGPRRFLPPEPKKP(Am) (SEQ ID NO:4) and $NH_2$-GCRE-TLQPVYEYMVGV-COOH (SEQ ID NO:5).

The molar ratio of the adhesion ligand to the ECM binder(s) (collective molar concentration if more than one type of ECM binder is present), is typically greater than 1:1, such as between about 1:1 and about 5:1, between about 1.2:1 and about 5:1, between about 1.5:1 and about 5:1, such as about 1.5:1, about 2:1, about 2.5:1, about 3:1, about 3.5:1, about 4:1, about 4.5:1, or about 5:1.

The biodegradable polymers in the synthetic hydrogel are typically crosslinked via one or more cross-linkers. The cross-linker may be a synthetic peptide. In some embodiments, the cross-linkers contain a protease-, proteinase-, or transpeptidase-cleavable motif. The cross-linkers can be cleavable by a matrix-metalloproteinase (MMP) and/or a sortase transpeptidase. An exemplary cross linker includes any one of the amino acid sequences LPXTG (SEQ ID NO:6), LPXSG (SEQ ID NO:7), or LAXTG (SEQ ID NO:8), where X is any one of the natural amino acids, but preferably arginine (Arg, R).

In some embodiments, the synthetic hydrogel additionally includes one or more inhibitors of apoptosis, such as inhibitors of dissociation-induced apoptosis, for example, Rho kinase inhibitors.

Alternatively, or additionally, the synthetic hydrogel can include cells, tissues, organs, or combinations thereof.

Methods of forming a synthetic hydrogel is also provided. Typically, the methods include a first step of combining a plurality of biodegradable polymers and one or more binders, where the polymers can have a first linking moiety and the binders can have a second linking moiety. The first linking moiety of the polymers can be a reactive group, for example, a vinyl sulfone group. The second linking moiety can be a reactive group, for example, a thiol group. The thiol group is preferably a free thiol group at the terminus of the binders. The weight/volume percentage of polymers can be between about 3.5 and 10%, for example, 5%. The binders can have a concentration between about 0.1 mM and about 10 mM, preferably between about 0.1 mM and 6 mM, most preferably between about 0.25 mM and about 3.5 mM. For example, the adhesion ligands may be at a concentration between about 0.1 mM and about 5 mM, preferably between about 0.25 mM and about 3 mM, most preferably about 1.5 mM. The ECM protein-binding peptides may be at a concentration between about 0.1 mM and 5 mM, preferably between about 0.25 mM and 1 mM, most preferably about 0.5 mM. Generally, the concentration of ECM protein binder and the concentration of adhesion ligand are at a ratio between about 1:1 and 1:10, such as between about 1:1 and about 1:9, about 1:1 and about 1:8, about 1:1 and about 1:7, about 1:1 and about 1:6, about 1:1 and about 1:5, about 1:1 and about 1:4, about 1:1 and about 1:3, about 1:1 and about 1:2, about 1:1 and about 1:1.5.

In some embodiments, the methods additionally include a second step of) combining the adduct of the first step and one or more cross linkers to form cross-linked hydrogel. The cross-linkers typically have a cross-linking moiety to form the crosslinked hydrogel. Each cross-linker may have two cross linking moieties at each terminus. The cross-linking moiety can be a thiol group. In some embodiments, the ratio of crossing linking moiety:first linking moiety has a ratio between 0.35 and 1, for example, 0.5.

Alternatively, or additionally, the methods include combining cells, and/or one or more inhibitors of apoptosis, and the adduct of the first step.

Methods for organogenesis using the synthetic hydrogels are also provided. Typically, the methods include incorporating a stem cell into a synthetic hydrogel. In some embodiments, the synthetic hydrogel supports the growth of organoids from human cells, for example, human epithelial organoids, human endometrial organoids, human gastrointestinal organoids, or a combination thereof.

BRIEF DESCRIPTION OF THE DRAWINGS

FIG. 1A shows integrin expression in the intestinal crypt serves to identify integrin binding peptides from the biomaterial "toolbox" that engage $\alpha 5\beta 1$ (PHSRN-K-RGD) and $\alpha 2\beta 1$ (GFOGER). FIGS. 1B and 1C show the 8-arm PEG macromers of 20- and 40-kDa served to create matrices with tunable bulk biomechanical properties and tunable local integrin binding display due to differences on PEG-arm contour length. FIGS. 1D-1F show synthetic matrix assembly using 8-arm PEG macromer with vinyl sulfone (VS) reactive groups in combination with thiol-reactive peptides. A shift in pH allows for Michael-type addition reaction to occur. The branched and triple helical conformation of the integrin binding peptides when bound to the PEG arm is shown (FIG. 1F). A single PHSRN-K-RGD peptide is depicted grafted to a single PEG-arm. In contrast, the GFOGER peptide in its triple helical conformation (GFOGER$_{th}$) is depicted grafted to a single PEG-arm.

FIG. 2D show enteroid diameters measured from mouse colon donor. The number of enteroids measured per condition is depicted below each violin plot. MATRIGEL® diameters were significantly bigger (P<0.0001) for all human conditions, than the diameter of enteroids emerging in the synthetic hydrogels. The median enteroid diameter and quartiles in the PEG-20-GFOGER and PEG-40/20-GFOGER matrices were statistically similar within each donor (P>0.9999). For mouse, the median enteroid diameter and quartiles were statistically similar in MATRIGEL®, PEG-20-GFOGER and PEG-40/20-GFOGER (#P>0.9999). Data was analyzed using Kruskal-Wallis multiple comparison of the mean ranks. ns: not significant, *P=0.0332, P=0.0021, *P=0.0002, **P<0.0001.

FIG. 6B shows enteroid formation efficiency in hydrogels made at 0.17 and 0.26 mM of GFOGERth when adjusted for swelling. Results are from quantification of a representative experiment from FIG. 6A. Each symbol represents a single hydrogel with the mean and SEM. The data was analysed using two tailed t-test with Mann-Whitney test. **P=0.0079.

FIGS. 7A-7G are diagrams and graphs showing that modulating RGD ligand biophysical presentation does not increase enteroid formation compared to GFOGER. FIGS. 7A-7E are diagrams showing synthetic ECMs with various α5β1 and α2β1 ligand presentation. Schematic of ligand display on PEG-20 arms highlighting the length of the PEG arm and the linear or triple helical nature of the integrin binder peptides is shown. All hydrogels were made at 1.5 mM integrin binding peptide, 0.25 mM BM-binder, and 0.25 mM FN-binder, at 50% XL-MMP-SrtA crosslinker. The concentration of the integrin ligand adjusted for swelling was either 0.77 mM (for RGD, G11RGD, and PHSRN-K-RGD) or 0.26 mM (for CMPRGD and GFOGER, triple helical peptide concentration). FIG. 7F-7G are graphs showing the enteroid formation efficiency (%) (7F) and enteroid diameters (7G) on the indicated matrices. Results are from two independent experiments. Each symbol represents a single hydrogel with the mean and SEM. The data was analysed using one-way ANOVA, Holm-Sidak multiple comparison of the mean. ns: not significant, *P=0.0248, P=0.0050, *P=0.0003,****P<0.0001.

FIGS. 8B and 8C are graphs showing the time-lapsed imaging analysis of changes in diameter (μm) of a single enteroid from days 4 to 6 in the PEG-20-GFOGER hydrogels (FIG. 8B) or MATRIGEL® (FIG. 8C).

FIG. 11 shows fold increase in cell number after six days of culture in each passage from two human donors grown in PEG-20-GFOGER or MATRIGEL®. Data represent three consecutive passages using enteroids collected from pooled hydrogels at each passage. All PEG-20-GFOGER hydrogels were made at nominal concentrations of 0.5 mM GFOGERth, 0.25 mM BM-, and 0.25 mM FN-binder at 50% XL-MMP-SrtA crosslinker.

DETAILED DESCRIPTION OF THE INVENTION

I. Definitions

Figure 1A:
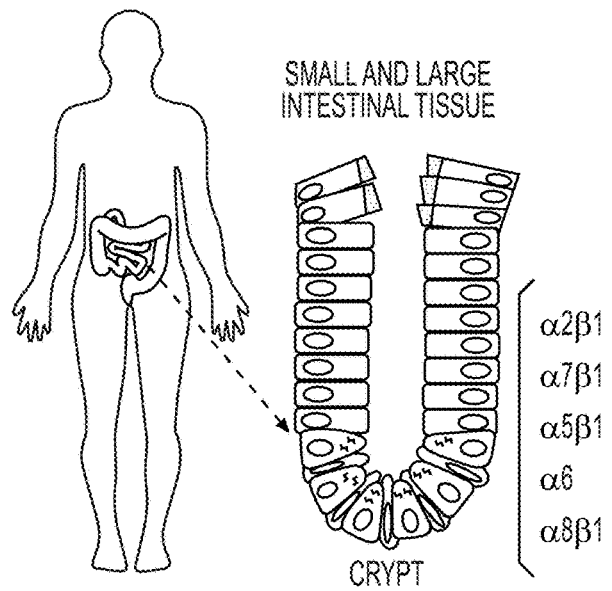
FIGS. 1A-1F are diagrams and flow charts showing niche-inspired synthetic matrix design.

As used herein, the term "hydrogel" refers to a substance formed when an organic polymer (natural or synthetic) is cross-linked via covalent, ionic, or hydrogen bonds to create a three-dimensional open-lattice structure which entraps water molecules to form a gel. Biocompatible hydrogel refers to a polymer forms a gel which is not toxic to living cells and allows sufficient diffusion of oxygen and nutrients to the entrapped cells to maintain viability.

As used herein, the term "biodegradable", in the context of polymer, refers to a polymer that will degrade or erode by enzymatic action and/or hydrolysis under physiologic conditions to smaller units or chemical species that are capable of being metabolized and/or eliminated.

As used herein, the term "binder" refers to peptides, preferably synthetic peptides, with affinity to one or more proteins. The proteins may be cell-associated proteins and/or cell-secreted proteins. Typically, binders, in the context of components of the hydrogel, include adhesion ligands and ECM protein-binding peptides.

As used herein, the terms "inhibitor", "apoptosis inhibitor" refers to small molecules with known inhibitory effects on cellular apoptosis. The inhibitor may inhibit any stage of cellular apoptosis. Preferably the inhibitor inhibits dissociation-induced apoptosis. The reduction in apoptosis in a cell population may be compared to a control. The control may include the same type, or similar cells, grown under the same conditions, in the absence of the inhibitor.

As used herein, the term "molecular weight", in the context of polymers, refers to generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

As used herein, the term "molecular weight", in the context of biological molecules, such as peptides, proteins, glycoproteins, etc., generally refers to the molar mass of the molecule in g/mol, or Daltons, and may be measured by any suitable technique, such as electrophoresis, or mass spectrometry.

As used herein, the term "functionalize" refers to modifying in a manner that results in the attachment of a functional group or moiety. For example, a molecule may be functionalized by the introduction of a molecule which makes the molecule a strong nucleophile or strong electrophile. For example, a molecule, such as hyaluronic acid, may be functionalized to become a thiol, amine, acrylate, or quinone.

As used herein, the term "peptide" refers to a biological molecule, which may include "polypeptide," and/or "oligopeptide," and refers to a chain of natural and/or synthetic amino acid residues linked together by covalent bonds (e.g., peptide bonds). The length of the peptide is limited at the lower end only by the minimum number amino acids required to form a self-assembling peptide.

As used herein, the term "adhesion ligand" refers to a synthetic peptide ligand for affinity to cellular proteins, typically to cell adhesion molecules (CAMs). Typical cell adhesion molecules include integrins, immunoglobulin superfamily (IgSF) CAMS, cadherins, and selectins. The adhesion ligands may derive from proteins of the ECM. The adhesion ligands may be linear or branched.

As used herein, the term "extracellular matrix", "ECM" refers to the components and/or the network of extracellular macromolecules, such as proteins, enzymes, and glycoproteins, that provide structural and biochemical support of surrounding cells. The extracellular matrix includes the interstitial matrix and the basement membrane components of the ECM include proteoglycans heparan sulfate, chondroitin sulfate, keratan sulfate; non-proteoglycan polysaccharide hyaluronic acid, and proteins collagen, elastin, fibronectin, and laminin.

As used herein, the term "extracellular matrix-binding peptide" refers to a synthetic peptide with affinity to ECM components.

As used herein, the term "hydrogel matrix" typically refers to the network of cross-linked polymers forming the hydrogel. The hydrogel matrix may or may not include the binders.

As used herein, the term "crosslinker" refers to a small molecule or a peptide molecule containing reactive groups to bond one polymer chain to another. The bonds may be in the form of covalent bonds or ionic bonds.

As used herein, the term "linking moiety" refers to a moiety containing any known suitable reactive group that reacts with another reactive group to form a bond, as exemplified herein. The bond may be in the form of covalent bonds or ionic bonds.

As used herein, the term "amino acid" refers to standard nomenclature, amino acid residue as denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "cleavable motif", in the context of proteins, refers to a sequence of amino acids, such as to a sequence of two, three, four, five, six, etc., amino acids that are recognized by one or more proteolytic enzymes, such as proteases, proteinases, peptidases, and transpeptidases, such as protein sorting transpeptidases. The cleavable motif may be a synthetic or a naturally occurring recognition site for the proteolytic enzymes.

"Mammalian cell" refers to any cell derived from a mammalian subject suitable for transplantation into the same or a different subject. The cell may be xenogeneic, autologous, or allogeneic. The cell can be a primary cell obtained directly from a mammalian subject. The cell may also be a cell derived from the culture and expansion of a cell obtained from a subject. For example, the cell may be a stem cell. Immortalized cells are also included within this definition. In some embodiments, the cell has been genetically engineered to express a recombinant protein and/or nucleic acid.

"Autologous" refers to a transplanted biological substance taken from the same individual.

"Allogeneic" refers to a transplanted biological substance derived from a different individual of the same species.

"Xenogeneic" refers to a transplanted biological substance taken from a different species.

As used herein, the term "variant" refers to a peptide or a polypeptide that differs from a reference peptide or a polypeptide but retains the same mechanism of activity. A typical variant of a peptide or a polypeptide differs in amino acid sequence from another, reference peptide or a polypeptide. Generally, differences are limited so that the sequences of the reference peptide or a polypeptide and the variant are closely similar overall and, in many regions, identical. A variant and reference peptide or a polypeptide may differ in amino acid sequence by one or more modifications (e.g., substitutions, additions, and/or deletions). A substituted or inserted amino acid residue may or may not be one encoded by the genetic code. A variant of a peptide or a polypeptide may be naturally occurring such as an allelic variant, or it may be a variant that is not known to occur naturally.

Modifications and changes can be made in the structure of the peptide or a polypeptide of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, and antigens. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). In particular, embodiments of the polypeptides can include variants having about 50%, 60%, 70%, 80%, 90%, and 95% sequence identity to the polypeptide of interest.

Use of the term "about" is intended to describe values either above or below the stated value in a range of approx. +/−10%; in other embodiments the values may range in value either above or below the stated value in a range of approx. +/−5%.

II. Synthetic Hydrogels

Synthetic hydrogels for supporting organoid growth have been developed which are particularly suited for human organoid culture, such as human epithelial organoid culture.

The synthetic hydrogels formed from biodegradable polymers and binding agents (or "binders") provide chemically defined and versatile cell cultures as alternatives to natural, animal-derived matrices such as MATRIGEL® These synthetic hydrogels are based on the micro-environmental properties and components governing the distinct stages of stem cell-driven organoid formation and maintenance. These can be used to create fully defined hydrogel matrix for the expansion of stem cells and organoids with synthetic hydrogel of precise biomechanical and biological properties. These synthetic hydrogels also offer a window of opportunity for large-scale production of clinical-grade cells and tissues, especially human cells and tissues. The biomechanical and biological properties of the synthetic hydrogels can be "tuned" or optimized by varying polymer structures, polymer molecular weight, and binders to support organoid growth from different types of cells, normal or tumor-derived. For example, synthetic hydrogels formed from multi-arm polyethylene glycol (PEG) and integrin binding peptides support human intestinal stem cell growth.

The components of the synthetic hydrogel can be provided either separately or combined, in dry form, such as powders, or in solution form. The synthetic hydrogel forms when cross linking conditions are applied. For example, the components of the synthetic hydrogel are dissolved in a liquid, such as water or medium, and the solution temperature is increased to induce cross linking and form the hydrogel.

Additional natural ligands such as growth factor ligands which are modified for crosslinking or synthetic ligands (such as y13g mutant of EGF (Reddy, et al 1996. Nat. Biotechnol. 14:1696-1699; Tadaki, et al, J Biol Chem 1993 May 15; 268(14):10114-9) may be added to the synthetic matrices as growth factor ligands. The sequence is the same as natural epidermal growth factor, but substituting either glycine, arginine, leucine, or histidine for the tyrosine at position 13.

In some embodiments, the synthetic hydrogel additionally includes one or more inhibitors of dissociation-induced apoptosis, for example, protein kinase inhibitors. The incorporation of inhibitors is important for preventing death of encapsulated cells, especially for human organoid culture. In some embodiments, the inhibitor is at a concentration between 1 nM and 1 mM, between 10 nM and 100 µM, or between 100 nM and 50 µM, for example, about 10 µM.

Alternatively, or additionally, the synthetic hydrogel can include cells, tissues, organs, or combinations thereof.

A. Polymers

The synthetic hydrogel typically includes a plurality of biodegradable polymers, and one or more binders. The hydrogels typically include an apoptosis inhibitor, such as one or more inhibitors of dissociation-induced apoptosis. The incorporation of inhibitors is important for preventing death of encapsulated cells, especially for human organoid culture. An exemplary biodegradable polymer is PEG. Typically, the PEG has a molecular weight greater than 2 kDa, such as between about 2 kDa and 100 kDa. The molecular weight of the PEG may be between about 5 kDa and about 90 kDa, between about 5 kDa and about 80 kDa, between about 5 kDa and about 70 kDa, between about 5 kDa and about 60, such as about 50 kDa, about 40 kDa, about 30 kDa, about 20 kDa or about 10 kDa. Preferably, the molecular weight of the PEG is about 20 kDa or about 40 kDa.

The plurality of biodegradable polymers may include PEGs of various molecular weights, for example, a mixture of 20 kDa PEG and 40 kDa PEG. The plurality of biodegradable polymers may include PEGs of at least two molecular weights, a lower molecular weight PEG and a higher molecular weight PEG, where the ratio of the lower molecular weight PEG to a higher molecular weight PEG is about 1:0.1, about 1:0.25, about 1:0.5, about 1:1, about 1:1.5, about 1:2; about 1:2.5, about 1:3, or more. For example, in a hydrogel containing a 20 kDa 8-arm PEG and a 40 kDa 8-arm PEG, the ratio of the 20 kDa to 40 kDa PEG is about 1:0.1, about 1:0.25, about 1:0.5, about 1:1, about 1:1.5, about 1:2; about 1:2.5, about 1:3, or more, preferably about 1:1.

Preferably, the biodegradable polymers are branched biodegradable polymers. The biodegradable polymers can be functionalized biodegradable polymers, for example, polymers functionalized with a first linking moiety. The first linking moiety is typically a reactive group such as a vinyl sulfone group. In some embodiments, the synthetic hydrogel contains a weight/volume percentage of polymers between 1% and 50%, between 2% and 25%, or between 3.5% and 10%, for example, about 2%, about 3%, about 4%, or about 5% (w/v).

In some embodiments, the synthetic hydrogel contains a weight/weight percentage of polymers between 1% and 50%, between 2% and 25%, or between 3.5% and 10%, for example, about 2%, about 3%, about 4%, or about 5% (w/w).

The synthetic hydrogel is formed from a plurality of biodegradable polymers. Exemplary biodegradable polymers that can form hydrogels include, but are not limited to, polyalkylene glycol such as polyethylene glycol (PEG) and polyalkylene glycol copolymers such as PEG copolymers, polyoxazoline, polyaliphatic polyurethanes, polyether polyurethanes, polyester polyurethanes, polyamides, polyvinyl alcohols, polytetramethylene oxide, polyvinyl pyrrolidone, polyacrylamide, polyhydroxy ethyl acrylate, polyhydroxy ethyl methacrylate. Other suitable hydrogel forming polymers are described in the art, for example, Kadajji and Betageri, *Polymers,* 3:1972-2009 (2011). The biodegradable polymer can be linear or branched (i.e. multi-armed), preferably branched polymers.

In polymer chemistry, branching occurs by the replacement of a substituent, e.g., a hydrogen atom, on a monomer subunit, by another covalently bonded chain of that polymer; or, in the case of a graft copolymer, by a chain of another type. Branching may result from the formation of carbon-carbon or various other types of covalent bonds. Branching by ester and amide bonds is typically by a condensation reaction, producing one molecule of water (or HCl) for each bond formed.

The branching index measures the effect of long-chain branches on the size of a macromolecule in solution. It is defined as $g=<sb2>/<sl2>$, where sb is the mean square radius of gyration of the branched macromolecule in a given solvent, and sl is the mean square radius of gyration of an otherwise identical linear macromolecule in the same solvent at the same temperature. A value greater than 1 indicates an increased radius of gyration due to branching.

A preferred biodegradable polymer is polyalkylene glycol, such as polyethylene glycol, also known as PEG. PEGs can cross link by cell-compatible crosslinking reactions, with or without cross linkers. The PEG can be linear or branched. Preferred PEGs are branched polymers with at least 2, 3, or 4 arms, for example, 4 arms, 6 arms, or 8 arms. Typically, the arm has a length from the backbone of the polymer to the terminus of the arm between 1 and 100 nm, between 10 and 90 nm, or between 10 and 50 nm, for example, 20 nm.

Representative PEG molecular weights include 1 kDa, 2 kDa, 3 kDa, 4 kDa, 5 kDa, 6 kDa, 8 kDa, 10 kDa, 15 kDa, 20 kDa, 30 kDa, 50 kDa, and 100 kDa. In preferred embodiments, the PEG has a molecular weight between about 2 kDa and about 100 kDa, for example, 20 kDa or 40 kDa. PEG of any given molecular weight may vary in other characteristics such as length, density, and branching. In preferred embodiments, the PEG is 8-arm with a MW of 20 kDa. In some embodiments, the PEG is 8-arm with a MW of 40 kDa. In some embodiments, PEGs of various molecular weights can be used, for example, a mixture of 20 kDa PEG and 40 kDa PEG.

In some embodiments, copolymers of PEG or other polymers described above may be used to make the synthetic hydrogel. In certain embodiments, the PEG or other polymers may locate in the interior positions of the copolymer. Alternatively, the PEG or other polymers may locate near or at the terminal positions of the copolymer.

In preferred embodiments, the biodegradable polymers are functionalized with a first linking moiety. The first linking moiety may locate in the interior position of the polymer or near or at the terminal positions of the arm of the polymer. The number of first linking moiety on a polymer can be varied. For example, at least 1, 2, 3, 4, 5, 6, 7, 8, 10, 12, 16, 20, 24, and 32 first linking moieties may be included in the polymer. The first linking moiety can be a reactive group that reacts with binders functionalized with a second linking moiety to form polymer-binder adducts. Additionally, and alternatively, the first linking moiety can be a reactive group that is involved in crossing linking either between different biodegradable polymers or between the biodegradable polymers/polymer-binder adducts and cross linkers. The first linking moiety can be the same or different in the plurality of biodegradable polymers.

In some embodiments, the reactive group can be an electrophilic group or a nucleophilic group. Exemplary electrophilic groups include, but are not limited to, azide, cyano, trifluoromethyl, vinyl groups or vinyl-containing groups (e.g. vinyl sulfone), maleimide. In some embodiments, the electrophilic group is vinyl sulfone or maleimide. Exemplary nucleophilic groups include, but are not limited to, thiol, hydroxyl, alkoxy or aroxy (e.g., methoxy, benzyloxy), or primary, secondary, or tertiary amine. In some embodiments, the nucleophilic group is a thiol group.

In preferred embodiments, the biodegradable polymer has a weight/volume percentage in the hydrogel of between 1% and 50%, between 2% and 25%, or between 2% and 10%, for example, about 2%, about 3%, about 4%, or about 5%.

B. Binders

Typically, the hydrogels include one or more binders. The binders are typically synthetic peptides and include adhesion ligands and ECM protein binders. The binders may be linear or branched. The binders typically have at least two ends. The binders in the hydrogel are typically associated with the polymer at one end and are free at the other end.

The binders may have a secondary structure. The binders may be peptides having a single chain amino acid sequence. The binders may be branched peptides. The binders may be peptides having a single chain amino acid sequence that self assembles into dimers, trimers, etc. The secondary structure of the dimers and trimers may be any secondary structure for proteins and peptides, including alpha helices, beta sheets, beta turns, or omega loops.

A concise list of exemplary binders is presented in Table 5.

The binders can be, for example, adhesion ligands and peptide binders. In some embodiments, the adhesion ligands are cell-binding peptides for cell adhesion, for example, integrin binding peptides. The integrin binding peptides can be a collagen-I derived peptide, laminin-derived peptide, and/or a fibronectin derived peptide. In some embodiments, the peptide binders are extracellular protein-binding peptides to capture proteins secreted by cells during organogenesis. For example, the extracellular protein-binding peptide can be a peptide having affinity to fibronectin, collagen, laminin, other basement membrane proteins, or combinations thereof. Peptides having affinity to fibronectin capture fibronectin produced by endometrial stromal fibroblasts throughout the cycle. Peptides having affinity to collagen and laminin capture laminin and type IV collagen basement membrane proteins that are normally produced by the epithelium during all menstrual cycle stages and locally produced and accumulated in the pericellular region of hormonally responsive fibroblasts in the stroma.

The binder typically contains a second linking moiety. The second linking moiety can be a reactive group that reacts with the first linking moiety to form a polymer-binder adduct. An exemplary second linking moiety is a thiol group. Each polymer may have at least one binder incorporated, for example, 1 or 3 binders incorporated.

In some embodiments, binders such as adhesion ligands are incorporated at the terminus of the arm of a multi-armed PEG such as an 8-arm PEG. The polymer-binder adduct can have an arm length from the polymer backbone to the terminus of the adhesion ligand between 10 and 100 nm. For example, an 8-arm 20 kDa PEG-GFOGER adduct has an arm length about 26 nm (~16 nm PEG and ~10 nm GFOGER). Each arm of the 8-arm 20 kDa PEG may have three GFOGER peptides incorporated. This is typically through formation of triple-helix of the three GFOGER peptides, where one of the peptides binds to one arm. An 8-arm 20 kDa PEG-PHKRGD adduct has an arm length about 21 nm (~16 nm PEG and ~5 nm PHKRGD). Each arm of the 8-arm 20 kDa PEG can have one PHKRGD incorporated. The number of binders incorporated on each polymer and the arm length depend on the type of polymer, the molecular weight of polymer, and the type of binder. Such parameters affect the cell's sense of local nano-scale tensile forces and clustering. Typically, only a portion of the arms in the 8-arm polymer are linked to an adhesion ligand.

In some embodiments, one or more adhesion ligands can be included in the synthetic hydrogel, for example, a collagen-I derived peptide and/or a fibronectin derived peptide. Typically, each adhesion ligand has a concentration between about 0.1 mM and about 5 mM, between about 0.25 mM and about 3 mM, or between about 0.5 mM and about 3 mM, for example, about 1.5 mM. In some embodiments, two or more extracellular protein-binding peptides are included in the synthetic hydrogel, for example, a peptide having affinity to fibronectin (or "FN binder") and a peptide having affinity to collagen and laminin (or "BM binder"). Typically, each extracellular protein-binding peptide has a concentration between about 0.1 mM and about 1 mM, about 0.1 mM and about 0.5 mM, or about 0.25 mM and about 0.5 mM, for example, about 0.25 mM.

The molar ratio of the adhesion ligand to the ECM binder(s) (collective molar concentration if more than one type of ECM binder is present), is typically greater than 1:1, such as between about 1:1 and about 5:1, between about 1.2:1 and about 5:1, between about 1.5:1 and about 5:1, such as about 1.5:1, about 2:1, about 2.5:1, about 3:1, about 3.5:1, about 4:1, about 4.5:1, or about 5:1.

1. Adhesion Ligands

Adhesion ligands are typically synthetic peptides with affinity to cellular proteins, typically to cell adhesion molecules (CAMs). Cell adhesion molecules include integrins, immunoglobulin superfamily (IgSF) CAMS, cadherins, and selectins. The adhesion ligands may derive from proteins of the ECM. The adhesion ligands may be linear or branched. Preferably, the adhesion ligands have affinity to one or more integrins, and/or to one or more integrin subunits.

The adhesion ligands may have a secondary structure. The adhesion ligands may be peptides having a single chain amino acid sequence. The adhesion ligands may be branched peptides. The adhesion ligands may be peptides having a single chain amino acid sequence that self assembles into dimers, trimers, etc. The secondary structure of the dimers and trimers may be any secondary structure for proteins and peptides, including alpha helices, beta sheets, beta turns, or omega loops.

The adhesion ligands are typically functional at one end of the peptide to form a covalent or non-covalent bond with the polymer. Preferably, the adhesion ligands form a covalent bond with the polymer at one of the peptides.

a. Collagen

The adhesion ligands may include a motif from any one of fibrillar or non-fibrillar collage. The fibrillar collagen include collagen types I, II, III, V, XI. The non-fibrillar collagen includes FACIT (Fibril Associated Collagens with Interrupted Triple Helices); collagen types IX, XII, XIV, XIX, XXI; short chain type VIII, X; basement membrane (Type IV); multiplexin (Multiple Triple Helix domains with Interruptions) (Type XV, XVIII); MACIT (Membrane Associated Collagens with Interrupted Triple Helices) (Type XIII, XVII); and others (Type VI, VII) (Ricard-Blum, *Cold Spring Harb Perspect Biol*, 2011; 3:a004978).

Different tissues contain collagen of different type. For example, Type I is common in skin, tendon, vasculature, organs, bone (main component of the organic part of bone); Type II is most common in cartilage (main collagenous component of cartilage); Type III is most common in reticulate (main component of reticular fibers), commonly found alongside type I; Type IV is most common in basal lamina, the epithelium-secreted layer of the basement membrane; and Type V is most common on cell surfaces, hair, and placenta.

The collagen can be of any animal origin or human.

b. Fibronectin

Fibronectin typically exists as a protein dimer, consisting of two nearly identical polypeptide chains linked by a pair of C-terminal disulfide bonds. Each fibronectin subunit typically has a molecular weight of 230-250 kDa and contains three types of modules: type I, II, and III. All three modules are composed of two anti-parallel (3-sheets resulting in a Beta-sandwich; however, type I and type II are stabilized by intra-chain disulfide bonds, while type III modules do not contain any disulfide bonds. The absence of disulfide bonds in type III modules allows them to partially unfold under applied force.

Three regions of variable splicing occur along the length of the fibronectin protomer. One or both of the "extra" type III modules (EIIIA and EIIIB) may be present in cellular fibronectin, but they are never present in plasma fibronectin. A "variable" V-region exists between III14-15 (the 14th and 15th type III module). The V-region structure is different from the type I, II, and III modules, and its presence and length may vary. The V-region contains the binding site for α4β1 integrins. It is present in most cellular fibronectin, but only one of the two subunits in a plasma fibronectin dimer contains a V-region sequence.

The modules are arranged into several functional and protein-binding domains along the length of a fibronectin monomer. There are four fibronectin-binding domains, allowing fibronectin to associate with other fibronectin molecules. One of these fibronectin-binding domains, I1-5, is referred to as the "assembly domain", and it is required for the initiation of fibronectin matrix assembly. Modules III9-10 correspond to the "cell-binding domain" of fibronectin. The RGD sequence (Arg-Gly-Asp) is located in III10 and is the site of cell attachment via α5β1 and αVβ3 integrins on the cell surface. The "synergy site" is in III9 and has a role in modulating fibronectin's association with α5β1 integrins. Fibronectin also contains domains for fibrin-binding (I1-5, I10-12), collagen-binding (I6-9), fibulin-1-binding (III13-14), heparin-binding and syndecan-binding (III12-14) (Mao et al., *Matrix Biology*, 24:389-399).

c. Laminin

Laminin polyprotein includes fifteen laminin trimers. The laminins are combinations of different alpha-, beta-, and gamma-chains. The five forms of alpha-chains are: LAMA1, LAMA2, LAMA3 (which has three splice forms), LAMA4, LAMA5. The beta-chains include: LAMB1, LAMB2, LAMB3, LAMB4 (note that no known laminin trimer incorporates LAMB4 and its function remains poorly understood). The gamma-chains are: LAMC1, LAMC2, LAMC3. Laminins were previously numbered as they were discovered, i.e. laminin-1, laminin-2, laminin-3, etc., but the nomenclature was changed to describe which chains are present in each isoform (laminin-111, laminin-211, etc., Aumailley et al., *Matrix Biology*, 24:326-332 (2005)). This is summarized in Table 1.

TABLE 1

Laminin nomenclature and chain composition.

| Old nomenclature | Old synonyms | Chain composition | New nomenclature |
|---|---|---|---|
| Laminin-1 | EHS laminin | α1β1γ1 | Laminin-111 |
| Laminin-2 | Merosin | α2β1γ1 | Laminin-211 |
| Laminin-3 | S-laminin | α1β2γ1 | Laminin-121 |
| Laminin-4 | S-merosin | α2β2γ1 | Laminin-221 |
| Laminin-5/ Laminin-5A | Kalinin, epiligrin, nicein, ladsin | α3Aβ3γ2 | Laminin-332/Laminin-3A32 |
| Laminin-5B | | α3Bβ3γ2 | Laminin-3B32 |
| Laminin-6/ Laminin-6A | K-laminin | α3Aβ1γ1 | Laminin-311/Laminin-3A11 |
| Laminin-7/ Laminin-7A | KS-laminin | α3Aβ2γ1 | Laminin-321/Laminin-3A21 |
| Laminin-8 | | α4β1γ1 | Laminin-411 |
| Laminin-9 | | α4β2γ1 | Laminin-421 |
| Laminin-10 | *Drosophila*-like laminin | α5β1γ1 | Laminin-511 |
| Laminin-11 | | α5β2γ1 | Laminin-521 |
| Laminin-12 | | α2β1γ3 | Laminin-213 |
| Laminin-14 | | α4β2γ3 | Laminin-423 |
| | | α5β2γ2 | Laminin-522 |
| Laminin-15 | | α5β2γ3 | Laminin-523 | d. Integrins

Integrins are cell adhesion molecules and are obligate heterodimers with two subunits: α (alpha) and β (beta). Integrins in mammals have twenty-four α and nine β subunits (Tables 2 and 3). Beta-1 integrins interact with many alpha integrin chains. Tissue distribution of integrins is presented in Table 4.

Integrins work alongside other receptors such as cadherins, the immunoglobulin superfamily cell adhesion molecules, selectins and syndecans, to mediate cell-cell and cell-matrix interaction. Ligands for integrins include fibronectin, vitronectin, collagen and laminin.

TABLE 2

Integrin alpha subunits in mammals.

| gene | alpha (mammal) protein | synonyms |
|---|---|---|
| ITGA1 | CD49a | VLA1 |
| ITGA2 | CD49b | VLA2 |
| ITGA3 | CD49c | VLA3 |
| ITGA4 | CD49d | VLA4 |
| ITGA5 | CD49e | VLA5 |
| ITGA6 | CD49f | VLA6 |
| ITGA7 | ITGA7 | FLJ25220 |
| ITGA8 | ITGA8 | |
| ITGA9 | ITGA9 | RLC |
| ITGA10 | ITGA10 | |
| ITGA11 | ITGA11 | HsT18964 |
| ITGAD | CD11D | FLJ39841 |
| ITGAE | CD103 | HUMINAE |
| ITGAL | CD11a | LFA1A |
| ITGAM | CD11b | MAC-1 |

TABLE 2-continued

Integrin alpha subunits in mammals.

| gene | alpha (mammal) protein | synonyms |
|---|---|---|
| ITGAV | CD51 | VNRA, MSK8 |
| ITGA2B | CD41 | GPIIb |
| ITGAX | CD11c | |

TABLE 3

Integrin beta subunits in mammals.

| gene | beta (mammal) protein | synonyms |
|---|---|---|
| ITGB1 | CD29 | FNRB, MSK12, MDF2 |
| ITGB 2 | CD18 | LFA-1, MAC-1, MFI7 |
| ITGB3 | CD61 | GP3A, GPIIIa |
| ITGB4 | CD104 | |
| ITGB5 | ITGB5 | FLJ26658 |
| ITGB6 | ITGB6 | |
| ITGB7 | ITGB7 | |
| ITGB8 | ITGB8 | |

TABLE 4

Tissue distribution of integrins.

| Name | Synonyms | Distribution | Ligands |
|---|---|---|---|
| α1β1 | VLA-1 | Many | Collagens, laminins |
| α2β1 | VLA-2 | Many | Collagens, laminins |
| α3β1 | VLA-3 | Many | Laminin-5 |
| α4β1 | VLA-4 | Hematopoietic cells | Fibronectin, VCAM-1 |
| α5β1 | VLA-5; fibronectin receptor | widespread | fibronectin and proteinases |
| α6β1 | VLA-6; laminin receptor | widespread | laminins |
| α7β1 | | muscle, glioma | laminins |
| aLβ2 | LFA-1 | T-lymphocytes | ICAM-1, ICAM-2 |
| αMβ2 | Mac-1, CR3 | Neutrophils and monocytes | Serum proteins, ICAM-1 |
| αIIbβ3 | Fibrinogen receptor; gpIIbIIIa | Platelets | fibrinogen, fibronectin |
| αVβ1 | | ocular melanoma; neurological tumors | vitronectin; fibrinogen |
| αVβ3 | vitronectin receptor | activated endothelial cells, melanoma, glioblastoma | vitronectin, fibronectin, fibrinogen, osteopontin, Cy r61, thyroxine, TETRAC |
| αVβ5 | | widespread, esp. fibroblasts, epithelial cells | vitronectin and adenovirus |
| αVβ6 | | proliferating epithelia, esp. lung and mammary gland | fibronectin; TGFβ1 + 3 |
| αVβ8 | | neural tissue; peripheral nerve | fibronectin; TGFβ1 + 3 |
| α6β4 | | Epithelial cells | Laminin | e. Exemplary Adhesion Ligands

Exemplary adhesion ligands include "RGD," a fibronectin (FN)-derived adhesion peptide containing the canonical RGD motif from the 10th FN type III domain NH2-GCRE-RGDSP(Am); "PHSRN-K-RGD," a fibronectin-derived adhesion peptide containing both the RGD motif and the PHSRN synergy site from the 9th FN type III repeat in a branched configuration to mimic features of the biophysical presentation in FN, (Ac)PHSRNGGGK-(Ac)GGGERCG-GGRGDSPY(Am); "PHSRN-K-RDG," a scrambled control sequence where the RGD motif was scrambled reducing integrin binding; (Ac)PHSRNGGGK-GGGERCG(Ac)-GGRDGSPY(Am); "GFOGER," a collagen I-derived adhesion peptide, NH2-GGYGGGPG(GPP)SGFOGER(GPP)SGPC(Am), "Lam-5," a laminin 5-derived adhesion peptide, NH2-GCRG-PPFLMLLKGSTR(Am) (Lam5).

2. Extracellular Matrix Binders

Typically, the synthetic hydrogels include one or more extracellular matrix binders. The ECM includes components and/or a network of extracellular macromolecules, such as proteins, enzymes, and glycoproteins, that provide structural and biochemical support of surrounding cells. The extracellular matrix includes the interstitial matrix and the basement membrane. The components of the ECM include proteoglycans heparan sulfate, chondroitin sulfate, keratan sulfate; non-proteoglycan polysaccharide hyaluronic acid, and the proteins include collagen, elastin, fibronectin, and laminin.

Typically, the ECM binder, also referred to as the ECM protein binder or the ECM protein-binding peptide, is a synthetic peptide with affinity to ECM components and/or proteins. Therefore, the ECM protein binder may have an affinity to any or proteoglycans heparan sulfate, chondroitin sulfate, keratan sulfate; non-proteoglycan polysaccharide hyaluronic acid; the proteins collagen, elastin, fibronectin, and laminin, or the combination thereof.

Preferred ECM binders typically have affinity to fibronectin, collagen type IV, and/or laminin.

The ECM binders are typically functional at one end of the peptide to form a covalent or non-covalent bond with the polymer. Preferably, the ECM binders form a covalent bond with the polymer at one of the peptides.

a. Peptides Having Affinity to Fibronectin

Binders having affinity to fibronectin are referred to herein as FN binders, and include peptides (NH2-)-GCRE-TLQPVYEYMVGV(—COOH), and peptides, polypeptides, oligopeptides, or proteins containing the amino acid sequence GCRE, and/or TLQPVYEYMVGV.

Other exemplary FN binders include peptides with amino acid sequences

```
                                    (SEQ ID NO: 18)
VPQIHGQNKGNQSFEEDTE, (SEQ ID NO: 19)
VPQIQGQNKGNQSFEEDTE, (SEQ ID NO: 20)
VPQIHGQNNGNQSFEEDTE, (SEQ ID NO: 21)
VPQIQGQNNGNQSFEEDTE, (SEQ ID NO: 22)
VPQIHGQNIGNQSFEEDTE, (SEQ ID NO: 23)
VPQIQGQNIGNQSFEEDTE, (SEQ ID NO: 24)
VPQIAGQNKGNQSFEEDTE,
and (SEQ ID NO: 25)
VPQIAGQNAGNQSFEEDTE.
``` b. Peptides Having Affinity to Basement Membrane Proteins

Binders having affinity to basement membrane proteins are referred to herein as BM binders. The BM binders typically include synthetic peptides with affinity to one or more of the components of the basement membrane. Exemplary components of the basement membrane include laminin; integrins; nidogens; dystroglycans; collagen types III, IV, and VII; perlacan; heparan sulfate; and fibrillin. The BM binders may have affinity to collagen type IV and laminin.

BM binders include the peptide NH2-GCRE-ISAFLGIP-FAEPPMGPRRFLPPEPKKP(Am), and peptides, polypeptides, oligopeptides, or proteins containing the amino acid sequence GCRE, and/or ISAFLGIPFAEPPMGPRRFLP-PEPKKP(Am).

factor (βNGF), retinoic acid, interleukin (IL)-3, IL-6, IL-11, Noggin, platelet derived growth factor (PDGF), stem cell factor (SCF), vascular endothelial growth factor (VEGF), Wnt-1, Wnt-2, Wnt-1a, Wnt-5a, Wnt-7a, their variants and analogs. Variants and analogs may include the factor(s) with amino acid modifications, such as EGF with Y13G modification (Reddy et al., Nature Biotechnology, 14:1696-1699 (1996)).

TABLE 5

Exemplary binders for the synthetic hydrogels.

| Peptide Name | Peptide Amino Acid Sequence | Linear or Branched | Designation |
|---|---|---|---|
| RGD | NH2-GCRE-RGDSP(Am) | linear | Adhesion Ligand |
| PHSRN-K-RGD | (Ac)PHSRNGGGK-(Ac)GGGERCG-GGRGDSPY(Am) | branched | Adhesion Ligand |
| RDG | NH2-GCRE-RDGSP(Am) (SEQ ID NO: 13) | linear | Scrambled peptide |
| PHSRN-K-RDG | (Ac)PHSRNGGGK-GGGERCG(Ac)-GGRDGSPY(Am) | branched | Scrambled peptide |
| GFOGER | NH2-GGYGGGPG(GPP)5GFOGER(GPP)5GPC(Am) (SEQ ID NO: 15) | linear | Adhesion Ligand |
| Lam-5 | NH2-GCRG-PPFLMLLKGSTR(Am) (SEQ ID NO: 17) | linear | Adhesion Ligand |
| FN-binder | (NH2-)-GCRE-TLQPV YEYMVGV(—COOH) | linear | ECM Binder |
| BM-binder | NH2-GCRE-ISAFLGIPFAEPP MGPRRFLPPEPKKP(Am) | linear | ECM Binder |

All amine terminals were acetylated (Ac) and all carboxyl terminals were amidated (Am).

3. Second Linking Moiety

The binder typically contains a second linking moiety. The second linking moiety can be a reactive group that reacts with the first linking moiety of the biodegradable polymer to form a polymer-binder adduct. The second linking moiety can contain any suitable reactive groups described above. An exemplary second linking moiety is a thiol group. The thiol group is preferably a free thiol group at the terminus of the binders. For example, the binders are adhesion ligands and extracellular protein-binding peptides, where each peptide was synthesized to have a free thiol group at the N-terminus.

C. Additional Factors

The hydrogels may include additional factors, such as growth factors, their fragments, their variants and analogs. Typically, the additional factors are included to further support the growth and/or differentiating the cells in the enteroids. The additional factors natural or synthetic peptides and small molecule. The additional factors may be co-factors, signaling molecules, and growth factors, including, but not limited to basic fibroblast growth factor (bFGF), FGF-1, FGF-2, FGF-4, FGF-7, FGF-10, transforming growth factor β1 (TGF-β1), activin-A, activin-B, bone morphogenic protein 4 (BMP-4), hepatocyte growth factor (HGF), epidermal growth factor (EGF), β nerve growth See also Cambria, et al., Biomacromolecules 2015; 16(8): 2316-26.

D. Cross Linkers

Generally, the cross linkers include small molecules or peptides for linking the functionalized branches of the polymers together. In some aspects, the crosslinkers may link the peptides attached to the polymer branches to other peptides of other polymers' branches, or to other polymers' functionalized branches. Preferably, the crosslinkers link the functionalized branches of the polymers together.

The crosslinker typically includes two functional ends (bifunctional) for crosslinking. The crosslinkers may be bifunctional small molecules, bifunctional polymers, bifunctional peptides, bifunctional oligopeptides, or any other bifunctional crosslinker.

The synthetic peptide can contain a protease-, proteinase-, or transpeptidase-cleavable motif, for example, a motif cleavable by a matrix-metalloproteinase (MMP) and/or a Sortase A transpeptidase. The incorporation of cleavable motifs leads to dissolvable synthetic hydrogels. This allows for recovery of intact cells and cell-secreted metabolites from the hydrogels, which is an important limitation in MATRIGEL® supported organoid growth. Few exemplary crosslinkers are shown in Table 7.

The cross-linker typically contains a cross linking moiety that reacts with the first linking moiety on the biodegradable polymer to initiate cross linking. In some embodiments, the ratio of cross-linking moiety to first linking moiety is between 0.1 and 1, between 0.35 and 1, or between 0.5 and 1, for example, about 0.5. The synthetic hydrogel typically has a cross linking density between 10% and 90%, such as between about 20% and 80%, such as between about 20 and 70.

Exemplary crosslinking densities include about 10%, about 15%, about 20%, about 25%, about 30%, about 35%, about 40%, about 45%, about 50%, about 55%, about 60%, about 65%, about 70%, and about 75%.

The cross-linking density can be adjusted to alter the rate of degradation, the strength, or both, of the synthetic hydrogel. The cross-linking density can be adjusted by adjusting the proportion of the biodegradable polymers containing reactive groups in the polymers, adjusting the concentration of the cross linkers in the crosslinking reaction, changing the number of reactive arms in the biodegradable polymer, or combinations thereof. The cross-linking density can be determined for a crosslinked polymer using any means known in the art, such as the approach described in Wang, et al., *Nat. Biotechnol.*, 20(6):602-606 (2002).

1. Peptide Crosslinkers

The crosslinkers may be bifunctional peptide crosslinkers. The peptide crosslinkers may include a cleavable motif containing an amino acid sequence recognized by one or more proteolytic enzymes, such as proteases, proteinases, peptidases, and transpeptidases, such as protein sorting transpeptidases. The peptide crosslinkers with cleavable motifs may be useful for hydrogel dissolution. The dissolution may occur in the presence or absence of a competitive substrate or an acceptor substrate for the enzymes. The competitive substrate may be used to tune the dissolution reaction to a specific region of the hydrogel or slow the reaction time. The acceptor substrate may be used with transpeptidases to complete the cleaving of the crosslinker. Typically, the competitive substrate includes a peptide with an amino acid sequence substantially similar to the cleavable motif. The acceptor substrate may be any sequence of amino acids specific for the transpeptidase reaction, but typically includes at least one, at least two, at least three, at least four, or at least five glycine (G) residues at the N-terminus of the substrate.

The crosslinking peptides may include cleavable motifs specific to a variety of proteolytic enzymes. Preferably, the cleavable motifs are specific to proteinases and/or transpeptidases, such as matrix metalloproteinases and bacterial sortase transpeptidases.

a. Matrix-Metalloproteinase (MMP)-Cleavable Crosslinkers

In some embodiments, one or more peptide crosslinkers include a sequence cleavable by a protease, including, for example, endoproteases (e.g., serine proteases, cysteine proteases, aspartic acid proteases), and metalloproteases (e.g., matrix metalloproteases and A Disintegrin And Metalloproteinase (ADAM)). In some embodiments, the peptide crosslinkers include sequences cleavable by both proteases and transpeptidases. Typically, the sequences cleavable by both proteases and transpeptidases are different sequences. In preferred embodiments, the crosslinkers are peptide crosslinkers having cleavable motifs cleavable by a sortase, a metalloproteinase, or both by a sortase and a metalloproteinase.

Incorporation of the MMP substrate sequences encourages proper cell growth in a 3D hydrogel space by mimicking the ECM. Over time, cells produce proteases (e.g., MMPs) that locally degrade the MMP substrate crosslink, which allow the cells to spread or even migrate through the gels (Fonseca et al., *Prog. in Poly. Sci.* 39(12):2010-29, 2014).

b. Sortase Cleavable Crosslinkers

The peptide exchange process of transpeptidases is well characterized (Lupoli et al., *JACS* 133:10748-51, 2011), and substrate sequences (i.e., the recognition motif and acceptor substrate sequence) are well known, or readily identifiable. Some examples of transpeptidases include, but are not limited to, D-glutamyltransferase, peptidyltransferases, glutathione gamma-glutamyl cysteinyltransferase, gamma-glutamyltransferase, gamma-glutamylcyclotransferase, serine-type D-Ala-D-Ala carboxypeptidase, zinc D-Ala-D-Ala carboxypeptidase, glutathione hydrolase, and sortases including Sortase A, and Sortase B.

A notable aspect of SrtA-mediated reactions (and transpeptidases in general) is that the product formed can contain a sequence (e.g., LPRTGGG) that becomes itself a potential substrate (e.g., recognition motif). Using the reversibility of SAA-mediated reactions (Liu et al., J. Org. Chem. 79, 487-492 (2014)), gels could be formed and dissolved in minutes while preserving cell viability, thus opening up the possibility that a single relatively low-cost, broadly accessible reagent can be used to create and break down highly tailored synthetic ECM.

Sortases are transpeptidases found in Gram-positive bacteria that anchor surface proteins to the bacterial cell wall. Sortase A (SrtA) catalyzes a peptide exchange process of the general form: (R)-LPXTG+GGG-(R)=(R)-LPXTGGG-(R)+G. Three known, engineered variants of Sortase A (SrtA), derived from *Staphylococcus aureus*, offer dramatically improved catalytic rate constants and tailored substrate specificity compared to wild type SrtA (the sequences of SrtA and the variants can be found in Chen et al., *PNAS* 108, 11399-11404, 2011). SrtA and variants thereof are readily expressed in high yield as recombinant about 25 kDa proteins (Chen, I. et al., *PNAS* 108: 11399-11404 (2011); Popp and Ploegh, Angew. Chem. Int. Ed. 50, 5024-5032 (2011); Chan, L. et al., *PLoS ONE* 2, e1164 (2007)). Moreover, sortase variants that recognize non-overlapping substrate sequences (e.g., recognition motifs and acceptor substrate sequences) have been described (Don et al., *PNAS* 111(37): 13343-13348, 2014; Raeeszadeh-Sarmazdeh, et al., Colloids and Surfaces B: Biointerfaces 128:457-463, 2015).

SrtA-mediated crosslinking provides many advantages over existing enzyme-mediated crosslinking strategies, owing at least in part to its: (i) specificity, the small peptide substrates of SrtA are rare in mammalian proteins, thus crosslinking of cells by the enzyme is avoided; (ii) increased catalytic rates—engineered mutants of SrtA with 100× greater catalytic efficiencies and tailored substrate affinities compared to wild type are available; (iii) increased diffusion rates, SrtA is relatively small (25 kDa) relative to other crosslinking enzymes; and (iv) availability, SrtA mutants can easily be produced recombinantly in high yield.

Therefore, in some aspects, the peptide crosslinkers include at least a portion of a peptides having a recognition motif cleavable by a transpeptidase.

In some embodiments, the hydrogel includes gels formed as a result of e.g., norbornene-thiolene or Michael-type (vinyl sulfone) crosslinking chemistry, and peptide crosslinkers having a sortase cleavable motif.

Exemplary peptide crosslinkers with a transpeptidase cleavable motifs produce crosslinked hydrogels of a general formula polymer-LPRTGGG-polymer. Such gels may be readily degraded and dissolved in the presence of a transpeptidase and a peptide that includes a transpeptidase acceptor substrate sequence (e.g., sortase and $NH_2$-GGG). The peptide represented by LPRTGGG in this example can further include additional functional sequences, such as cleavable motifs used by other proteolytic enzymes.

c. Exemplary Peptide Crosslinkers

Exemplary peptide crosslinkers include a portion having the following sequences:

| | |
|---|---|
| LPXT | (SEQ ID NO: 27) |
| LPXTG | (SEQ ID NO: 6) |
| LPETG | (SEQ ID NO: 28) |
| LPXSG | (SEQ ID NO: 7) |
| LAXTG | (SEQ ID NO: 8) |
| LPRTG | (SEQ ID NO: 29) |
| LPRTGGG | (SEQ ID NO: 26) |
| GCRE-LPRTGGGK | (SEQ ID NO: 30) |
| GCRD-VPMS MRGG-DRCG | (SEQ ID NO: 31) |
| GCRD-LPRTGGPQGIWGQ-DRCG (named: LW-XL) | (SEQ ID NO: 32) |
| GCRD-LPRTGGPQGIAGQ-DRCG (named: LA-XL) | (SEQ ID NO: 33) |

Sortase A Catalysis

SrtA catalyzes a peptide exchange process of the general form: (R)-LPXTG+GGG-(R')=(R)-LPXTGGG-(R')+G. This transpeptidase reaction is now an established protein engineering tool, used to ligate large protein subdomains together or to link proteins with synthetic polymers. The reversibility of SrtA-mediated reactions, which is a shortcoming in most protein engineering applications, led to investigation whether SrtA mutants could be used to disassemble synthetic ECM crosslinked with defined peptides while preserving crucial extracellular signaling proteins. The SrtA transpeptidase reaction as implemented here involved an LPXTG motif embedded within the crosslink and an N-terminal glycine donor, soluble GGG, to effectively sever the crosslinks in a reaction that is highly selective, as very few mammalian proteins include the LPXTG motif.

The soluble peptide with one, two, three, four, five or more N-terminal glycine residues, used as donor, i.e., as acceptor substrate.

2. Cross-Linking Moieties

The cross linker typically contains a cross-linking moiety. The cross-linking moiety can be a reactive group that reacts with the first linking moiety of the biodegradable polymer to form the synthetic hydrogel. The cross-linking moiety can be any suitable reactive groups described above. An exemplary second linking moiety is a thiol group. The cross-linker are preferably dithiols with one thiol group at each terminus. For example, the cross-linkers are MMP and/or Sortase cleavable peptides, where each peptide was synthesized to have one free thiol group at each terminus.

E. Inhibitors

The inhibitors are typically apoptosis inhibitors. Apoptosis inhibitors include small molecules and peptides with known inhibitory effects on cellular apoptosis. The inhibitor may inhibit any stage of cellular apoptosis. Preferably, the inhibitor inhibits dissociation-induced apoptosis. Preferably, the inhibitors include inhibitors of the Rho kinase.

Inhibitors of apoptosis include compounds 10058-F4, 4'-Methoxyflavone, BI-6C9, BAX Inhibiting Peptide V5 (Val-Pro-Met-Leu-Lys (SEQ ID NO:34)), BTZO-1, Bongkrekic acid, CTP Inhibitor, and other suitable apoptosis inhibitors.

Inhibitors of Rho kinase (ROCK), including inhibitors of ROCK isoforms, ROCK1 and ROCK2, are preferred. Exemplary ROCK inhibitors include Y-27632, Y-27632 dihydrochloride, Y39983, Y-30141, GSK429286A, RKI-1447, netarsudil, ripasudil, fasudil, Wf-536, SLx-2119, DE-104, H-1152P, XD-4000, HMN-1152, BA-210, BA-207, BA-215, BA-285, BA-1037, Ki-23095, VAS-012, azabenzimidazole-aminofurazans, olefins, isoquinolines, indazoles, pyridinealkene derivatives, 4-(1-aminoalkyl)-n-(4-pyridyl) cyclohexane-carboxamides, rhostatin, quinazoline, and salts, prodrugs, and derivatives thereof.

Typically, the synthetic hydrogels incorporate the inhibitors at a concentration between about 0.01 µM and about 100 µM, such as between about 0.1 µM and about 100 µM, between about 1 µM and about 100 µM, between about 1 µM and about 75 µM, preferably between about 1 µM and about 50 µM, most preferably about 10 µM, prior to gelation of the hydrogel.

The inhibition may be complete or partial. Typically, the inhibitor reduces cellular apoptosis by at least about 50%, about 55%, about 60%, about 65%, about 70%, about 75%, about 80%, about 85%, about 90%, or about 95%. The reduction in apoptosis in a cell population may be compared to a control. The control may include the same type, or similar cells, grown under the same or similar conditions, in the absence of the inhibitor.

F. Cells, Tissues, and Organs

Typically, the synthetic hydrogels support attachment, growth, and differentiation of cells capable of forming tissues and organs. Suitable cells include tissue-resident stem cells, embryonic stem cells, pluripotent stem cells, induced pluripotent stem cells, which can self-organize in three-dimensional culture owing to their self-renewal and differentiation capacities. The synthetic hydrogels are suitable for encapsulating tissue-resident stem cells, tissue, embryonic stem cells, pluripotent cells, or induced pluripotent stem cells of mammalian and avian origin. Tissue-specific stem cells may be stem cells from the epithelial tissues, gastric tissues, intestinal tissues, endometrial tissues, cardiac tissues, vascular tissues, renal tissues, pulmonary tissues, immune cell interactions, neuronal tissues, osteochondral tissues, and muscle tissues.

Specifically, the synthetic hydrogels are suitable for organogenesis from human tissue-resident stem cells, tissue, embryonic stem cells, pluripotent cells, induced pluripotent stem cells. The synthetic hydrogels are also suitable for organogenesis from other mammalian or avian cells, such as cells from rodent, bovine, caprine, equine, ovine, porcine, or avian origin.

Generally, the cells in synthetic hydrogels form tissues and organs with differentiation, architecture, cellular composition and cellular organization characteristic of epithelial tissues, gastric tissues, intestinal tissues, endometrial tissues, cardiac tissues, vascular tissues, renal tissues, pulmonary tissues, immune cell interactions, neuronal tissues, osteochondral tissues, and muscle tissues.

The organoids formed in the synthetic hydrogels may be suitable for forming or studying the organs, tissues, and their interactions in the cardio-vascular system, renal system, pulmonary system, digestive system, immune system, nervous system, and/or musculoskeletal system.

G. Hydrogel Properties

As shown in the examples, the synthetic hydrogel supports human intestinal stem cell growth. The organoids formed in the synthetic hydrogel show correct polarity, undergo appropriate differentiation, and exhibit appropriate architecture and cellular composition. This is because the synthetic hydrogels are fully defined based on the microenvironmental properties and components governing the distinct stages of stem cell-driven organoid formation.

The biomechanical and biological properties of the synthetic hydrogels can be tuned by varying polymer structures, polymer molecular weight, and type of binder, to support organoid growth from different types of stem cells, normal or tumor-derived. For example, synthetic hydrogels formed from 8-arm polyethylene glycol (PEG) with 20 kDa or 40 kDa, integrin binding peptides, FN binders, BM binders, and peptides cleavable by MMP and Sortase support human intestinal stem cell growth.

The biomechanical properties of the synthetic hydrogels can be measured using relevant features, such as storage modulus, swelling, and pore size. Storage modulus is an indication of hydrogel's ability to store deformation energy in an elastic manner. Storage modulus is directly related to the extent of cross-linking, i.e. the higher the degree of cross-linking, the greater the storage modulus. In some embodiments, the synthetic hydrogel has a storage modulus between about 50 Pa and about 2000 Pa, such as between about 50 Pa and about 1800 Pa, between about 50 Pa and about 1500 Pa, between about 50 Pa and 1000 Pa, between about 500 and about 2000 Pa, between about 600 and about 1200 Pa, between about 700 and about 1000 Pa, or between about 600 and about 1050 Pa. The storage modulus can be tuned by varying the polymer structure, polymer molecular weight, and/or type of binders.

Swelling is directly related to the degree of cross-linking, i.e. the more cross-linking, the more swelling is restricted. In some embodiments, the synthetic hydrogel exhibits a swelling ratio (the ratio of gel volume after swelling to the volume of the hydrogel right after cross-linking) of less than or about 500%, less than or about 400%, less than or about 300%, less than or about 250%, less than or about 200%, less than or about 190%, or less than or about 180% when exposed to a fluid.

In some embodiments, the mean pore size of the synthetic hydrogels can be between about 10 nm and about 1 μm, between about 15 nm and about 500 nm, between about 15 nm and about 100 nm, between about 15 nm and about 50 nm, or between about 15 nm and about 35 nm.

For example, different biomechanical properties (i.e. storage modulus, swelling, and pore size) was determined with PEG of various molecular weight incorporated with different integrin binding peptides (Table 6).

1. Advantages of the Synthetic Hydrogels

Advantages of the synthetic hydrogels include high cell viability comparable to other gel types; usefulness with human and mouse stem cells; usefulness with intestinal stem cells from various regions of the same organ; allows incorporating other cell types (intestinal myofibroblast, immune cells, etc.), non-proteolytic synthesis and breakdown; mechanically robust and easy to tailor to a desired tissue organogenesis; and inexpensive and broadly accessible.

III. Methods of Making the Synthetic Hydrogels

Methods for forming the synthetic hydrogels are also provided. The formulation methods are highly tailorable and thus can be applied to various biodegradable polymers, binders, and cross linkers. The reactions are performed under cell-compatible conditions. Cell-compatible reactions refer to reactions which are not significantly toxic to living tissue and/or cells. Exemplary cell-compatible reactions include, but are not limited to reactions via thrombin-activated Factor XIIIa under physiological conditions or by another enzymatic addition mechanism known in the art, via Michael addition or click chemistry, or by another mild chemical addition mechanism known in the art.

Physiological conditions refer to a temperature range of 20-40° C., atmospheric pressure of 1, pH of 6-8. For example, the reactions can be performed at a temperature of 37° C., atmospheric pressure of 1, and pH about 7.4. Typically, the hydrogel can be formed in about 60 min, 40 min, 30 min, 20 min, 10 min, 5 min, 2 min, or 1 min.

A. Polymer-Binder Adduct Preparation

Typically, the method of forming synthetic hydrogel includes (i) combining a plurality of biodegradable polymers and one or more binders. The biodegradable polymer contains a first linking moiety. The first linking moiety may locate in the interior position of the polymer or near or at the terminal positions of the arm of the polymer. The number of first linking moiety on a polymer can be varied. For example, multiple first linking moieties may be included in one polymer. In some embodiments, the first linking moiety of the polymers can be an electrophilic and/or nucleophilic reactive group. The binder contains a second linking moiety. The second linking moiety can be a reactive group that reacts with the first linking moiety to form a polymer-binder adduct. For example, when the biodegradable polymers contain an electrophilic group, the second linking moiety can be a nucleophilic group. When the biodegradable polymers contain a nucleophilic group, the second linking moiety can be an electrophilic group. Any electrophilic and nucleophilic groups disclosed above can be used. In preferred embodiments, the biodegradable polymers can contain vinyl sulfone groups and the binders can contain free thiol groups at the terminus location. Each polymer may have at least one binder incorporated, for example, 1 or 3 binders incorporated. The incorporated binders may be on the same arm of the biodegradable polymer or different arms of the biodegradable polymer. Preferably, the binders are incorporated to the terminus of the arm of the biodegradable polymer.

In some embodiments, the synthetic hydrogel contains a weight/volume percentage of polymers between 1% and 50%, between 2% and 25%, or between 2% and 10%, for example, about 2%, about 3%, about 4%, or about 5%. The binders typically contain adhesion ligands and extracellular protein-binding peptides. The adhesion ligands may include one or more types of integrin-binding peptides, such as peptide derived from Collagen Type I and/or peptides derived from Fibronectin. Each type of adhesion ligand can have a concentration between 0.1 and 5 mM, between 0.25 and 3 mM, or between 0.5 and 3 mM, for example, about 1.5 mM. In some embodiments, two or more extracellular protein-binding peptides are included in the synthetic hydrogel, for example, a peptide having affinity to fibronectin (or "FN binder") and a peptide having affinity to collagen and laminin (or "BM binder"). Typically, each extracellular protein-binding peptide has a concentration between 0.1 and 1 mM, 0.1 and 0.5 mM, or 0.25 and 0.5 mM, for example, about 0.25 mM.

The molar ratio of the adhesion ligand to the ECM binder(s) (collective molar concentration if more than one type of ECM binder is present), is typically greater than 1:1, such as between about 1:1 and about 5:1, between about 1.2:1 and about 5:1, between about 1.5:1 and about 5:1, such as about 1.5:1, about 2:1, about 2.5:1, about 3:1, about 3.5:1, about 4:1, about 4.5:1, or about 5:1.

B. Crosslinking

The method can additionally include (ii) combining the adduct of step (i) and one or more cross-linkers, wherein the cross-linkers have a crosslinking moiety. The cross-linker preferably has two crosslinking moieties at each terminus. The crosslinking moieties can react with the first linking moieties on the biodegradable polymers to perform cross-linking and form hydrogel. For example, when the biodegradable polymers contain an electrophilic group, the crosslinking moiety can be a nucleophilic group. When the biodegradable polymers contain a nucleophilic group, the crosslinking moiety can be an electrophilic group. In preferred embodiments, the biodegradable polymers contain vinyl sulfone and the cross-linkers are dithiols having one thiol group at each terminus. In some embodiments, the ratio of crosslinking moiety to first linking moiety is between 0.1 and 1, between 0.35 and 1, or between 0.5 and 1, for example, about 0.5. In preferred embodiments, the ratio of thiol of cross linkers to vinyl sulfone of polymers is between 0.1 and 1, between 0.35 and 1, or between 0.5 and 1, for example, about 0.5.

Crosslinking can be performed either between different biodegradable polymers or between the biodegradable polymer/polymer-binder adducts and cross-linkers. Exemplary crosslinking reactions that are cell-compatible include, but are not limited to, reactions via thrombin-activated Factor XIIIa under physiological conditions or by another enzymatic crosslinking mechanism known in the art, or via Michael addition, click chemistry, or by another mild chemical crosslinking mechanism known in the art.

In preferred embodiments, the crosslinking is performed between the biodegradable polymer-binder adducts and crosslinkers. To achieve crosslinking between the biodegradable polymers and cross-linkers by the preferred Michael addition, one or more biodegradable polymers are functionalized with an electrophilic group and/or a nucleophilic group, whereas the crosslinkers carry a crosslinking moiety that reacts with the electrophilic group and/or nucleophilic group on the polymers. For example, the biodegradable polymers are modified with an electrophilic group, such as a vinyl sulfone, whereas the crosslinkers carry a nucleophilic group, such as a thiol group. In some embodiments, crosslinking is achieved via FXIIIa-mediated crosslinking between the biodegradable polymers and cross-linkers. For example, one or more biodegradable polymers are functionalized with a lysine-bearing peptide sequence, whereas the crosslinkers include a glutamine-bearing peptide sequence. In some embodiments, crosslinking is performed via click chemistry. For example, one or more biodegradable polymer in the plurality of biodegradable polymers is functionalized with a norbornene or thiolene group, whereas cross-linkers contain a thiolene or norbornene group.

Alternatively, or additionally, the crosslinking may be performed between biodegradable polymers. For example, to achieve crosslinking between different biodegradable polymers by the preferred Michael addition, at least one biodegradable polymer in the plurality of biodegradable polymers is functionalized with an electrophilic group, such as a vinyl sulfone or maleimide group, whereas at least another biodegradable polymer in the plurality of biodegradable polymers is functionalized with a nucleophilic group, such as a thiol group. In some embodiments, crosslinking is achieved via FXIIIa-mediated crosslinking between different biodegradable polymers, at least one biodegradable polymer in the plurality of biodegradable polymers is functionalized with a lysine-bearing peptide sequence, whereas at least another biodegradable polymer in the plurality of biodegradable polymers is functionalized with a glutamine-bearing peptide sequence. In some embodiments, crosslinking is performed via click chemistry, e.g. norbornene/thiolene click chemistry. At least one biodegradable polymer in the plurality of biodegradable polymers is functionalized with a norbornene group, whereas at least another biodegradable polymer in the plurality of biodegradable polymers is functionalized with a thiolene.

C. Combining Cells and Inhibitors

In some embodiments, the method additionally include (ia) combining cells, one or more inhibitors of dissociation-induced apoptosis, and the adduct of the first step. The incorporation of inhibitors is important for preventing death of encapsulated cells, especially for human organoid culture. In some embodiments, the inhibitor is at a concentration between 1 nM and 1 mM, between 10 nM and 100 µM, or between 100 nM and 50 µM, for example, about 10 µM. Cross-linking of the hydrogel is preferably performed in the presence of cells to be cultured within the hydrogel. This way the cells or cell aggregates are encapsulated by the formed hydrogel matrix, i.e. are residing in a distinct cell culture microenvironment. Alternatively, the cells and inhibitors of dissociation-induced apoptosis can be combined with the product of the second step.

The cells are typically incorporated at a cell density between about $1 \times 10^5$ cells/ml and about $1 \times 10^9$ cells/ml as the final density in the polymer-binder-crosslinker solution. Exemplary suitable ranges for the cell density in the final solution include between about $1 \times 10^5$ cells/ml and about $1 \times 10^8$ cells/ml, between about $5 \times 10^5$ cells/ml and about $5 \times 10^8$ cells/ml, between about $5 \times 10^5$ cells/ml and about $1 \times 10^8$ cells/ml, preferably between about $1 \times 10^6$ cells/ml and about $1 \times 10^8$ cells/ml, more preferably between about $1 \times 10^6$ cells/ml and about $1 \times 10^7$ cells/ml.

IV. Methods of Using the Synthetic Hydrogels

The synthetic hydrogels are suitable for organoid formation and organogenesis, drug discovery, inter-organ interaction characterization, and multi-organ drug responses. The synthetic hydrogels are particularly suitable for supporting organoid formation and organogenesis from human cells.

Through a semi-empirical approach, the biomechanical properties of the hydrogels can be tailored to support stem cell proliferation from various organs, or regions of organs. The examples below show the growth of stem cells from various regions of the gastrointestinal track, from mouse and human origin, in synthetic hydrogels. The possibility of growing stem cell from mouse and human make the synthetic hydrogels useful to a broader intestinal organoid community.

The synthetic hydrogels are also useful in drug discovery. The examples show that organoids emerging in the synthetic hydrogels respond to drug stimulation to a similar extent as organoids emerging in MATRIGEL®

A. Exemplary Method for Cell Encapsulation

The cells are typically incorporated into a mix of polymers functionalized and bound to the binders. Typically, the cells are incorporated in the presence of an apoptosis inhibitor. The cells may be at any suitable density and are not harmed by the subsequent crosslinking step. The crosslinking step occurs at physiological conditions, e.g, at about neutral pH, and 37° C.

An exemplary method includes the following steps. Hydrogels may be fabricated on top of the membrane of TRANSWELL® inserts (Corning) using Michael-type reaction chemistry. The functionalized polymer PEG-VS, e.g. an 8-arm PEG-VS (1.4 mM) is reacted with free thiols (—SH) on adhesion ligands and/or ECM binders PBS with 1 M HEPES (pH 7.8) for about 30 minutes. Immediately after the functionalization reaction, the solution is mixed with a cell suspension ($4.2\times10^7$ cells per mL in serum-free DMEM/F12, 1% penicillin/streptomycin). The solution is then reacted with the cysteine thiol (—SH) groups on the bifunctional peptide crosslinker, e.g., MMP-CL crosslinker (having a sequence: (Ac)GCRD-GPQGIAGQ-DRCG(Am) (SEQ ID NO:9)).

An exemplary organoid formation may be initiated by incorporating stem cells in a hydrogel and spreading the cells in the TRANSWELL® system as follows.

The concentration of cells in the crosslinking solution may be about $4.2\times10^6$ cell per mL (about 50,000 cells in 12 mL). The hydrogel gelation, as determined by the point at which the solution could no longer be pipetted, may occur over approximately 8 minutes (pH 7.8) after crosslinker addition, but may vary between 8 and 12 minutes depending on the specific hydrogel formulation. The hydrogel solution is typically pipetted for 2 minutes to keep stromal cells in suspension, allowed to sit in tube for 3-7 minutes (where wait time=gelation time−5 minutes), then transferred to inserts (12 mL per insert), manually spread with a pipette tip, then centrifuged for 4 minutes at (330 rcf in an Eppendorf centrifuge 5810) to ensure gelation occurred in the middle of centrifugation creating a flat, meniscus-free hydrogel on top of the cell culture inserts. Plates may then be incubated an additional 10 minutes at RT to allow crosslinking to proceed to completion.

After gelation is complete, growth media, such as DMEM/F12/FBS, may be added to the apical (top) (100 µL) and basolateral (bottom) (600 µL) sides of the TRANSWELL® to achieve hydrostatic equilibrium. Cultures are typically maintained in a humidified incubator at 37° C., 95% air, 5% $CO_2$.

B. Hydrogel Dissolution

The synthetic hydrogels with organoids are formed of materials permitting direct assaying of the organoids without the need to remove the hydrogel components. The synthetic hydrogels with organoids may be subject to dissolution to remove a portion, or substantially all of the components of the hydrogel.

The removal of hydrogel components occurs through hydrogel dissolution. Hydrogel dissolution includes incubating the synthetic hydrogels with organoids in the presence of dissolution agents. Typically, the incubation is for at least about 5 min, about 10 min, about 15 min, about 20 min, about 25 min, about 30 min, about 35 min, about 40 min, about 45 min, about 50 min, about 55 min, or about 60 min. In preferred embodiments, the dissolution is complete within about 10 min, about 15 min, about 20 min, about 25 min, about 30 min, about 35 min, about 40 min, about 45 min. Typically, the incubation occurs at physiological conditions, such as 37° C., 5% $CO_2$, humidified atmosphere, and includes growth media used to support organoid formation.

1. Dissolution Agents

Dissolution agents typically include enzymes, such as proteolytic enzymes, as well as competitive substrates and acceptor substrates. The dissolution agents include enzymes such as proteases, proteinases, peptidases, and transpeptidases, such as protein sorting transpeptidases, and combinations thereof.

The dissolution agents may be in a solution form at a concentration between about 0.01 µM and about 100 µM, such as between about 0.1 µM and about 100 µM, between about 1 µM and about 100 µM, between about 1 µM and about 75 µM, preferably between about 1 µM and about 50 µM, most preferably about 10 µM, about 30 µM, about 50 µM. Competitive substrates and/or acceptor substrates may be used at similar concentrations, and may be added together with the enzyme(s), or after the addition of the enzyme(s).

V. Kits

Kits including the components of the hydrogel are also provided. The kits may include every component of the hydrogel in a separate container, or a combination of components in the same container. The kits may also provide the cells to be encapsulated. The kits are typically provided with instructions for preparing the hydrogels and encapsulating cells.

The components of the hydrogels provided in the kit may be any one, or a combination of, the polymer(s), the binders, cross-linker(s), inhibitor(s), dissolution agent(s), and cells.

The present invention will be further understood by reference to the following non-limiting examples.

EXAMPLES

Example 1. Identification of Components for Synthetic Hydrogels

Figure 1B:
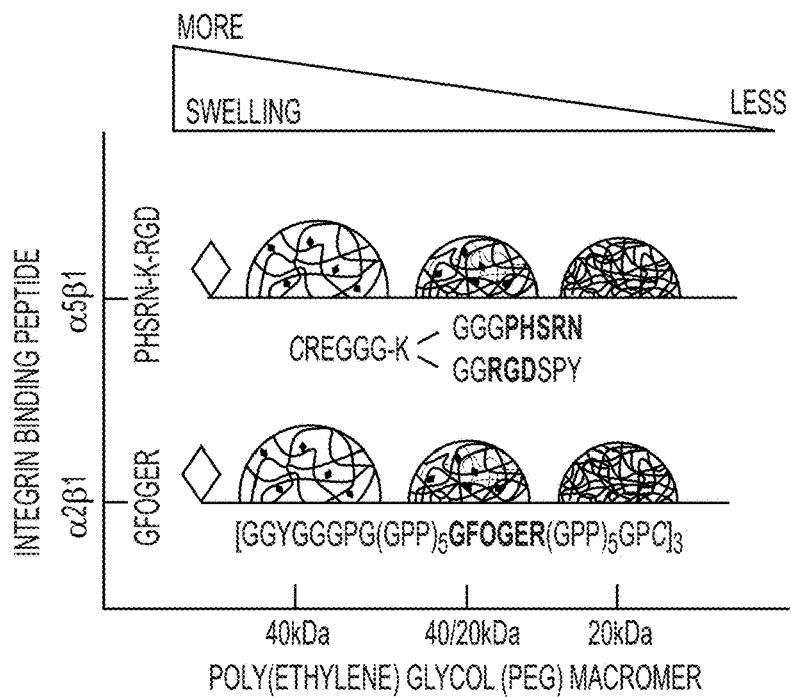

Integrin expression in tissue of origin/niche was identified. Integrin binding peptide was selected to create tunable synthetic hydrogels (FIGS. 1A-1B)

Multi-arm polyethylene glycol (PEG) polymers of various molecular weights, small peptides, and inhibitors were identified as the components formulating the synthetic hydrogels. Specifically, 20 kDa 8-arm PEG, 40 kDa 8-arm PEG, or a combination of both were identified for forming PEG hydrogels. The PEG arms were functionalized with vinyl sulfone (VS) groups.

Integrin binding peptides derived from collagen type I (containing the sequence GFOGER (SEQ ID NO:1)) and fibronectin (containing the sequence PHSRN (SEQ ID NO:2)) were selected for cell adhesion. The peptide derived from collagen type I has high affinity for integrin $\alpha_2\beta_1$, $\alpha_1\beta_1$, $\alpha_{10}\beta_1$, and $\alpha_{11}\beta_1$. The peptide derived from fibronectin has high affinity for integrin $\alpha_v\beta_3$ and moderate affinity for integrin $\alpha_5\beta_1$. The integrin binding peptides were synthesized to contain a free thiol group at the N-terminus. The collagen type I- and fibronectin-derived adhesion peptides can be used individually or in combination in the hydrogel formulation.

ECM binding peptides having affinity for secreted collagen and laminin ("BM binders") ($NH_2$-GCRE-ISAFLGIP-FAEPPMGPRRFLPPEPKKP(Am) (SEQ ID NO:4)), and fibronectin ("FN binders") (($NH_2$-GCRE-TLQPVY-EYMVGV-COOH) (SEQ ID NO:5)), were selected. These extracellular protein binding peptides were designed to capture fibronectin produced by endometrial stromal fibroblasts throughout the cycle and both laminin and type IV collagen basement membrane proteins that are normally produced by the epithelium during all menstrual cycle stages and locally produced and accumulated in the pericellular region of hormonally responsive fibroblasts in the stroma (Cook, et al., *Integrative Biology*, 9:271-289 (2017)). The extracellular protein binding peptides were synthesized to contain a free thiol group at the N-terminus.

Peptides that are cleavable by a matrix-metalloproteinase (MMP) ((Ac)GCRD-GPQGIAGQ-DRCG(Am) (SEQ ID NO:9)) or Sortase A transpeptidase (Sortase) are identified as crosslinkers to form the final cross-linked hydrogels. Alternatively, peptides that are cleavable by both MMP and Sortase are used as crosslinkers. The incorporation of MMP cleavable peptides leads to dissolvable hydrogels, allowing for recovery of intact cells and cell-secreted metabolites from the hydrogels.

A ROCK inhibitor was included in the hydrogel formulation. The ROCK inhibitor inhibits dissociation-induced apoptosis, thereby prevents cell death of encapsulated cells. This is necessary for human organogenesis.

Example 2. Assembly of Synthetic Hydrogels with Tunable Biomechanical Properties

Materials and Methods

Assembly of Synthetic Hydrogels

The PEG polymer arms were functionalized with vinyl sulfone groups (purchased from JenKem Technology, Beijing). The integrin-binding peptides and extracellular protein binding peptides were synthesized to contain a free thiol group at the N-terminus. The crosslinkers are dithiols with one thiol group at each terminus. The PEG hydrogels (3.5-10%, weight/volume) were assembled via sequential Michael-type addition reactions between the vinyl sulfone groups on the PEG polymer arms and the terminal thiol groups of the integrin binding peptides (0.25-3 mM) and extracellular protein binding peptides (0.25-0.5 mM) (FIG. 1D). Cells and ROCK inhibitors were then mixed with the peptide-PEG polymer adducts. The peptide-PEG polymer adducts were crosslinked with crosslinkers (thiol of cross linker:VS, 0.35-1), such as dithiol-MMP cleavable peptides (FIG. 1D-E). The PEG hydrogels are fully assembled after 30 minutes at pH 7.4 at 37° C. The Michael type addition reaction occurs at physiological conditions thus cells are not under stress during cell-encapsulation.

Tuning the Biomechanical Properties of Synthetic Hydrogels

Figure 1C:
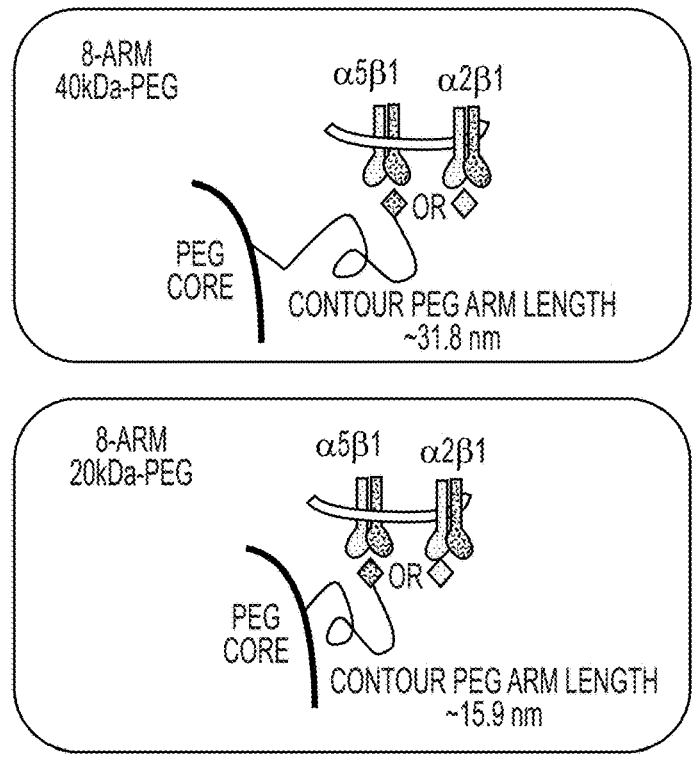
Figure 1D:
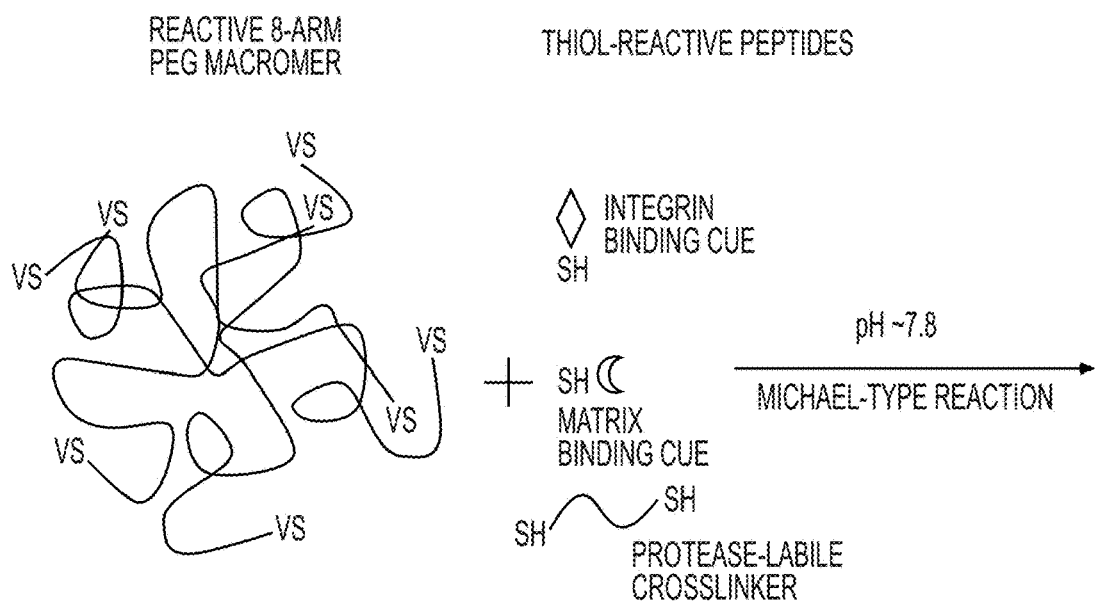
Figure 1E:
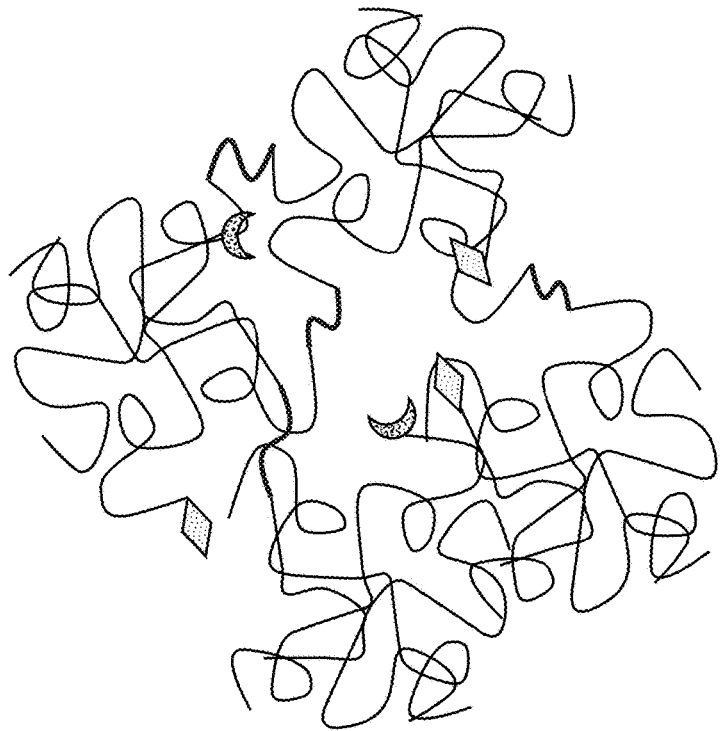

A semi-empirical approach was applied to tailor the biomechanical properties of the hydrogels to support stem cell proliferation (FIGS. 1B-1C). Briefly, organoid growth was evaluated with different hydrogel and media formulations. Organoid localization and quantification was performed using deep convolutional neural network (OR-GAQUANT™). ORGAQUANT™ performs in parallel experiments on a 96-well plate assay for organoid size quantification.

Results

PEG hydrogels were formulated with PEG polymers of various molecular weights (i.e. 20 kDa and 40 kDa at a ratio of 1:1) at different weight/volume percentages (3.5-10%), integrin binding peptides (0.25-3 mM) and extracellular protein binding peptides (0.25-0.5 mM) at different concentrations, and crosslinkers at different thiol:VS ratios (0.35-1). The biomechanical properties of the hydrogels were fine-tuned to achieve desired biological response.

Figure 1F:
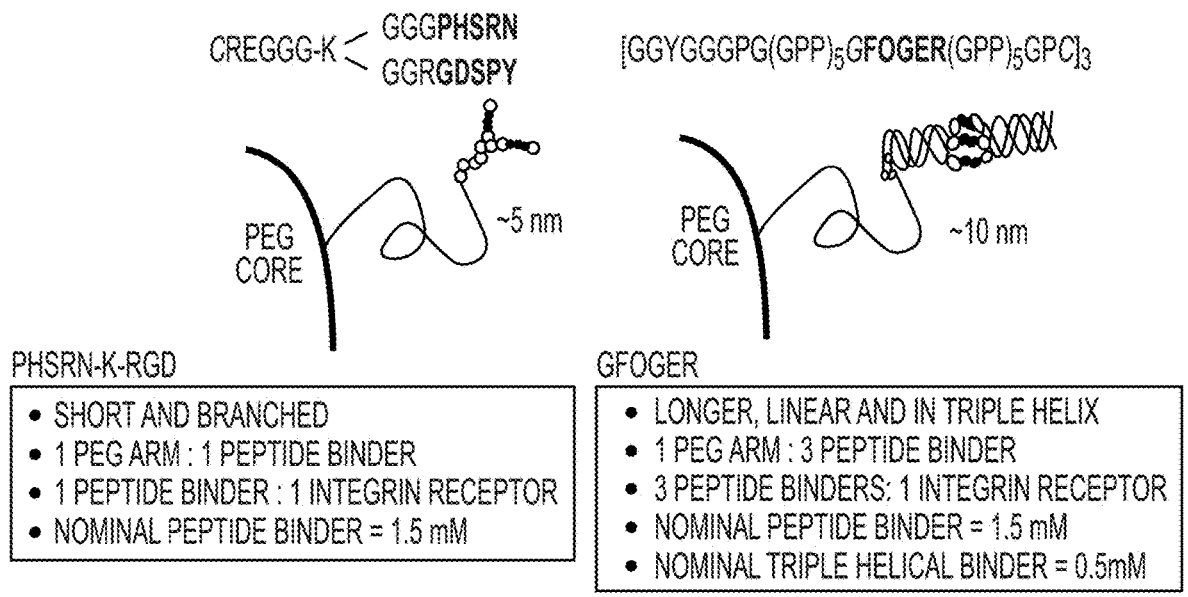

The mechanical properties of the hydrogels are affected by polymer identity (multi-arm/linear), polymer molecular weight, and crosslinking density. For example, the adduct of 20 kDa, 8-arm PEG polymer and peptide sequence derived from collagen type I (GFOGER (SEQ ID NO:1)) has three peptides per polymer with an arm length of about 26 nm measured from the PEG backbone to the P-terminus of the peptide (FIG. 1F). The adduct of 20 kDa, 8-arm PEG polymer and peptide sequence derived from fibronectin (PHKRGD) has one peptide per polymer with an arm length of about 21 nm measured from the PEG backbone to the P-terminus of the peptide (FIG. 1F). This difference affects the cell's sense of local nano-scale tensile forces and clustering. The biological properties of the hydrogels are affected by integrin binding peptides, extracellular protein binding peptides, and cross linker identity.

Table 6 compares the biomechanical properties of hydrogels formulated with 5% (weight/volume) PEG of various molecular weight, 1.5 mM integrin binding peptides, 0.25 mM each type of ECM protein binding peptides (i.e. 0.25 mM BM binders and 0.25 FN binders), and crosslinkers thiol:VS at 0.5.

TABLE 6

Biomechanical Properties of Hydrogels

| Relevant Feature | PEG-PHKRGD 1:0.5 VS:Thiol | | | PEG-GFOGER series | | |
| --- | --- | --- | --- | --- | --- | --- |
|  | 40 kDa | 40/20 kDa | 20 kDa | 40 kDa | 40/20 kDa | 20 kDa |
| Storage Modulus (Pa) | $620 \pm 20^{a}$ | $714 \pm 29^{ab}$ | $817 \pm 63^{bc}$ | $696 \pm 53^{ab}$ | $1034 \pm 21^{d}$ | $929 \pm 61^{cd}$ |
| Swelling (%) | $224 \pm 4^{ab}$ | $195 \pm 5^{bc}$ | $169 \pm 6^{c}$ | $296 \pm 18^{a}$ | $185 \pm 5^{bc}$ | $196 \pm 12^{bc}$ |
| Pore Size (nm) | $30 \pm 0.2^{a}$ | $23 \pm 0.5^{b}$ | $17 \pm 0.5^{c}$ | $33 \pm 1.2^{a}$ | $22 \pm 0.7^{b}$ | $21 \pm 1.5^{bc}$ |

$^{a}$Note =
Values with the same letter are statistically similar

Example 3. Synthetic Hydrogels Support Organoid Growth

Materials and Methods

Human intestinal stem cells were obtained from multiple donors. Cell cultures on hydrogels follow procedures previously reported (Cook, et al., *Integrative Biology*, 9:271-289 (2017)). Organoid growth was monitored using microscope. Human and mouse epithelial cell organoids were cultured on the hydrogels formulated according to Examples 1 and 2.

Figure 8A:
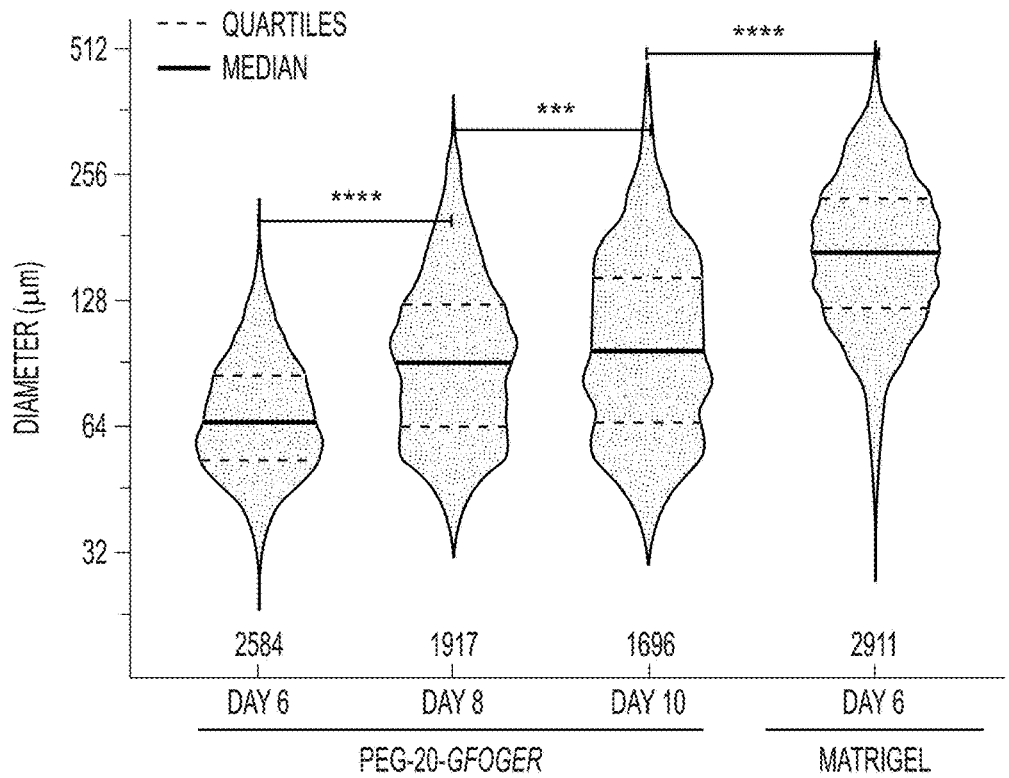
FIGS. 8A-8C are graphs showing single cell proliferation and enteroid formation in the PEG-20-GFOGER are similar to those in MATRIGEL®. Images of enteroids emerging from single cells in PEG-20-GFOGER hydrogels made at 0.5 mM GFOGERth, 0.25 mM BM-binder, 0.25 mM FN-binder and 50% XL-MMP-SrtA crosslinker were taken and quantified. Time-course enteroid diameter (μm, n=2 experiments) in the hydrogels is shown in FIG. 8A. The number of enteroids measured is depicted under each violin plot. The data was analysed using Kruskal-Wallis multiple comparison of the mean ranks. *P=0.0005,P<0.0001.
Figure 8B:
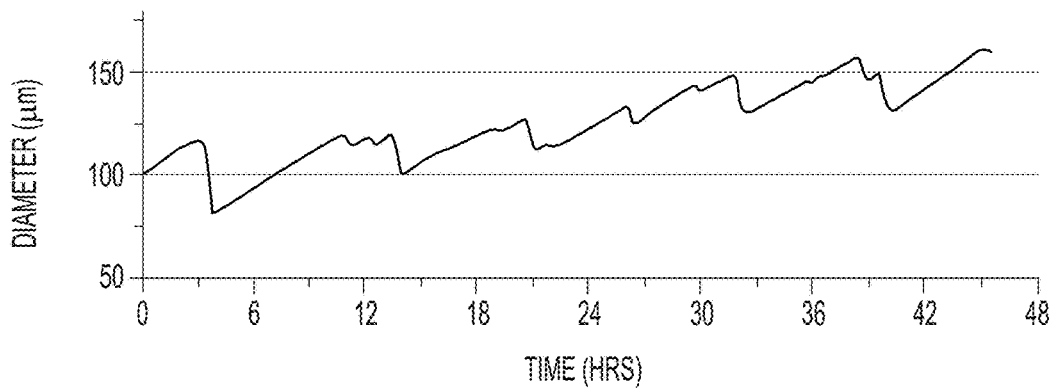
Figure 8C:
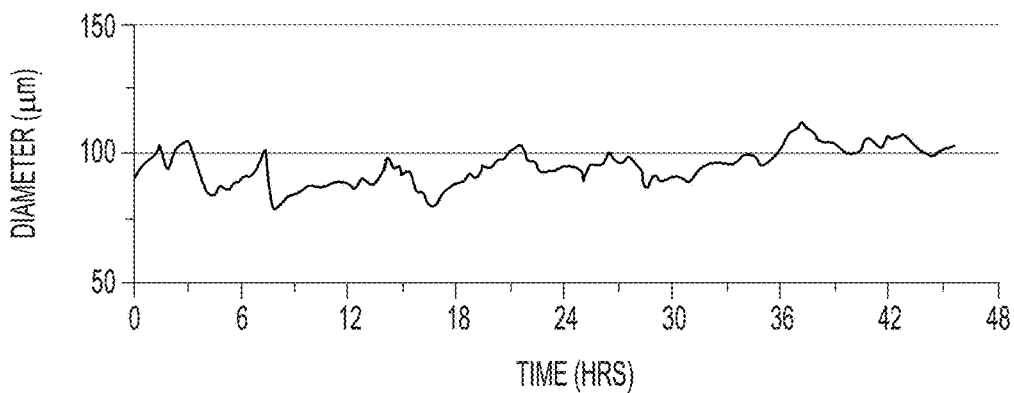
Figure 8D:
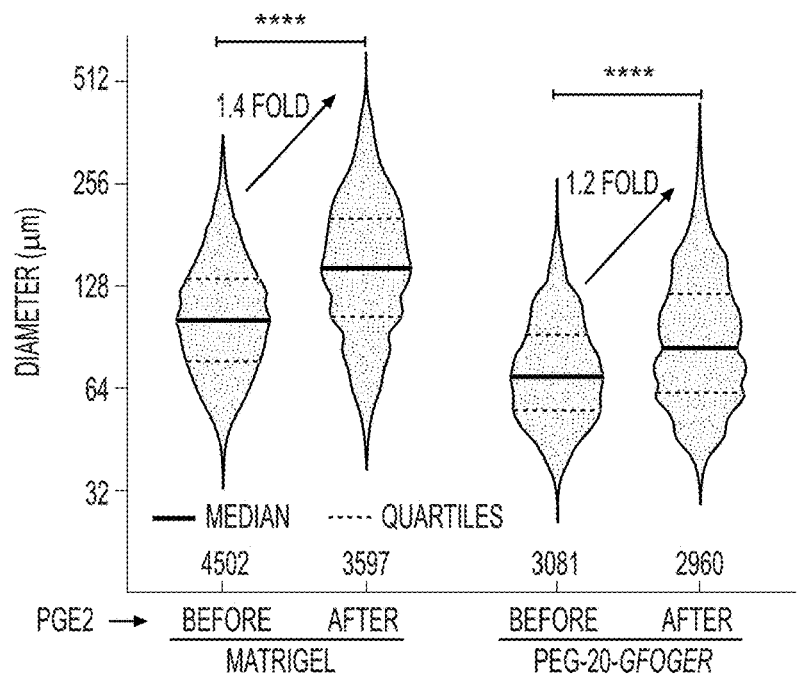
FIGS. 8D and 8E are graphs showing enteroid diameter before and after stimulation with prostaglandin E2 (PGE$_2$, n=3 independent experiments, FIG. 8D) and forskolin (FKL, n=2 independent experiments, FIG. 8E). The number of enteroids measured is depicted under each violin plot. The data was analysed using Mann-Whitney two-tailed comparison of the mean ranks. **P<0.0001. All PEG-20-GFOGER hydrogels were made at nominal concentrations of 0.5 mM GFOGERth, 0.25 mM BM-, and 0.25 mM FN-binder at 50% XL-MMP-SrtA crosslinker.
Figure 8E:
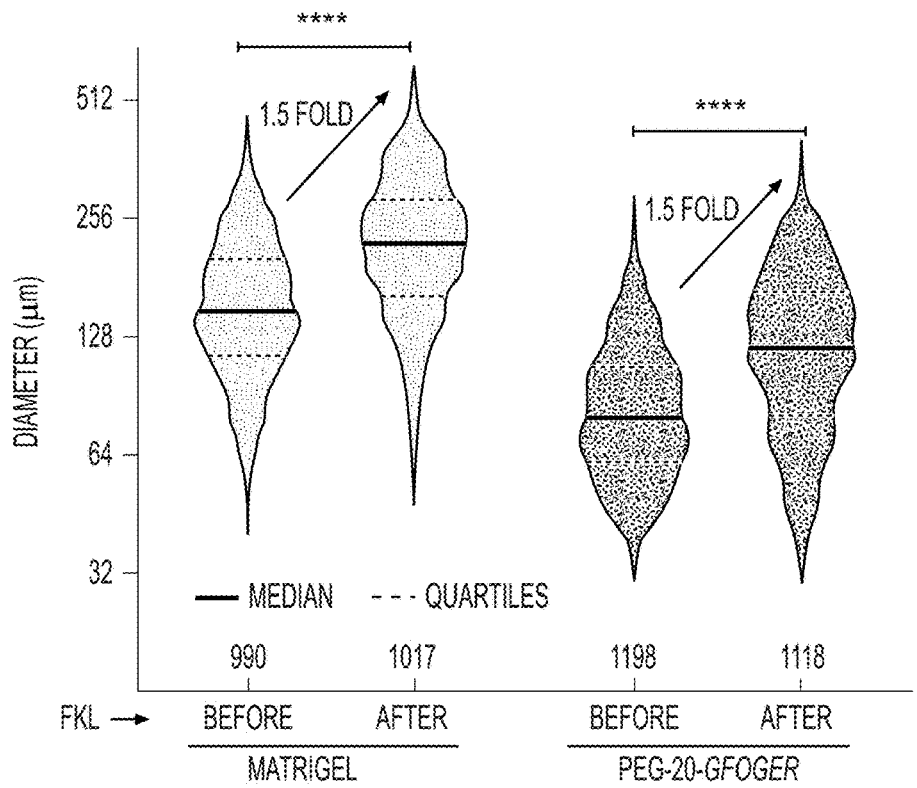

To test the response of organoids to drugs, organoids formed in synthetic hydrogels or MATRIGEL® were stimulated with prostaglandin E2 and forskolin. The diameter of organoids before and after prostaglandin stimulation was measured in images recorded by a microscope (FIG. 8D-E).

Results

Human duodenum stem cells from multiple donors form organoids in the synthetic hydrogels. Live imaging data shows that only few cells were dead by Day 6, not all stem cells form organoids, and the formed organoids varied in size. Cells that do not form organoids remain viable after six days of encapsulation. The results also show that the $\alpha_2\beta_1$ integrin binding is responsible for cell proliferation. Further, the organoids formed in the synthetic hydrogels show correct polarity, undergo appropriate differentiation, and exhibit appropriate architecture and cellular composition.

Figure 10:
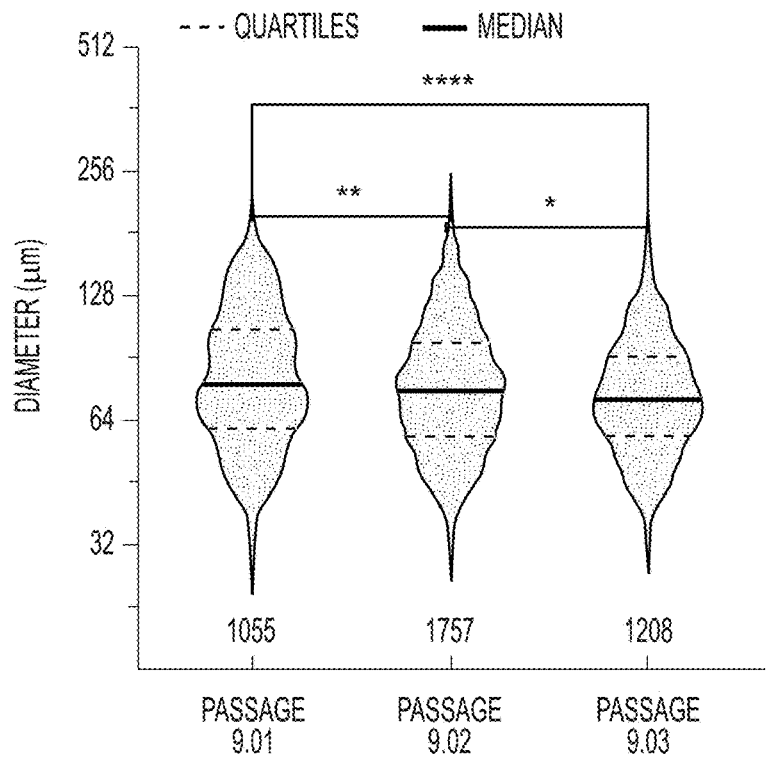
FIG. 10 is a graph showing quantification of enteroid diameters (μm) from three successive passages in the PEG-20-GFOGER hydrogel. Data from a single experiment with 12 replicates in each passage. The number of enteroids measured is depicted under each violin plot. The data was analysed using Kruskal-Wallis multiple comparison of the mean ranks. *P=0.0118,P=0.0024, **P<0.0001. All PEG-20-GFOGER hydrogels were made at nominal concentrations of 0.5 mM GFOGER$_{th}$, 0.25 mM BM-binder, and 0.25 mM FN-binder at 50% XL-MMP-SrtA crosslinker.
Figure 11:
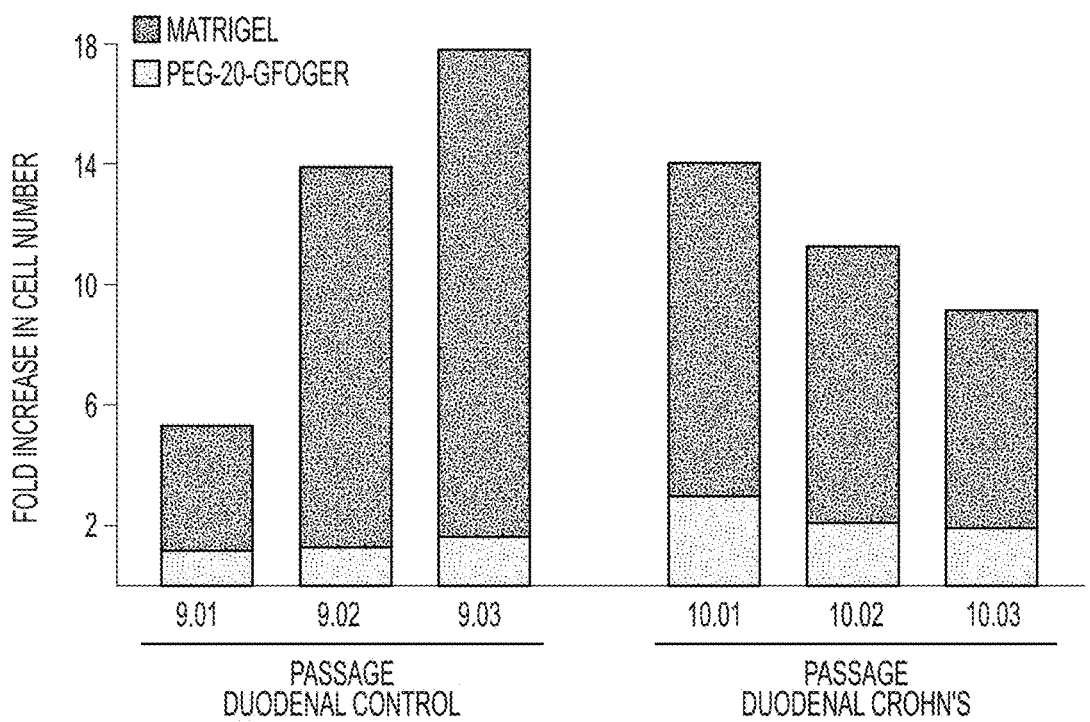
FIG. 11 is a graph showing enteroids grown in the synthetic ECM retain their proliferative capacity. After Sortase-mediated dissolution, six-day-old enteroids were digested and single cells were re-embedded in new synthetic ECM or MATRIGEL®. Cells recovered from the synthetic ECM were subcultured for three consecutive times.

The formed organoids in the synthetic hydrogels retain their proliferative capacity. They can be subcultured into new synthetic hydrogels or MATRIGEL® (FIGS. 10A-B). Cells that do not proliferate in the synthetic hydrogels regain their proliferative capacity in MATRIGEL® (FIG. 11). This may be because factors in MATRIGEL® can promote a non-physiological growth of stem cells.

These hydrogels are also useful in drug discovery. Data shows that organoids formed in the synthetic hydrogels respond to drug stimulation to an extend similar as organoids formed in MATRIGEL® (FIGS. 8D-E).

Example 4. Fully Synthetic Matrices for In Vitro Culture of Primary Human Intestinal Enteroids and Endometrial Organoids Materials and Methods Data Reporting. The experiments were not randomized. The investigators were not blinded during experimental setup or evaluation of experimental outcomes. No statistical methods were used to determine sample size.

Tissue processing. De-identified tissue biopsies were collected from unaffected intestinal regions of children and adult patients undergoing endoscopy for gastrointestinal complaints. Informed consent from adult donors or from a pediatric donors' guardian along with developmentally appropriate assent were obtained at Boston Children's Hospital. All methods were carried out in accordance with the Institutional Review Board of Boston Children's Hospital (Protocol number IRB-P00000529). Tissue processing and initial human and mouse organoid culture were performed at the Harvard Digestive Disease Center, following published protocols (Kasendra et al., *Sci. Rep.* 8:2871 (2018), Miyoshi et al., *Nat. Protoc.* 8:2471-82 (2013)). Organoids were grown in growth factor reduced (GFR) MATRIGEL® droplets (25 μL) overlaid with expansion medium (EM) made with L-WRN conditioned medium (50% vol/vol, ATCC, CRL3276) and supplemented with Y-27632 (10 μM, TOCRIS). Mouse colon organoids were cultured as previously reported (Miyoshi et al., *EMBO J.* 36:5-24 (2017)). Endometrial tissue collection was approved by the Partners Healthcare Institutional Review Board (Protocol number IRB-P001994). De-identified uterine tissue or pipelle biopsies were collected from consented adult donors (ages 18-45). Endometrial organoids were established using published protocols and cultured in endometrial organoid medium (EnOM) (Boretto et al., *Nat. Cell Biol.* 21:1041-1051 (2019), Turco et al., *Nat. Cell Biol.* 19:568-577 (2017)).

Cell culture. Organoids were passaged every four days for human intestinal organoids, eight days for human endometrial organoids and three days for mouse organoids. For passaging, organoids were incubated in Cell Recovery Solution (CRS, Gibco) for 1 h at 4° C., followed by trypsin treatment to generate single cells. The cell suspension was inspected under the microscope to ensure the presence of dispersed single cells and if needed, filtered through a 30 μm cell strainer to remove cell clumps. Single cells were counted using a hemocytometer and seeded in GFR MATRIGEL® (25 μL droplet) at a density of 1,000 cells/μL for human and 500 cells/μL for mouse organoids. After MATRIGEL® polymerization, 600 μL of EM or EnOM was layered on top. Media was changed every two days.

Organoid differentiation. Organoids in both MATRIGEL® and the synthetic matrix were cultured in EM for six days (human) or four days (mouse) before switching to differentiation medium. Human and mouse organoids in MATRIGEL® were differentiated as reported by Kasendra et al., *Sci. Rep.* 8:2871 (2018), Miyoshi et al., *Nat. Protoc.* 8:2471-82 (2013). Intestinal organoids in the synthetic matrix were differentiated using L-WRN conditioned medium (25% L-WRN) diluted in Adv DMEM/F12, HEPES (1 μM, Gibco), Pen/Strep (100 U/mL, 100 mg/mL, Invitrogen), N2 supplement (1×, Gibco), B27 supplement (1×, Gibco), human [Leu15]-gastrin I (10 nM, BACHEM), N-acetyl cysteine (1 mM, SIGMA) and Y-27632 (5 μM, TOCRIS). Mouse organoids in the synthetic ECM were differentiated as in MATRIGEL®.

PEG macromers and peptides. 8-arm PEG macromers with vinyl sulfone (VS) terminal groups (40,000 $M_w$ PEG-VS, "PEG-40" and 20,000 $M_w$ PEG-VS, "PEG-20") were obtained from JenKem Technology (Beijing). All peptides were custom synthesized and purified by Boston Open Labs (Cambridge, MA), GenScript (Piscataway, NJ), or CPC Scientific (Sunnyvale, CA). Peptides sequences and their relevant features are included in the Table 7. "XL-MMP", a crosslinker containing a matrix metalloproteinase (MMP)-sensitive substrate, "XL-MMP-SrtA" a crosslinker containing a MMP-sensitive substrate and a Sortase-sensitive recognition site (LPRTG), "XL-SrtA," a crosslinker containing only the Sortase-sensitive site, "RGD," a fibronectin (FN)-derived peptide containing the canonical RGD motif from the 10th FN type III domain, "PHSRN-K-RGD," a FN-derived peptide containing the RGD motif and the PHSRN synergy site from the 9th FN type III repeat in a branched configuration; "GFOGER," a collagen I-derived peptide presented as a triple helix (Wojtowicz et al., *Biomaterials*, 31:2574-2582 (2010), Carafoli et al., *PLoS ONE*, 7(7): e42473 (2012)), "GFOGDR," a collagen I-derived peptide with E→D point mutation that reduces integrin binding (Knight et al., *J. Biol. Chem.* 275:35-40 (2000)), "G11RGD," an extended ligand of RGD with eleven Gly spacers, "CMPRGD," an extended and clustered RGD-containing ligand using a triple helical collagen mimetic peptide (Hernandez-Gordillo et al., *Biomaterials*, 35:7363-7373 (2014)), "FN-binder," a peptide with affinity for FN, and "BM-binder," a peptide with affinity for collagen IV (C-IV) and laminin (LMN) (Johnson et al., *Biochem. Biophys. Res. Commun.*, 319:448-455 (2004)). All peptides were reconstituted in acidic (pH 5.2) Milli-Q water (Millipore). The concentration of free thiols in all peptides was determined using Ellman's reagent (Sigma). Other peptides were as described in Zustiak and Leach, *Biomacromolecules*. 11:1348-1357 (2010); Kassis et al., *Sci. Rep.* 9:12479 (2019); and Schindelin et al, *Nat. Methods.* 9:676-682 (2012).

TABLE 7

Peptide sequences and relevant features.

| Name | Sequence | Relevant Feature |
|---|---|---|
| XL-MMP | (Ac)-GCRD-VPMSMRGG-DRCG-(Am) (SEQ ID NO: 31) | a dithiol peptide containing a matrix metalloproteinase (MMP)-sensitive substrate |
| XL-MMP-SrtA | (Ac)-GCRD-LPRTG-GPQGIAGQ-DRCG-(Am) SEQ ID NO: 33) | a dithiol peptide containing a MMP-sensitive substrate and a Sortase-sensitive recognition site (LPRTG) |
| XL-SrtA | (Ac)-GCRD-LPRTG-DRCG-(Am) (SEQ ID NO: 35) | a dithiol peptide containing only the Sortase-sensitive site (LPRTG) |
| RGD | (Ac)-GCRE-RGDSP-(Am) (SEQ ID NO: 14) | a fibronectin (FN)-derived peptide containing the canonical RGD motif from the 10th FN type III domain |
| PHSRN-K-RGD | (Ac)-PHSRNGGGK-(GGG-ERCG-(Am))-GGRGDSPY-(Am) | a FN-derived peptide containing the RGD motif and the PHSRN synergy site from the 9th FN type III repeat in a branched configuration, |
| GFOGER | "(Ac)-GGYGGGPG(GPP)$_5$GFOGER(GPP)$_5$GPC-(Am) (SEQ ID NO: 15) | a collagen I-derived peptide presented as a triple helix, |
| GFOGDR | (Ac)-GGYGGGPG(GPP)$_5$GFOGDR(GPP)$_5$GPC-(Am) (SEQ ID NO: 16) | a collagen I-derived peptide with a point mutation E→D that reduces integrin binding |
| G11RGD | (Ac)-GCRE-GGGGGGGGGGGRGDSP-(Am), (SEQ ID NO: 11) | an extended ligand of RGDS with eleven Gly spacers |
| CMPRGD | (Ac)CGG(POG)$_9$RGDSP(Am) (SEQ ID NO: 12) | an extended and clustered RGDS ligand using a triple helical collagen mimetic peptide |
| FN-binder | (Am)-GCRE-TLQPVYEYMVGV-(Ac) (SEQ ID NO: 5) | a peptide with affinity for FN, |
| BM-binder | Ac-GCRE-ISAFLGIPFAEPPMGPRRFLPPEPKKP-(Am) (SEQ ID NO: 4) | a peptide with affinity for collagen IV (C-IV) and laminin (LMN) |

Synthesis of hydrogel precursors. All synthetic matrices were assembled at 3 or 5% PEG (w/v) using 8-arm PEG-40 or 8-arm PEG-20. The mixed PEG-40/20 synthetic matrix was made mixing 1:1 (v/v, 2.5% 8-arm PEG-40 and 2.5% 8-arm PEG-20). All matrices were assembled stepwise via Michael-type addition reaction. First, the PEG-VS macromer (either PEG-40, PEG-20, or the PEG-40/20 mix) was diluted with 10×PBS-HEPES solution (1 mM, pH 7.8); second, the matrix-binder peptides were added to the PEG reaction mixture and incubated for 30 minutes at RT; third, the integrin binder peptides (RGD, PHSRN-K-RGD, GFOGER, G11RGD, CMPRGD or GFOGDR) were added to the reaction mixture and allowed to react for an additional 30 min at RT. This sequential reaction created a PEG-functionalized mixture "fPEG-VS" that was used to resuspend the cells prior to matrix gelation (see cell encapsulation below). The nominal concentration of the matrix-binders in all matrices was 0.25 mM each, whereas the integrin binder peptides were at 1.5 mM (unless otherwise noted in the figure legends). For most experiments the fPEG-VS solution was crosslinked at 50% crosslinking density (unless otherwise noted).

Rheological characterization. After adding the XL-MMP-SrtA crosslinker (50%), 20 µL of each matrix mixture was loaded into a 1 mL syringe that had the tip cut off at the 0.1 mL mark. The matrix was allowed to gel at 37° C. for 20 min and then moved to a 24 well plate that contained 400 µL of 1×PBS. The plate was incubated for 24 hours in a humidified incubator at 37° C., 95% air, and 5% $CO_2$, to allow for equilibrium swelling to occur prior to rheological characterization. This procedure created matrix discs of 1-1.4 mm in thickness. The discs were sandwiched between an 8 mm sandblasted parallel plate and sandblasted base. The shear modulus was determined by performing small-strain oscillatory shear measurements on an Anton Parr MCR 302 instrument. The mechanical response was recorded by performing frequency sweep measurements (0.1-10 Hz) in a constant strain mode (0.05), at 37° C. The shear modulus (G') is reported as a measure of matrix mechanical properties.

Equilibrium swelling. The matrices were prepared at 50% crosslinking density (unless otherwise noted in the figure legends) as described above. After adding the XL-MMP crosslinker, three 30-µL droplets were loaded onto three 18-mm circular glass micro-coverslips.

The mass of the coverslip (mCs) were determined prior to the addition of the gel mixture to calculate the percentage of swelling. The gel mixture/coverslips were placed inside of a 12-well plate and allowed to gel for 20 min in a humidified incubator at 37° C., 95% air, and 5% $CO_2$. At the end of the gelation, each coverslip was weighed again, and the mass recorded as "mass of pre-swelled matrix (mpSM)". One mL of 1×PBS was loaded onto each matrix droplet and returned to the incubator for 24 hours to allow the matrix to reach equilibrium swelling. After 24 hours, the PBS was removed, and the matrices were washed twice with 1 mL of $dH_2O$. The water was removed completely before the matrix/coverslips were weighed again. This was recorded as "mass of swelled matrix (mSM)". Finally, the matrix/coverslips were placed in a 60° C. oven overnight to determine the mass of the dry matrix. To calculate the percentage of swelling the following formula was used ((mpSM−mCs)/(mSM−mCs))*100. The pore size (4) was calculated according to Flory-Rehner equations and derived formulas described in (Zustiak and Leach, *Biomacromolecules.* 11:1348-1357 (2010)). In experiments to determine the effect of the crosslinking density on swelling, the synthetic matrices were made with 35, 40, 45, 50, 55, and 60% XL-MMP crosslinker density. The percentage of swelling was calculated as above.

Cell encapsulation. Four-day old organoids grown in MATRIGEL® were collected and processed as above to generate single cells. The cell suspension was inspected under the microscope to ensure the presence of dispersed single cells and if needed, filtered through a 30 µm cell strainer to remove cell clumps. Single cells were counted using a hemocytometer then resuspended in the matrix precursor solutions (fPEG-VS) prior to the addition of the crosslinker and Y-27632 (10 µM). In parallel, single cells were resuspended in MATRIGEL® that served as experimental control during matrix evaluation. In both cases, cells were encapsulated at a density of 500 cells/µL of matrix. Three µL (1,500 cells) of the matrices were loaded into a Nunc MicroWell 96-well optical-Bottom plate and allowed to polymerase for 20 min in a humidified incubator at 37° C., 95% air, and 5% $CO_2$. After gelation, 100 µL of EM or EnOM was loaded into each well. Media was changed every two days. Eight-day old endometrial organoids were used to generate single cells. The encapsulation process in MATRIGEL® or the synthetic ECM, for endometrial organoids, was performed similarly to intestinal organoids. The 3 µL droplet size for synthetic ECM (5 µL for passaging experiments) was chosen to conserve resources while screening, facilitate imaging and reduce inhomogeneities in organoid growth between the rim and center regions for droplets of 15 µL or greater volume.

Intestinal and endometrial organoid diameter. 4× brightfield (BF) single-plane images of six-day old enteroids and eight-day old endometrial organoids were captured using an EVOS M500 microscope (Invitrogen). Images were analyzed using a deep learning based algorithm as described previously to produce a diameter distribution for each condition (Kassis et al., *Sci. Rep.* 9:12479 (2019)).

Enteroid formation efficiency. Single cells were encapsulated as above and cultured in EM for four days (MATRIGEL®) or six days (synthetic matrix) before imaging at 10× magnification using an EVOS M500 microscope. Organoids were assessed at these relatively early time points to avoid artefacts in image analysis due to overlapping large organoids; as ~70% of cells in MATRIGEL® had formed organoids by day four, and organoids in synthetic gels emerge later, these relatively early time points allow reasonable comparison of the overall efficiency of the synthetic gels compared to MATRIGEL®. Sixty BF images, spanning the entire thickness of the matrix (~600 µm), were collected from the center of the droplet (approximately ⅓ of the total droplet volume). The image z-stacks were processed in Fiji using the time lapse Gaussian-based stacker focuser plugin to create a single image with all enteroids in focus. The number of enteroids with a clear lumen and the number of single cells were manually counted using the cell counter feature in Fiji (Schindelin et al., *Nat. Methods.* 9:676-682 (2012)). Few cell clumps that did not show a clear lumen but were bigger than single cells were also observed and counted. Enteroid formation efficiency was calculated as the percentage of enteroids with a clear lumen relative to the total number of enteroids, single cells, and cell clumps, counted in each droplet.

Live/dead imaging. Single cells were encapsulated as before for six days (intestinal) or eight days (endometrial) before the addition of Calcein AM (2 mM) and Ethidium homodimer-1 (2 mM) for 20 minutes. Images were captured using either a ZEISS confocal Laser Scanning Microscope (LSM 880) equipped with temperature (37° C.), humidity, and $CO_2$ (5%) controls or an EVOS M500 (Invitrogen) microscope (no incubation). A 1.6 mm by 1.6 mm area and ~600 µm thick section of either MATRIGEL® or the synthetic ECM were imaged with the confocal. With the EVOS, the center of the droplet was captured, which is ~⅓ of the total matrix area. The final images were processed using the ZEN blue ZEISS companion software or Fiji (Schindelin et al., *Nat. Methods.* 9:676-682 (2012)). For time-course live/dead imaging analysis, 60 z-stacks images were taken the day of seeding (day 0) then every two days for up to ten days, using the EVOS M500 microscope and processed as above.

Time-lapse live imaging. Single cells were encapsulated and plated on 96-well optical plates as described before, then cultured in OEM. Bright field images were captured using a ZEISS confocal Laser Scanning Microscope (LSM 880) equipped with a wide-field camera and temperature (37° C.), humidity, and $CO_2$ (5%) controls. A single plane of four-day old enteroids were imaged every 5 minutes for 48 hours. The final videos were prepared in Fiji using frame interpolation to smooth the video (Schindelin et al., *Nat. Methods.* 9:676-682 (2012)). To capture individual cells forming enteroids, the entire thickness of the matrices was imaged the day after encapsulation and then everyday for up to six days. The stack of images was processed in Fiji as described in enteroid formation efficiency (Schindelin et al., *Nat. Methods.* 9:676-682 (2012)).

Organoid Passaging in Synthetic ECM. To determine if cells from enteroids in the synthetic ECM retain their proliferative capacity, six-day old enteroids were collected from within the synthetic ECM using SrtA treatment (Valdez et al., *Biomaterials,* 130:90-103 (2017)), then digested them with trypsin to generate a single cell suspension. Cells (500 cells/µl, 5 µl droplets, 48 droplets total) were embedded in MATRIGEL® or the synthetic ECM and cultured in EM for six days. After six days, the matrix droplets were pooled and processed as follows; enteroids in MATRIGEL® were released using CRS whereas enteroids in the synthetic ECM were released using SrtA treatment. Enteroids in both conditions were then digested with trypsin to get the total number of cells recovered from the pooled enteroids, from each matrix condition. The fold increase in cell number was calculated as the ratio of total number of cells obtained from enteroids after six days of culture divided by the total number of cells used at the beginning of the experiment. The cells recovered from enteroids in MATRIGEL® were discarded after the count. The cells recovered from enteroids in the synthetic ECM were used to set up a new experiment (first passage, 500 cells/μl, 5 μl droplets, 48 droplets total) in new synthetic ECM or MATRIGEL®. At the end of six days, the fold increase in cell number was determined as before. This process was repeated three consecutive passages using two human duodenal donors. In parallel experiments, using the same pool of cells, the enteroid diameter of the three consecutive passages was measured.

Quantitative real time PCR (qPCR). Four-day old enteroids grown in MATRIGEL® were used to generate a single-cell suspension as described above. Single cells (500 cells/μL) were encapsulated in MATRIGEL® or the synthetic ECM, then cultured in EM. After six days, intact enteroids were released from MATRIGEL® and the synthetic ECM, as described before. Intact enteroids were pelleted, resuspended in TRIzol reagent (ThermoFisher Scientific, 15596026), and then stored at $-80°$ C. until processing. From the initial cell suspension, 500,000 cells were reserved at $-80°$ C. in TRIzol. This single-cell population was used to determine the gene expression of the "initial cell population" at the time of experimental set up. RNA was extracted from enteroids (or cells) using the Directzol RNA Mini-Prep kit (Zymo Research) per the manufacturer's protocols with the inclusion of an on-column DNase step using the PureLink DNase Set (Thermofisher Scientific, 12185010). cDNA was synthesized from ~1 μg of total RNA using the High-Capacity RNA-to-cDNA Kit (Thermofisher Scientific, 4387406) per manufacturer's protocols. TaqMan Fast Advanced Master Mix (Thermofisher Scientific, 4444557) was used in congruence with the cell-specific probes for qPCR. Gene expression was determined using the StepOnePlus real-time PCR system (Applied Biosystems) and calculated using the $\Delta\Delta Ct$ method in GraphPad Prism. Gene expression was first normalized using the housekeeping GAPDH gene in each sample, then the relative fold change in gene expression, in MATRIGEL® or the synthetic ECM, was calculated against the gene expression of the "initial cell population" that was set to 1. The experiment was repeated three times with two duodenal donors.

Histological processing and immunostaining. Mouse intestinal organoids were fixed while still in the gel (3D), then paraffin-embedded and sectioned in the Histology Center at the Koch Institute at MIT. 5-micron tissue sections were hematoxylin and eosin stained using standard procedures.

Immunostaining and EdU labeling. Organoids and enteroids were processed in two formats: in 3D (embedded within the synthetic ECM or MATRIGEL®) and in suspension (free floating) after being released from the matrices. Six-day old enteroids in 3D were treated with EdU (5-ethynyl-2'-deoxyuridine, 20 μM) for 3 hr (Alexa Flour 488 Click-it EDU, Thermo Fisher) prior to fixation overnight with formalin (10%, VWR) at 4° C. Eight-day old endometrial organoids in 3D were treated with EdU for 6 hr prior to overnight fixation. Eight-day old colon organoids were treated with EdU for 6 hr, then released from the matrices and fixed as free-floating organoids for 30 min at RT. After fixation, organoids and enteroids in 3D were permeabilized with 0.1% triton X-100 in PBS overnight followed by blocking (4% BSA/0.5% Tween 20 in 1×PBS or 4% Donkey serum/0.5% Tween 20 in 1×PBS) overnight at 4° C. with 200 rpm shaking. Free-floating organoids were permeabilized for 1 h at RT incubated in a tube rotator set at 30 rpm, followed by 3 hr of blocking. To identify proliferative cells, the Alexa Flour 488 was click-reacted according to the manufacturer instruction. Immunostaining for cell-specific markers was done using the following primary antibodies, diluted in blocking solution; goat anti-E-cadherin (R&D, AF748, 1:200), goat anti-hDPPIV/CD26 (Invitrogen, AF1180, 1:400), rabbit anti-Col IV (Abcam, Ab6586, 1:200), rabbit anti-Lysozyme (Dako, A0099, 1:400), rabbit anti-LMN (Abcam, Ab11575, 1:200), rabbit anti-Ki67, (Abcam, Ab15580, 1:200 or ab16667, 1:100), rabbit anti-NHE3/SCL9A3 (Novus, NBP-82574), mouse anti-Villin (Santa Cruz, SC-58897, 1:50), mouse anti-CD44-v6 (Abcam, Ab78960, 1:200), mouse anti-Muc2 (Santa Cruz, SC515032 1:200), mouse anti-EpCAM (Abcam, ab7504 1:200). Samples in 3D were incubated for two days in primary antibodies at 4° C. and 200 rpm shaking. Free-floating samples were incubated overnight in primary antibodies at 4° C. in the tube rotator set at 30 rpm. The secondary antibodies and dilutions used were; donkey anti-goat Alexa Fl 568 (ThermoFisher, A11057, 1:200), donkey anti-rabbit Alexa Fl 568 (ThermoFisher, A10042, 1:200), and donkey anti-mouse Alexa Fl 568 (ThermoFisher, A10037, 1:200). Nuclear staining was done using DAPI (1 mg/mL, 1:2,000). F-actin staining was done using either Alexa Fl 488 phalloidin (ThermoFisher, A12379, 1:200) or Alexa Fl 568 phalloidin (ThermoFisher, A12380, 1:200). DAPI and f-actin staining was done in combination with the secondary antibody. Samples in 3D were incubated in secondary antibodies for two days at 4° C. and 200 rpm shaking. At the end of the incubation, samples in 3D were washed five times (10 minutes each, 200 rpm at RT) prior to the addition of CytoVista reagent (Thermofisher) to match the refraction index and allow imaging in 3D. Free-floating samples were incubated overnight in secondary antibodies at 4° C. in the tube rotator set at 30 rpm, followed by five washes (10 min each, at RT and 30 rpm). The organoids were gently pelleted and resuspended in prolong gold antifade reagent (ThermoFisher, P36935), then transferred onto a glass slide modified with a 20 mm secure seal spacer (0.12 mm deep, ThermoFisher, S24736). 5-micron tissue sections were incubated in mouse anti-Villin (Santa Cruz, SC-58897, 1:50) overnight, followed by donkey anti-mouse Alexa Fl 568 (ThermoFisher, A10037, 1:200) and DAPI staining. Images were captured using a ZEISS confocal Laser Scanning Microscope (LSM 880).

Statistical analysis and sample information. Statistical significance between experimental treatments were determined as follows: Enteroid diameters were analyzed using one-way ANOVA and Kruskal-Wallis multiple comparison of the mean ranks. Storage modulus data analyzed using one-way ANOVA and Sidak's multiple comparison whereas swelling and pore size data was analyzed using Kruskal-Wallis multiple comparison of the mean ranks. Enteroid formation was analyzed using either one-way ANOVA and Holm-Sidak's multiple comparison of the mean or two tailed Mann-Whitney tests when comparing two groups. qPCR data were analyzed using multiple t tests and the Holm-Sidak method. All statistical analyses were performed in the GraphPad Prism 8.0 software.

Results

Niche-inspired synthetic ECM design, synthesis, and biophysical characterization. Intestinal stem cells (ISCs) at the bottom of the crypt express $\alpha 2\beta 1$, $\alpha 5\beta 1$, and $\alpha 6\beta 4$ integrins (Muñoz et al., *EMBO J.*, 31:3079-3091 (2012); Benoit et al., *Biochem. Biophys. Res. Commun.* 399:434-439 (2010);

Benoit et al., *J. Signal Transduct.* 2012:1-10 (2012); Starchenko et al., *Mol. Biol. Cell.* 28:1288-1300 (2017); Patey et al., *Gastroenterology,* 113:833-843 (1997); and Stallmach et al., *Gut,* 33:342-346 (1992)). Consequently, ligands for these receptors are attractive components of synthetic ECM. Peptides targeting α2β1 and α5β1 integrins were considered. Matrix-binding peptides were also included to capture cell-produced ECM that contains natural ligands for α6β4 integrin and other epithelial ECM-binding receptors, as matrix-binding peptides have been shown to enhance endometrial epithelial monolayer stability on PEG-based gels (Cook et al., *Integr. Biol.,* 9:271-289 (2017)). Synthetic ECMs with these cell interaction features provide a combination of cues to first signal initial proliferation of isolated stem/progenitor cells, and then to help proliferating enteroids and organoids polarize properly.

A modular synthetic ECM was created by combining commercially available 8-arm vinyl sulfone-activated PEG macromers partially modified with integrin-binding peptides and ECM-binding peptides, together with peptide cross-linkers containing a matrix-metalloproteinase (MMP)-sensitive degradation site. With these components, the identity of the integrin-binding ligand, the biophysical properties of ligand presentation, and the ECM biomechanical properties at local and macroscale were systematically varied, the latter via modulation of macromer and crosslinking properties (FIGS. 1A-1C and Table 8).

Specifically, two different 8-arm PEG macromers were used, PEG-20 (Mw=20,000) and PEG-40 (Mw=40,000), activated with vinyl sulfone (VS) terminal groups that react orthogonally with thiol-containing peptides at physiological pH (FIGS. 1D-1F). Based on the contour PEG length in aqueous solution (Oesterhelt et al., *New J. Phys.,* 1:6 (1999)), the fully-extended arm lengths for each macromer correspond to either ~16 nm (PEG-20) or ~32 nm (PEG-40), affording systematic variation of both tether length for ligand presentation as well as gel biophysical properties. In initial screening experiments to evaluate the role of ligand identity on organoid emergence, PEG macromers were functionalized with either the branched fibronectin-derived PHSRN-K-RGD peptide (Kuhlman et al., *Biomacromolecules.* 8:3206-3213 (2007); Feng et al., *Biochemistry,* 43:15811-15821 (2004); and Huettner et al., *Trends Biotechnol.,* 36:372-383 (2018)) or the collagen I-derived GFOGER sequence (Table 8) (Knight et al., *J. Biol. Chem.,* 275:35-40 (2000)). Further investigation of the role of ligand identity involved a variant inactive GFOGER, and the role of ligand clustering employed variants of RGD-containing peptides (Table 8). All gels also included peptides with affinity for FN, collagen IV (C-IV), and LMN (FN-binder and BM-binder, respectively), reasoning that initial integrin engagement is only a first step, with possible subsequent interactions mediated by matrix that cells produce and assemble locally. Finally, except in one series of experiments testing effects of synthetic gel degradation properties where a peptide containing a SrtA-susceptible site but no MMP substrates (XL-SrtA) was used, one of two MMP-sensitive peptide crosslinkers: XL-MMP-SrtA was included, concatenated with a site susceptible to cleavage with exogenously-added transpeptidase SrtA enzyme to enable cell-mediated matrix remodeling and recovery of intact organoids, respectively; or XL-MMP, containing a MMP substrate but no substrate for SrtA (Table 7).

TABLE 8

Gel composition and physical properties of hydrogels

| Gel Composition[&] | | | | Physical Properties | |
|---|---|---|---|---|---|
| Macromer 8-arm PEG | PEG % (w/v) | Integrin Ligands (nominal concentration, mM) | Cross-link % | Swelling (%) | Modulus* (Pa) |
| PEG-40 | 5 | PHSRN-K-RGD (1.5) | 50 | 224 ± 4[†] | 620 ± 20[†] |
| PEG-40 | 5 | GFOGER (1.5) | 50 | 296 ± 18[†] | 696 ± 53[†] |
| PEG-20 | 5 | PHSRN-K-RGD (1.5) | 50 | 169 ± 6[†] | 817 ± 63[†] |
| PEG-20 | 5 | GFOGER (1.5) | 50 | 196 ± 12[†] | 929 ± 63[†] |
| PEG-40/20 | 2.5 PEG-40 2.5 PEG-20 | PHSRN-K-RGD (1.5) | 50 | 195 ± 5[†] | 714 ± 29[†] |
| PEG-40/20 | 2.5 PEG-40 2.5 PEG-20 | GFOGER (1.5) | 50 | 185 ± 5[†] | 1034 ± 21[†] |
| PEG-20 | 5 | RGD (1.5) | 50 | ~169[§] | ~817[§] |
| PEG-20 | 5 | G11RGD (1.5) | 50 | ~169[§] | ~817[§] |
| PEG-20 | 5 | CMPRGD (1.5) | 50 | ~196[§] | ~929[§] |
| PEG-20 | 5 | GFOGER (0)/ GFOGDR (1.5) | 50 | ~196[§] | ~929[§] |
| PEG-20 | 5 | GFOGER (0.5)/ GFOGDR (1.0) | 50 | ~196[§] | ~929[§] |
| PEG-20 | 5 | GFOGER (1.0)/ GFOGDR (0.5) | 50 | ~196[§] | ~929[§] |
| PEG-20 | 5 | GFOGER (1.5) | 35 | 442 ± 29[†] | 497 ± 6[#] |
| PEG-20 | 5 | GFOGER (1.5) | 40 | 284 ± 11[†] | 576 ± 7[#] |
| PEG-20 | 5 | GFOGER (1.5) | 45 | 253 ± 8[†] | 672 ± 8[#] |
| PEG-20 | 5 | GFOGER (1.5) | 50 | 195 ± 5[†] | 839 ± 42[#] |
| PEG-20 | 5 | GFOGER (1.5) | 55 | 174 ± 3[†] | 1053 ± 47[#] |
| PEG-20 | 5 | GFOGER (1.5) | 60 | 173 ± 3[†] | 1307 ± 44[#] |
| PEG-20 | 3 | GFOGER (1.5) | 50 | ~300[¶] | ~110[¶] |

[&]All gels contained nominal 0.25 mM BM-binder and 0.25 mM FN-binder, crosslinked with XL-MMP or XL-MMP-SrtA
*Storage modulus; see Methods
[†]Data represent a minimum of two and maximum of three independent experiments (three hydrogels per experiment)
[#]Data represent a single experiment with three hydrogels per condition
[§]Estimated value based on previous results with similar gel composition and integrin binder peptide properties
[¶]Estimated values from unpublished data of similar gel composition (1.5 mM GFOGER, 1.5 mM PHSRN-K-RGDS, 1 mM Matrix binders, and 50% crosslinker)

The two primary integrin ligands investigated differ biophysically in that PHSRN-K-RGD is a monomeric ligand incorporating the RGD and PHSRN motifs in a branched configuration to mimic the biophysical presentation found in native FN, whereas the collagen-derived GFOGER peptide is chemically synthesized as a monomer, but self-assembles into a triple helix configuration (referred here as GFOGER triple helix, $GFOGER_{th}$), thus mimicking the biophysical presentation of collagen fibers (FIG. 1F) (Knight et al., *J. Biol. Chem.,* 275:35-40 (2000)). Consequently, a nominal 1.5 mM concentration of monomeric integrin-binding ligand added to the gelation solution results in a gel with 1.5 mM of PHSRN-K-RGD available to bind integrins, but nominal 1.5 mM GOFGER is present as 0.5 mM of $GFOGER_{th}$ available for integrin binding (FIG. 1F).

The general properties of the synthetic ECMs are illustrated by focusing on the subset used to compare the performance of the two primary integrin ligands, PHSRN-K-RGD and GFOGER, in a panel of 6 gels (Table 8). This panel was created by varying the PEG macromer (PEG-20, PEG-40 or PEG-40/20; see Methods) and ligand (i.e., PHSRN-K-RGD or GFOGER) while keeping the total PEG macromer weight percent (5%) and crosslink density (XL-MMP, 50%) constant (Table 8, Table 9, and Methods). The theoretical percentage of reactive PEG chain ends free after gelation varies (30-45%) depending on each gel composition, macromer composition, and other factors (Table 9), thus nominal concentrations of peptides are attained in the gel, as the Michael addition is highly efficient (Kim et al., *Soft Matter.*, 12:2076-2085 (2016)). The values of free arms for gels containing the GFOGER peptides are estimation based on the reaction of the self-assembled $GFOGER_{th}$ with 1-3 reactive PEG arms. The 3 free thiols in a $GFOGER_{th}$ triple helix are sterically constrained from forming disulfide bonds (Reyes et al., *J. Biomed. Mater. Res. —Part A.*, 65:511-523 (2003); and Tanrikulu et al., *J. Am. Chem. Soc.*, 136:13490-13493 (2014)). Hence, each helix reacts with a PEG arm under these sub-stoichiometric conditions (i.e., excess VS-activated arms compared to free sulfhydryls, Table 9), although steric hindrance may result in incomplete reaction.

TABLE 9

Physical properties of designed hydrogels[&].

| Relevant Feature | PEG-PHSRN-K-RGD | | | PEG-GFOGER | | | |
|---|---|---|---|---|---|---|---|
| 8-arm PEG (kDa) | 40 | 40/20 | 20 | 40 | 40/20 | 20 | 20 |
| 8-arm PEG % (w/v) | 5 | 2.5 PEG-20 2.5 PEG-40 | 5 | 5 | 2.5 PEG-20 2.5 PEG-40 | 5 | 3 |
| Total PEG arms (mM) | 10 | 15 | 20 | 10 | 15 | 20 | 12 |
| PEG arms used by integrin binders (%) | 15 | 10 | 7.5 | 5-15[†] | 3.3-10[†] | 2.5-7.5[†] | 4.2-12.6[†] |
| PEG arms used by matrix binders (%) | 5 | 3.3 | 2.5 | 5 | 3.3 | 2.5 | 4.2 |
| PEG arms used by crosslinker (%) | 50 | 50 | 50 | 50 | 50 | 50 | 50 |
| PEG arms free after gelation (%) | 30 | 36.7 | 40 | 30-40[†] | 36.7-43.4[†] | 40-45[†] | 33.2-41.6[†] |
| Avg. number of integrin binders per PEG macromer | 1.2 | 0.7 | 0.6 | 0.4[#] | 0.27[#] | 0.2[#] | 0.33[#] |

[&]Hydrogels made at 1.5 mM integrin binder, 0.25 mM BM- and 0.25 mM FN-Binder, and 50% (XL-MMP or XL-MMP-SrtA) crosslinker
[†]This range is based on the possibility of GFOGERth reacting with a single PEG arms or three PEG arms
[#]These values represent a GFOGERth bound to a single PEG arms. It is possible a GFOGERth (three thiols) could react with up to three PEG arms The swelling ratios and storage moduli of these 6 gels followed expected trends, with PEG-40 gels demonstrating greater swelling (swelling ratio of 2.2-3.0-fold) and lower storage moduli (620-700 Pa) than PEG-20 gels (swelling ratio of 1.7-2.0 and storage moduli of 820-930 Pa), with the 50/50 w/w mix skewing toward values for the PEG-20 (swelling of 1.9-2.0 and storage modulus of 714-1034 Pa) (Tables 8 and 10; statistical significance listed in Table 10). The skew of PEG-40/20-GFOGER matrix properties toward those of PEG-20-GFOGER is not surprising as the PEG-20 solution contributes twice the amount of PEG arms (10 mM, ~67%) than a 2.5% of a PEG-40 solution (5 mM-33%) in the final PEG 40/20-GFOGER matrix (Tables 8 and 10). Gel swelling reduced the ligand concentrations in hydrogels from the nominal values shown in Table 8 to actual values. The properties of additional synthetic ECM formulations used in experiments described throughout the study are also shown in Table 8. The rationale for these experimental parameters is described in the relevant Results sections.

TABLE 10

Biomechanical properties of the two sets of synthetic matrices

| | PEG-PHSRN-K-RGD series | | | PEG-GFOGER series | | |
|---|---|---|---|---|---|---|
| 8-arm PEG (kDa) | 40 | 40/20 | 20 | 40 | 40/20 | 20 |
| Storage Modulus (Pa) | 620 ± 20[a] | 714 ± 29[ab] | 817 ± 63[bc] | 696 ± 53[ab] | 1034 ± 21[d] | 929 ± 63[cd] |
| Swelling (%) | 224 ± 4[ab] | 195 ± 5[bc] | 169 ± 6[c] | 296 ± 18[a] | 185 ± 5[bc] | 196 ± 12[bc] |
| Pore Size (nm) | 30 ± 0.2[a] | n.d. | 17 ± 0.5[b] | 33 ± 1.2[a] | n.d. | 21 ± 1.5[b] |

Figure 2A:
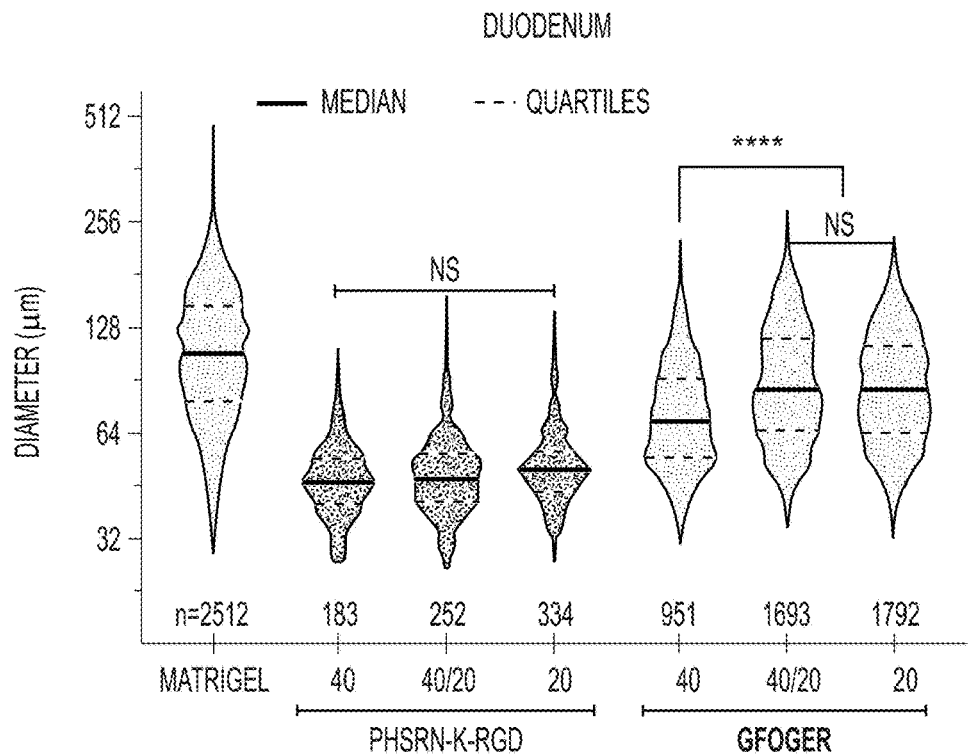
FIGS. 2A, 2B and 2D are quantitative graphs showing that the synthetic ECMs support enteroid formation from single cells from human duodenal and colon donors (Fures 2A-2B) and mouse colon (2D). All synthetic ECM were made at 5% PEG, 1.5 mM integrin binder peptide, 0.25 mM BM-binder, and 0.25 mM FN-binder, crosslinked with XL-MMP at 50%. The concentrations for the integrin and matrix binders may be adjusted by the percentage of volumetric swelling described in Table 10. Enteroid diameter of duodenal (n=3 experiments) and colon (n=2 experiments) donors in the two sets of synthetic ECM is shown in FIGS. 2A and 2B. The number of enteroids measured is depicted below each violin plot. MATRIGEL® median diameters were significantly larger (P<0.0001) than enteroid diameters in the synthetic hydrogels. Data was analyzed using Kruskal-Wallis multiple comparison of the mean ranks. ns: not significant, *P=0.137, ****P<0.000.
Figure 2B:
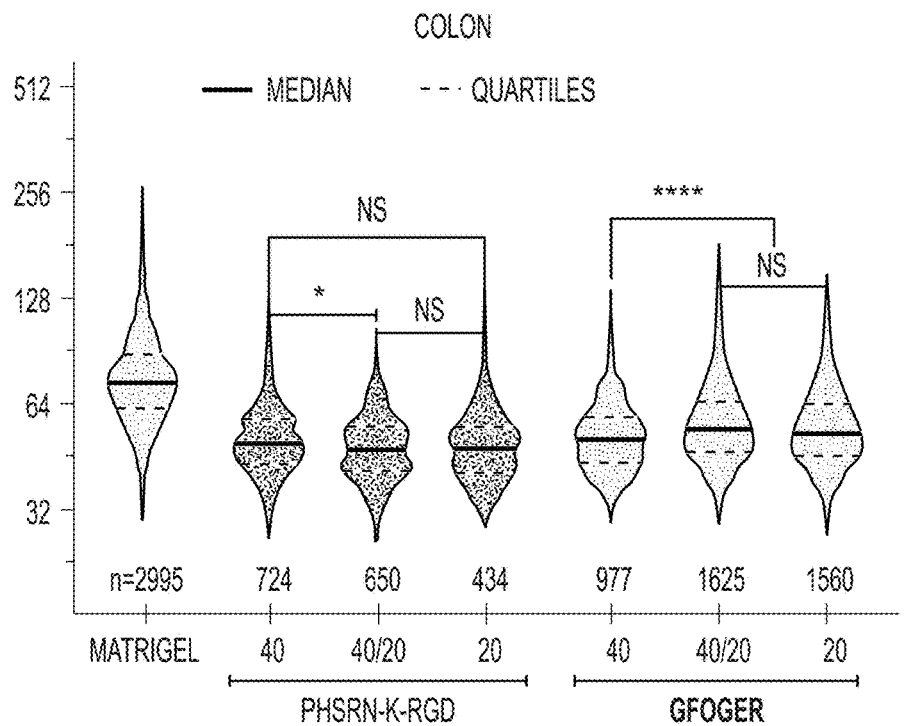
Figure 2C:
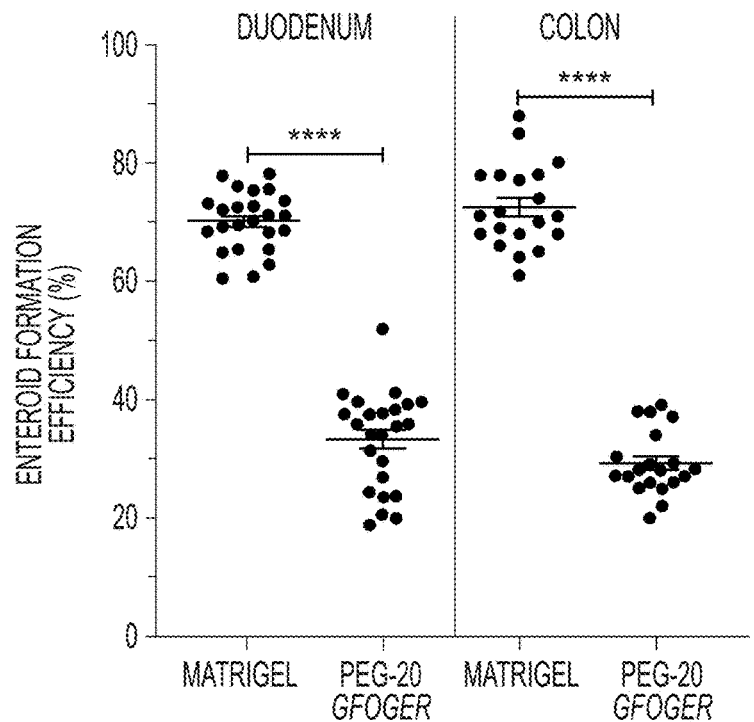
FIG. 2C is a graph showing enteroid formation efficiency of duodenal and colon donors in the PEG-20-GFOGER matrix from two independent experiments. Each symbol represents a single hydrogel with the mean and SEM. **P<0.0001 using Mann-Whitney two tailed t-test.
Figure 2D:
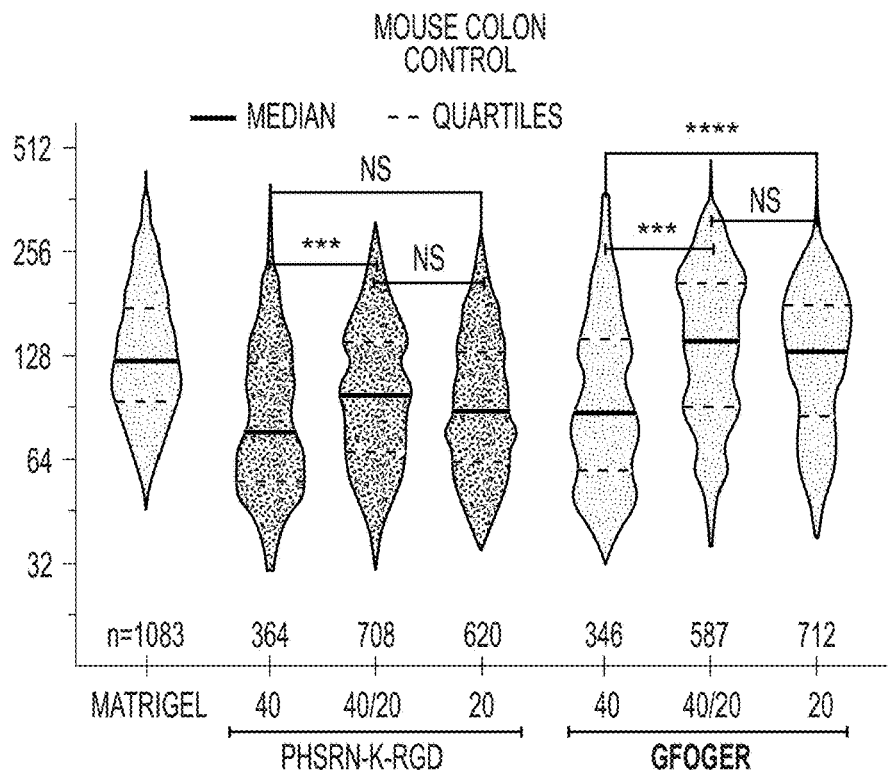

[a]Note =
Values with the same letter are statistically similar.
n.d. = Not Determined Biomechanical properties of the two sets of synthetic matrices are shown in Table 10, showing storage modulus data (n=6 gels). Swelling and theoretical pore size data (n=12 gels). Representative images of 6-day old duodenal and colon enteroids emerging in two sets of synthetic ECMs were taken. Seven donors (six human duodenal, one colon, and one mouse colon) were evaluated FIGS. 2A, 2B depict human donors and FIG. 2D show results from a mouse colon donor.

Synthetic ECM Containing GFOGER Best Supports Enteroid Growth.

Donor-to-donor and species variability are both known to affect organoid growth. Thus, to test the compendium of synthetic matrix formulations described above (Tables 8 and 9), seven human donors (six duodenal and one colon) were selected that varied in sex, age and pathological state, and one mouse colon donor. Single cells obtained by dissociating MATRIGEL®-expanded human enteroids at day 4 or mouse enteroids at day 3, were embedded in either MATRIGEL® or synthetic ECMs (3 µL droplets, with 12 droplets per condition in 12 wells, and then cultured in expansion medium (EM)). To identify the robustness of organoid emergence from single cells encapsulated in different matrices, the total number of spherical multi-cellular structures presenting with a clear lumen (formation efficiency) and the distribution of organoid diameters (proliferation) were quantified, both as a function of time. An automated image analysis program was implemented to assess the distribution of organoid diameters in a defined region of the gel droplet as a proxy for cell proliferation and organoid growth.

Organoids emerging in both MATRIGEL® and synthetic ECMs had a wide range of size distributions at each time point after culture initiation, but all were characterized by a spherical morphology composed of a single layer of thin epithelial cells. Such spherical intestinal tract-derived organoids, which appear undifferentiated and potentially stem-enriched, are referred to as "enteroids" and reserved the term "organoid" for enteroids that showed characteristics of further differentiation.

Synthetic matrices supported enteroid formation from human and mouse donors with various degrees of success (FIGS. 2A, 2B and 2D). As expected, the general features of duodenal and colon enteroid growth in MATRIGEL® were recapitulated in synthetic ECMs: mouse colon enteroids exhibited apparent faster growth rates than human colon enteroids in both MATRIGEL® and the synthetic ECMs; human duodenal enteroids appeared to grow faster in both MATRIGEL® and the synthetic ECMs compared to the colon enteroids. These apparent growth rates are reflected in the magnitude of the median size distribution at the reported time points (FIGS. 2A, 2B and 2D). A 5% 20 kDa-PEGVS, 1.5 mM GFOGER, 0.25 mM FN-Binder, 0.25 mM BM-Binder, 45% Xlinker provides enteroid formation efficiency of about 30%-40% (FIG. 2C).

The "growth rates" inferred from population median diameters are referred to as "apparent growth rates", since the median diameter metric convolutes two phenomena: formation of a multi-cellular cystic enteroid structure from an individual cell, and rate of diameter expansion of each enteroid. While these separate phenomena in were not investigate a statistically rigorous manner, images and videos showed that enteroids were slower to emerge in synthetic ECM but expanded in diameter at comparable rates to those in MATRIGEL® once they had a clear lumen. In the PEG-20-GFOGER and PEG-40/20-GFOGER gels, mouse colon enteroids reached similar sizes to mouse enteroids in MATRIGEL® when analyzed at the same end point (FIG. 2D). Further, the enteroid median diameters were statistically similar (131, 139 and 122 µm for PEG-20-GFOGER and PEG-40/20-GFOGER, and MATRIGEL® respectively (P>0.9999, FIG. 2D).

Although human duodenal enteroids in synthetic ECMs always exhibited diameter distributions that skewed toward a statistically smaller median than those in MATRIGEL® at the same time point, synthetic ECMs with PEG-20 macromers modified with GFOGER and ECM binding peptides resulted in diameter distributions that approached those in MATRIGEL® for several donors. Synthetic ECMs with similar peptide composition, but a 50/50 mix of PEG-20 and PEG-40 macromers (PEG-40/20-GFOGER) was effective for many of the donors (FIGS. 2A-2B). Specifically, when cultured in the PEG-20-GFOGER formulation two control (non-diseased) duodenal donors exhibited median diameters of 83 and 64 µm compared to MATRIGEL® with median of 107 and 83 µm; similar results were observed in the mixed PEG-40/20-GFOGER gels (median of 85 and 67 µm).

Among the 3 diseased donors the medians in the optimal composition (PEG-20-GFOGER) ranged from 71 to 99 µm compared to MATRIGEL® with medians of 110 to 121 µm. In the PEG-40-GFOGER the median ranged from 56 to 76 µm. For the PEG-40/20-GFOGER the medians ranged from 69 to 98 µm. Encouragingly, these same formulations also supported relatively good growth of human colon enteroids, with medians of 52, 53, and 73 µm for PEG-20-GFOGER, PEG-40/20-GFOGER and MATRIGEL®, respectively. The variation in enteroid sizes is reflected in the range of 75% quartile deviation from the median in each case.

Notably, the results showed the significance of using a variety of donors and tissue types, as matrices that supported mouse enteroids did not robustly support human donors. Across the human donors, donor-to-donor variability was noticed on enteroid size distribution in the synthetic ECMs that mirrored the donor-to-donor variability observed in MATRIGEL®. The best synthetic ECM (PEG-20-GFOGER) resulted in an enteroid formation efficiency of 35% (duodenal) and 28% (colon) (FIG. 2C), both lower than the value of (~70%) in MATRIGEL®. In this analysis, efficiency is defined as the percentage of enteroids with a clear lumen relative to the total number of enteroids, single cells, and cell clumps, counted in ⅓ gel volume of each hydrogel droplet (See Methods).

Finally, a large number of single cells was observed in the synthetic ECM that remained viable but did not form enteroids at the evaluation time points of 6-8 days. Additional features of how the enteroid emergence depended on specific cues and timing was investigated, and the properties of the emergent enteroids were further characterized.

Figure 3:
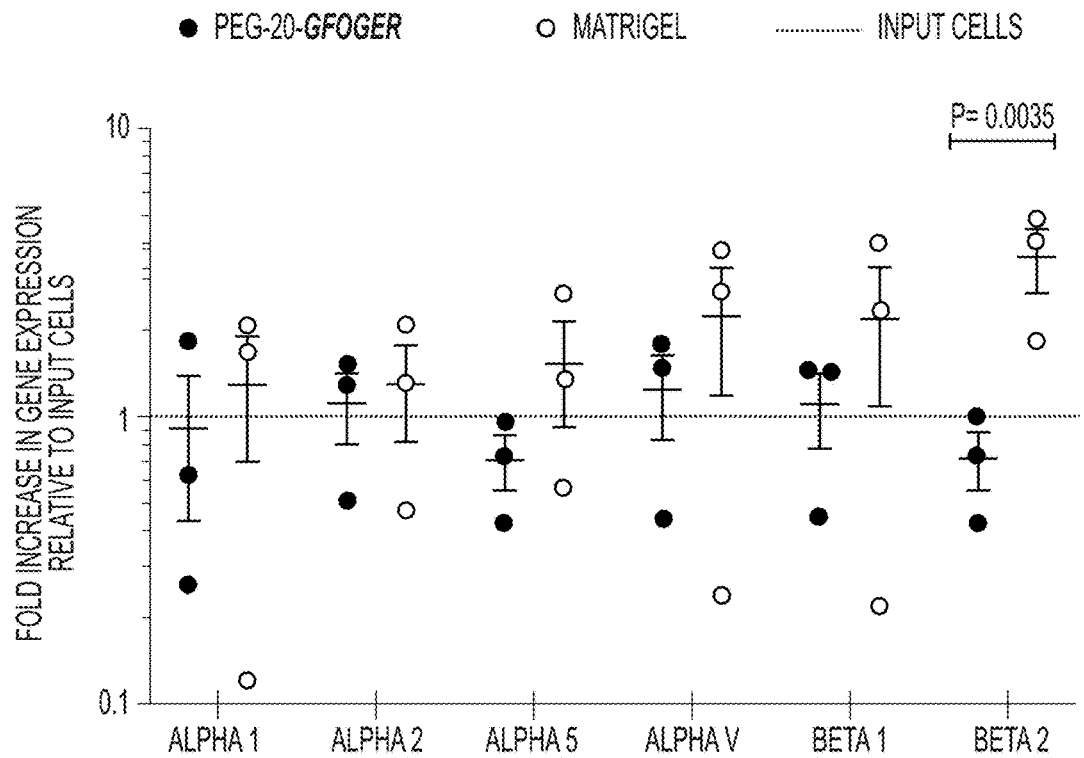
FIG. 3 is a graph showing integrin expression profile of six-day-old enteroids grown in PEG-20-GFOGER and MATRIGEL® relative to cells at the time of encapsulation (day 4). Data from three independent experiments. Data was analyzed using one-way ANOVA with multiple t-tests comparison of the mean.

Enteroid emergence is not strongly correlated with bulk mechanical properties. From the initial panel of 6 synthetic ECMs, those containing GFOGER supported enteroid formation more robustly across all donors compared to those with PHSRN-K-RGD, even though the encapsulated cells expressed integrins for both ligands (i.e., $\alpha 2$, $\alpha 5$, and $\beta 1$ integrins; FIG. 3). Although modest differences in storage modulus and swelling across the synthetic matrices were observed (Tables 8 and 10) bulk mechanical properties were unlikely to be the dominant feature in the advantage of the GFOGER-containing gels in supporting enteroid formation, as the PEG-20-PHSRN-K-RGD and the PEG-20-GFOGER matrices were only 13% different in storage modulus (817±63 Pa and 926±63 Pa, respectively; Table 10 shows no statistical significance between these), yet significant differences in the distribution of enteroid diameters was observed (FIGS. 2A-2B) and enteroid formation efficiency (FIG. 2C).

The frequency of enteroids with diameters above 70 microns was on average only ~10% (range across all donors, 2-21%) of the population counted in the PEG-20-PHSRN-K-RGD, gels compared to 44% (range across all donors, 11-72) in the PEG-20-GFOGER gels (FIGS. 2A-2B). Within the range of parameters tested initially, GFOGER bioactivity was context dependent. Synthetic ECMs with relatively high swelling, lower storage modulus, and longer PEG arms, failed to promote robust enteroid growth in all donors, except for a control donor in which differences in size distribution were not observed (compare PEG-40-GFOGER vs PEG-20-GFOGER in FIGS. 2A, 2B and data not shown). Overall, the frequency of enteroids with diameters above ~70 µm decreased from an average of 44% (range across all donors 11-72%) in the PEG-20-GFOGER to 28% (range across all donors, 3-51%) in the PEG-40-GFOGER. Matrices made with mixed macromers, i.e., PEG-40/20-GFOGER, rescued the bioactivity. This phenomenon of context-dependent success of enteroid formation was not observed in the PEG-PHSRN-K-RGD series, in part because enteroid emergence was relatively poor.

Figure 4A:
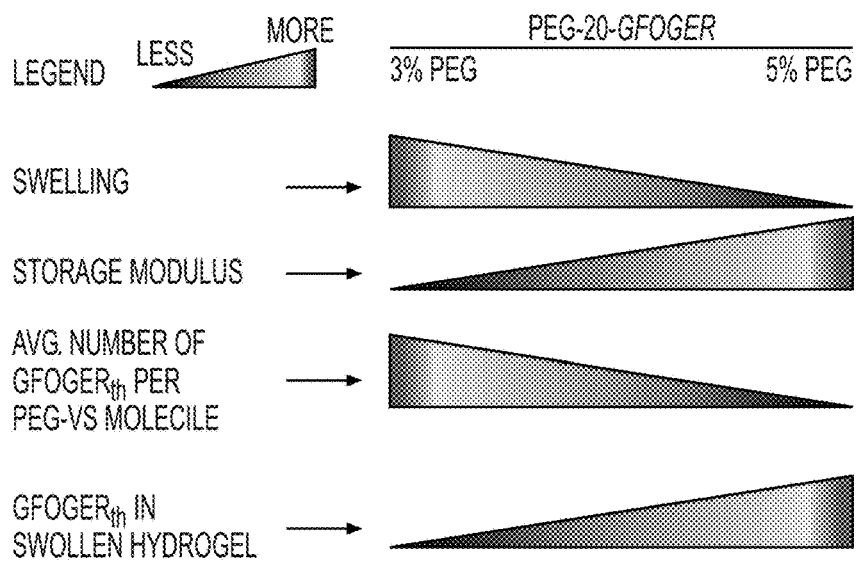
FIG. 4A is a diagram showing a summary of biomechanical changes between 3% and 5% PEG-20-GFOGER matrices made at nominal concentrations of 0.5 mM GFOGERth, 0.25 mM BM-binder, 0.25 mM FN-Binder and 50% XL-MMP-SrtA crosslinker.

To further probe the relationship between enteroid emergence and biomechanical properties, softer gels with the better-performing PEG-20 macromer were created by reducing the macromer concentration to 3% (w/v), and retaining a 50% (of total arm) crosslink ratio. Gels incorporating the preferred ligand, GFOGER, at a nominal concentration of 1.5 mM swelled about 3-fold and were the softest of gels tested (about 100 Pa, Table 8). These changes also altered other gel biophysical properties, including actual ligand concentration of GFOGER/GFOGER$_{th}$ (3% PEG, about 0.5/about 0.17 mM, vs 5% PEG, about 0.75/about 0.25 mM) and the average number of GFOGER$_{th}$ ligands per macromer (3% PEG, 0.33 vs 5% PEG, 0.2) (Table 9). These changes in gel properties are summarized schematically in FIG. 4A.

Figure 4B:
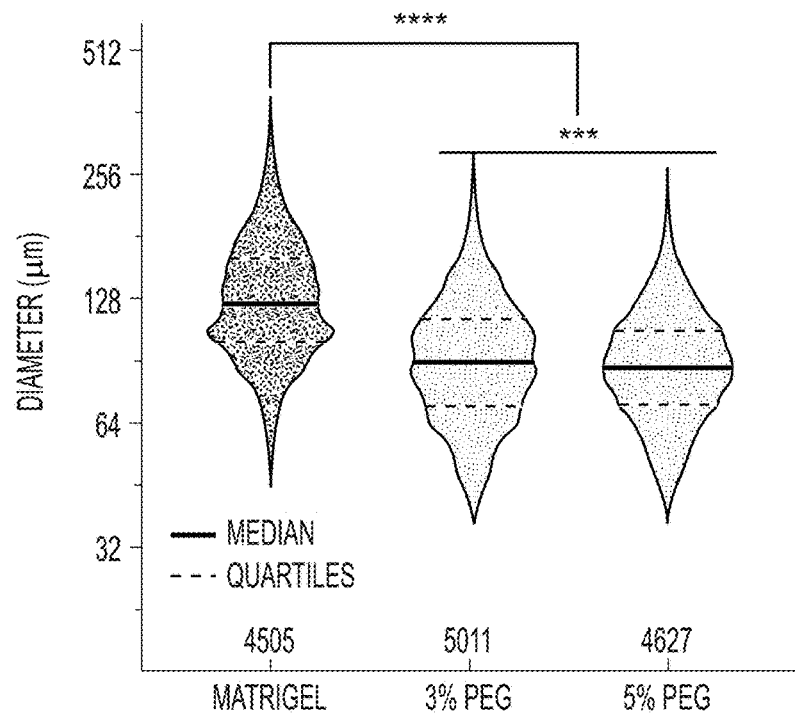
FIG. 4B is a graph showing the enteroid diameter of a duodenal donor (n=2 experiments) in the 3 and 5% PEG matrices.
Figure 4C:
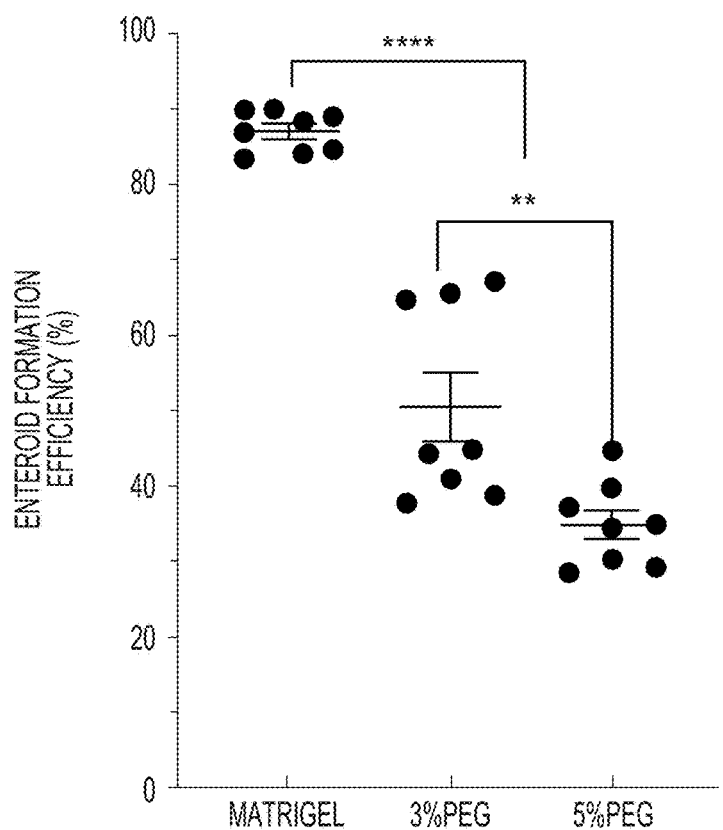
FIG. 4C is a graph showing the effect of PEG concentration (3 and 5%) on enteroid formation efficiency (%) from two independent experiments. Ligand clustering and hydrogel's mechanical properties in the 3% of 20 kDa-PEG provide the highest enteroid formation efficiency. The number of enteroids measured is depicted under each violin plot. Data was analyzed using Kruskal-Wallis multiple comparison of the mean ranks *P=0.0097, P<0.0001. Each symbol in 4C represents a single hydrogel with the mean and SEM. P=0.0025, ****P<0.0001.

When single cells derived from human duodenal enteroids were encapsulated in the 3% PEG-20-GFOGER hydrogels, by 6 days of culture they formed bigger and more abundant enteroids (enteroid median=90 µm) compared to cells encapsulated in 5% PEG-20-GFOGER hydrogels (enteroid median=88 µm), though were smaller than those in MATRIGEL® at the same time point (enteroid median=124 µm; FIG. 4B). Enteroid formation efficiency in the 3% PEG-20-GFOGER hydrogels was 50%, much greater than the value of ~35% in the 5% PEG-20-GFOGER hydrogels but again, still lower than efficiency in MATRIGEL® (~87%) at the same 6-day time point (FIG. 4C).

Collectively, these data show a mechanism for enteroid formation that appears to be dependent on GFOGER, through interaction with α2β1 integrin, and less dependent on the bulk mechanical properties. Although the 3% PEG-20 matrix fostered a significant increase in both enteroid diameter and enteroid formation efficiency, it required gelation times of about 30 minutes, compared to about 15 min for the 5% PEG-20 matrices, and was more sensitive to protocol deviations by individual users. The 5% PEG-20 macromer was selected as the basis of gels for further characterization.

To continue investigating the biophysical context of the GFOGER$_{th}$ peptide on enteroid growth, an additional experiment was set up in which the 5% PEG-20-GFOGER gels were used with a fixed nominal concentration of GFOGER$_{th}$ (0.5 mM) and matrix binders (0.25 mM BM- and 0.25 mM FN-binder) while varying the crosslinker densities across a wide range (35, 40, 45, 50, 55, and 60% XL-MMP-SrtA). This created matrices that swelled 4.4-, 2.8-, 2.5-, 2.0-, 1.7-, and 1.7-fold, from lowest to highest crosslinker densities (FIG. 5B), with corresponding reductions in actual ligand concentrations in swollen gels from the nominal 0.5 mM to values of 0.11, 0.18, 0.2, 0.25, 0.29 and 0.29 mM, respectively. The storage modulus at lower crosslinker densities (35-40%) resulted in relatively soft matrices (~500 Pa) compared to the moderately soft (~850 Pa) matrices produced with 50% crosslinker density, and the relatively stiff (1300 Pa) matrices obtained from the highest crosslinker density, 60% (FIGS. 5A, 5B, and Table 8).

Figure 5A:
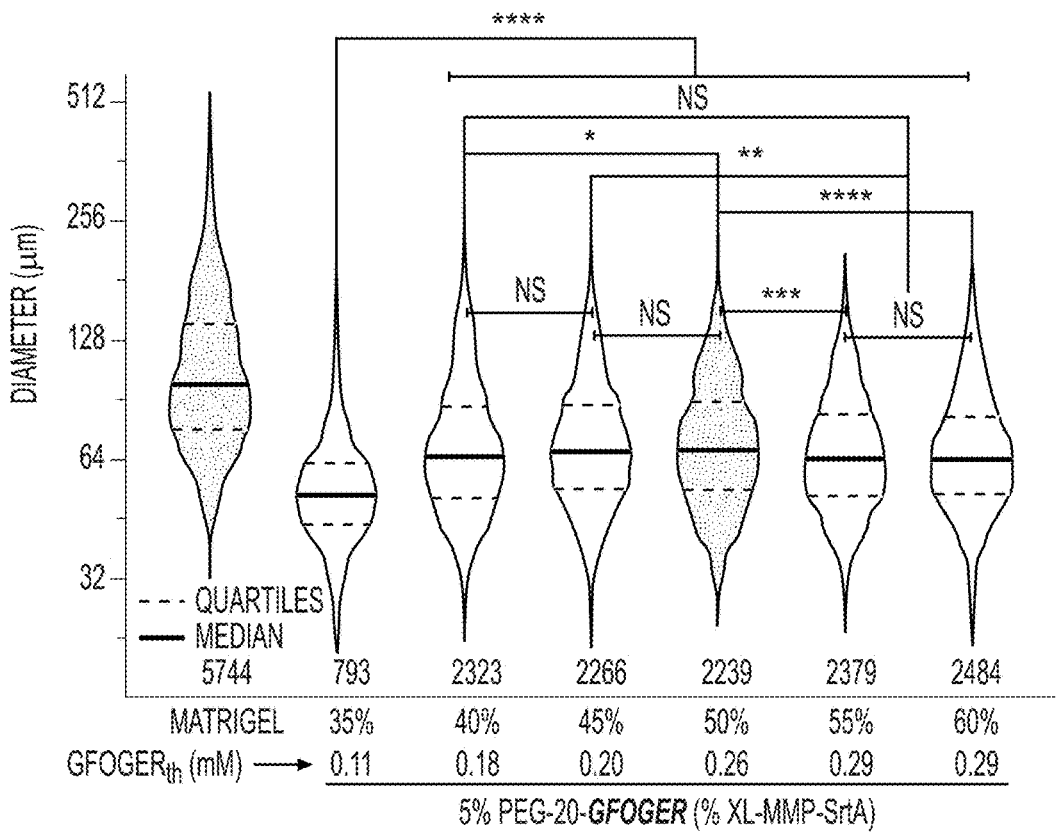
FIG. 5A is a graph showing the effect of crosslinker density (XL-MMP-SrtA) on enteroid diameter. The hydrogels were made at nominal concentrations of 0.5 mM GFOGER$_{th}$, 0.25 mM BM-binder and 0.25 mM FN-binder with the indicated crosslinker density. The concentration of GFOGER$_{th}$ adjusted for swelling at each crosslinker density is indicated. The data is from three independent experiments. The number of six-day old enteroids measured is depicted under each violin plot. The data was analysed using Kruskal-Wallis multiple comparison of the mean ranks. ns: not significant, *P=0.0159, P=0.0076, *P=0.0002, ****P<0.0001.
Figure 5B:
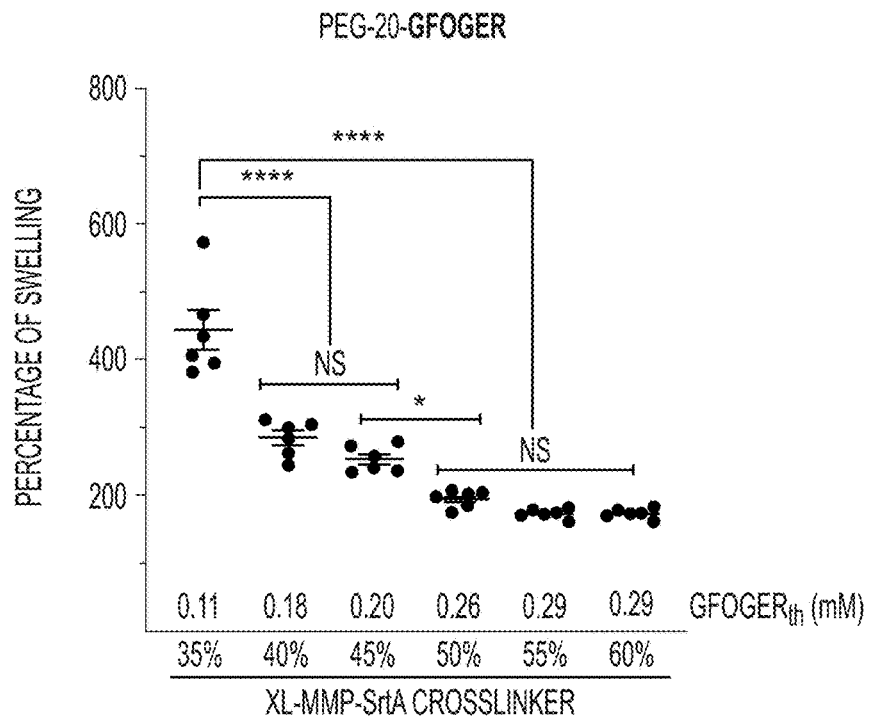
FIG. 5B is a graph showing percent swelling as an effect of crosslinker density (XL-MMP-SrtA) of synthetic matrices made at nominal 0.5 mM GFOGER$_{th}$, 0.25 mM BM- and 0.25 mM FN-binder peptides at the indicated crosslinker density. The triple helical peptide concentration (GFOGER$_{th}$) is shown. Each symbol represents a single hydrogel with the mean and SEM. The data was analysed using one-way ANOVA, Holm-Sidak. ns: not significant, *P=0.0248,****P<0.0001.

Using the enteroid diameter as the proxy for enteroid growth, smaller and less abundant enteroids were observed in the PEG-20-GFOGER matrix made at 35% crosslinker density (enteroid median=52 µm) compared to all matrices tested (FIG. 5A). At 40% crosslinking, the observed enteroid median diameter of 65 µm was comparable to that of 64 µm observed in tighter/stiffer PEG networks crosslinked at 55 and 60% (FIG. 5A). The greatest enteroid median diameters, ~68 µm, where observed at 45% and 50% crosslinker densities, which correspond to 0.20 mM and 0.26 mM of the GFOGER$_{th}$ when adjusted for their corresponding swelling. As observed before, enteroids in MATRIGEL® were significantly bigger (enteroid median=99 µm) than those in the synthetic ECMs, at the same time frame after culture initiation (FIG. 5A).

Ligand biophysical properties are not the dominant feature contributing to organoid growth. The presence of the GFOGER peptide, a ligand for integrin α2β1, is associated with enhanced enteroid formation in PEG-based gels crosslinked with an MMP-degradable peptide and containing matrix-binding peptides. GFOGER also alters other gel properties (Table 8), and in its triple helix form that attains in the gel, GFOGER$_{th}$, may exert unanticipated effects such as sequestration of cell-produced matrix (Lee et al., Biomaterials, 27:5268-5276 (2006)) due to its biophysical properties. To test whether the integrin-binding properties of the GFOGER sequence influence enteroid formation, gels incorporating a ligand with a single amino acid substitution were made, GFOGDR, which still assembles into a triple helix form but does not bind to α2β1 integrins (Knight et al., J. Biol. Chem., 275:35-40 (2000)). Gels based on the PEG-20 macromer incorporating the mutant GFOGDR exhibited mechanical properties similar to those with PEG-20-GFOGER.

Single cells encapsulated in the PEG-20-GFOGDR failed to form enteroids. The majority of cells died after six days of culture. Thus, engaging α2β1 is not only essential for enteroid formation in the context of these minimalistic, PEG-based synthetic ECMs, but also needed to maintain the viability of the population of cells that do not form enteroids observed in the PEG-20-GFOGER matrix.

Figure 6A:
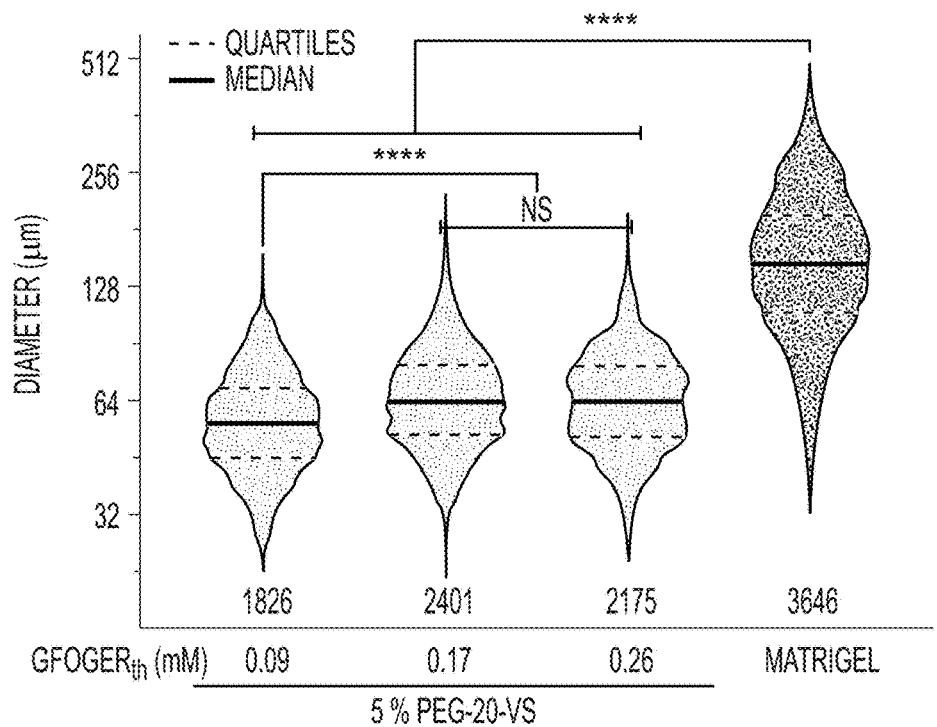
FIGS. 6A and 6B are graphs showing enteroid growth depends on the α2β1 integrin binding peptide, GFOGER. Eeffect of GFOGER dose response on enteroid formation and diameter is shown in FIG. 6A. The hydrogels were formed in matrices with the collective integrin binder concentration of 1.5 mM for the nominal concentration of single helix peptide combinations in each hydrogel (each containing either 0.5 mM GFOGER and 1.0 mM GFOGDR (SEQ ID NO:10), 1.0 mM GFOGER and 0.5 mM GFOGDR, or 1.5 mM GFOGER and 0 mM GFOGDR), and 0.25 mM BM-binder, 0.25 mM FN-binder, and 50% XL-MMP-SrtA crosslinker. The concentration of GFOGER$_{th}$, when adjusted for swelling, is shown on the x-axis. The number of enteroids measured per condition is under each violin plot. Data represent three independent experiments.
Figure 6B:
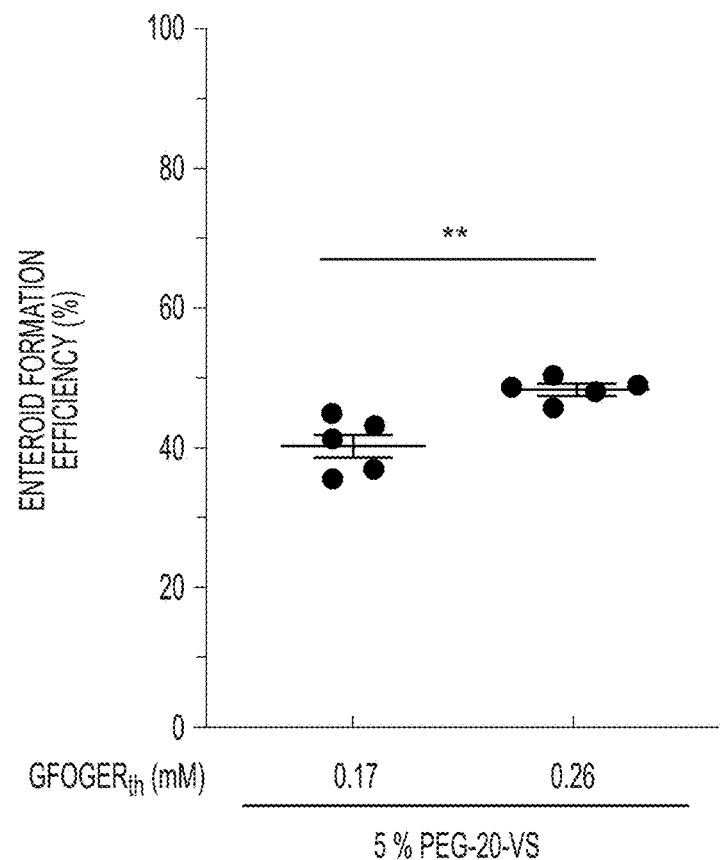

Next, the dependency of enteroid formation was titrated in relation to GFOGER$_{th}$ concentration. First, the active GFOGER$_{th}$ in the gel were systematically diluted through addition of inactive GFOGDR$_{th}$ to keep overall peptide concentrations and biophysical properties constant (FIG. 6A). The PEG-20-GFOGER used in experiments described thus far contains 0.26 mM of GFOGER$_{th}$ and 0.13 mM of BM- and 0.13 mM FN-binder peptides at 50% XL-MMP-SrtA crosslinker when adjusted for the 1.96-fold swelling. A panel of gels with active GFOGER$_{th}$ peptide concentrations of 0.09, 0.17 and 0.26 mM (total triple helical peptide identical at 0.26 mM; all concentrations are values that have been adjusted for swelling) was created with the standard concentrations of 0.13 BM-binder and FN-binder and 50% crosslinking, which resulted in corresponding variation in the average number of active GFOGER$_{th}$ per PEG macromer of 0.07, 0.13 and 0.2. Importantly, these matrices have comparable mechanical properties, thus any differences in enteroid growth can be attributed to differences in GFOGER$_{th}$ concentration. Using the enteroid diameter as a proxy for enteroid growth, a significant increase in the enteroid median diameter was observed when increasing GFOGER$_{th}$ concentration from 0.09 mM (enteroid median=56 µm) to 0.17 mM (enteroid median=64 µm), but no further increase in enteroid median diameter is observed upon further increase to 0.26 mM of GFOGER$_{th}$ (64 µm; FIG. 6A). However, enteroid formation efficiency was higher at 0.26 mM (48%) than 0.17 mM (40%) GFOGER$_{th}$ (FIG. 6B). As observed before, enteroids in MATRIGEL® were significantly bigger (enteroid median=149 µm) than those in the synthetic ECMs, at the same time frame after culture initiation (FIG. 6A).

One interpretation of the superiority of GFOGER compared to PHSRN-K-RGD in fostering enteroid formation is differences in ligand biophysical presentation, arising from differences in ligand accessibility or clustering (FIG. 1F). The triple-helical GFOGER peptide is relatively stiffer and more extended from the PEG polymer arm compared to the shorter configuration of the PHSRN-K-RGD. Ligand accessibility in a hydrogel is also influenced by PEG network structure and the conformation of PEG arms that exist in a coiled conformation in aqueous solution, thus, it is possible that unmodified, free PEG-arms could shield end-grafted ligands, preventing cell-matrix interactions (Salinas et al., *J Tissue Eng Regen Med.*, 2:296-304 (2008); and Lin et al., *Adv. Funct. Mater.*, 19:2325-2331 (2009)). Longer integrin binding peptides may aid in ligand accessibility and longer and clustered ligands may aid in integrin-ligand affinity and avidity. Increasing the RGD-containing ligand accessibility and clustering, while maintaining the bulk mechanical properties constant, was investigated to identify if would result in increased enteroid formation. Three peptides harboring the RGD motif were synthesized: a short linear peptide, RGD; a longer extended linear ligand, G11RGD; and a longer and clustered RGD ligand, CMPRGD (see Table 7 for complete sequences). As control, the PHSRN-K-RGD and GFOGER peptides were included when testing each donor for enteroid behavior in gels containing these modified peptides. The PHSRN-K-RGD peptide is longer than RGD and served as control for the newly designed longer G11RGD. The CMPRGD ligand has a triple helical structure, similar to the GFOGER peptide, thus the properties of the PEG-20-GFOGER and PEG-20-CMPRGD matrices are comparable (FIGS. 7A-7E).

Figure 7F:
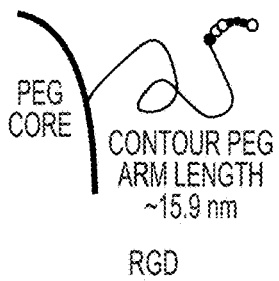
Figure 7F:
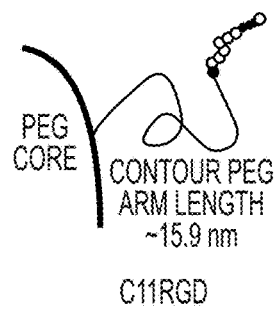
Figure 7F:
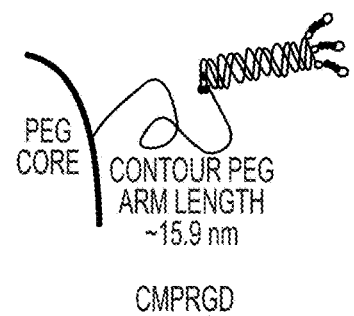
Figure 7F:
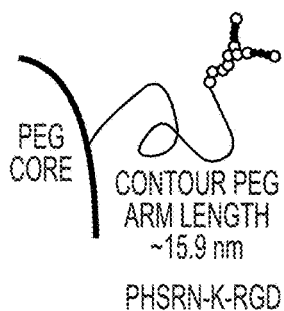
Figure 7F:
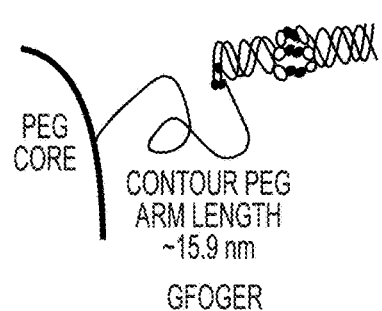
Figure 7F:
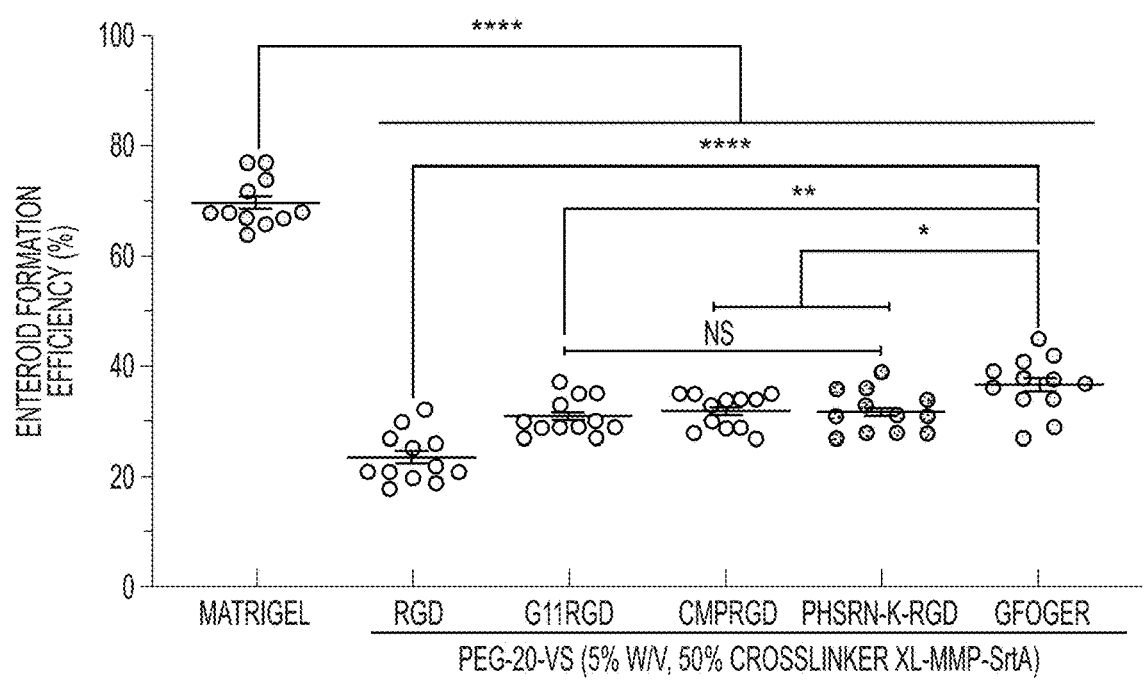
Figure 7G:
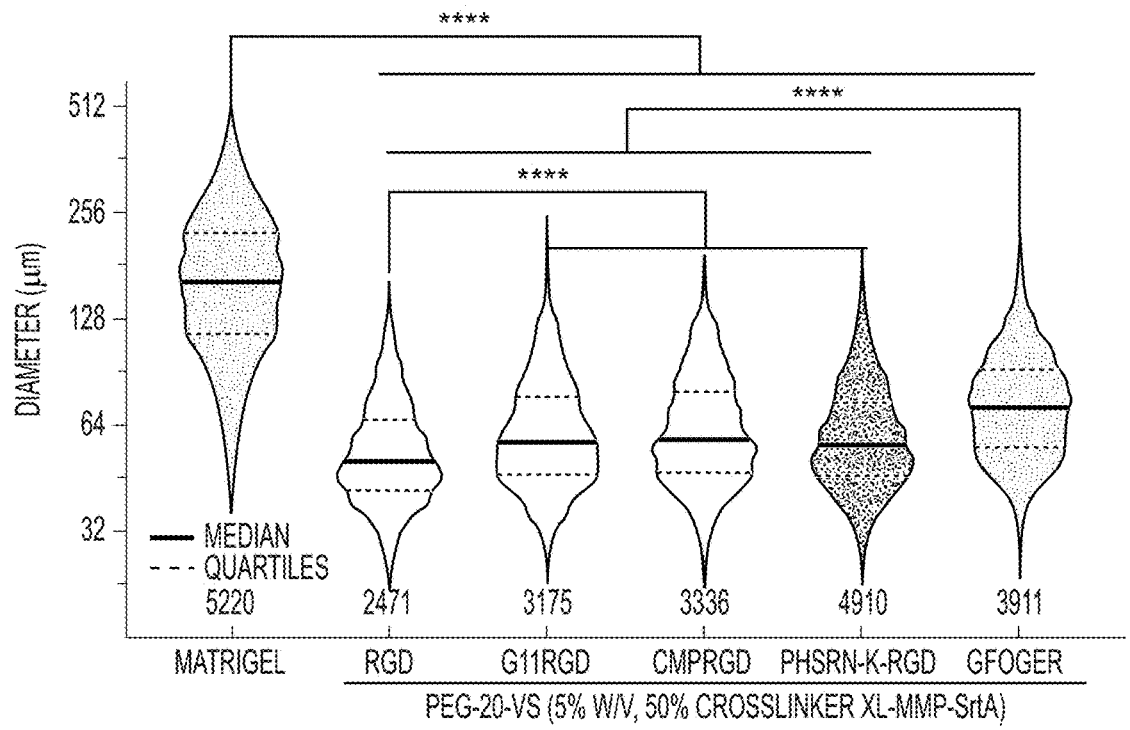

Single cells from a human duodenal organoid donor were encapsulated in the synthetic matrices and cultured for six days in organoid expansion medium. Enteroid formation efficiency and enteroid diameters were higher in matrices made with longer (G11RGD, PHSRN-K-RGD) and clustered (CMPRGD) peptides compared to the short RGD. The median enteroid diameter for RGD, G11RGD, PHSRN-K-RGD and CMPRGD were 43, 50, 47, and 49 µm, respectively, whereas the enteroid formation efficiencies were 23, 31, 31, and 32%, respectively (FIGS. 7G-7H). The similarity of outcomes for the PEG-20-G11RGD, PEG-20-CMPRGD, and PEG-20-PHSRN-K-RGD matrices, which were all greater than values for the shorter RGD peptide, showed that the increase in enteroid diameter and enteroid formation efficiency with the extended RGD peptides are due to ligand accessibility. None of the iterations of RGD-containing peptides, however, improved the synthetic matrix to match the performance of matrices containing the GFOGER peptide, which had the highest enteroid formation (37%) and enteroid diameter (86 µm) (FIG. 7G-7H).

Collectively, the data show that 0.26 mM of GFOGER$_{th}$ is required for robust enteroid growth and efficiency. The 5% PEG-20-GFOGER at 0.26 mM GFOGER$_{th}$ was selected for future experiments.

Enteroid growth in PEG-20-GFOGER gels requires MMP-susceptible crosslinkers. Changes in the nature of the crosslinker have been reported to affect enteroid formation. Mouse ISCs encapsulated in PEG-based hydrogels have been reported to form cyst-like enteroid structures when crosslinked with a non-degradable crosslinker, but ISCs encapsulated in gels with an MMP-sensitive crosslinker develop an irregular shape with some dysregulation of apicobasal polarity (Gjorevski et al., *Nat. Publ. Gr.*, 539: 560-564 (2016)). In synthetic PEG-20-GFOGER matrices, enteroids emerged from single cells in a synthetic ECM crosslinked with a peptide lacking an MMP cleavage site (XL-SrtA, non cell-degradable), but by 6 days were smaller and less abundant compared to enteroids in synthetic ECM made with an MMP-degradable (XL-MMP-SrtA, cell-degradable) crosslinker. This showed that the microenvironment of the synthetic ECM can provide an initial niche for cell proliferation to establish enteroids, but later stages in growth might require simultaneous cell-mediated matrix degradation.

Kinetics of Clonal Enteroid Growth, Morphology Evolution, and Responses to Basal Stimuli. To gain more insights into the growth of human enteroids in the 5% PEG-20-GFOGER, the temporal formation of enteroids from single cells was followed (FIGS. 8A-8C). The effect of whether enteroids observed in the synthetic ECM preserved a clonal nature as they grow over several days, or whether they gradually fuse to former larger enteroids, as observed in MATRIGEL® culture, was examined. Time-lapse live imaging of individual enteroids in intervals from days 2-3 and 4-6 after encapsulation revealed clonal growth in both matrices during this time period, with apparent comparable rates of expansion in MATRIGEL® and synthetic ECM once organoids were established from individual cells. A clear lumen was visible by day three in MATRIGEL® and by day four in the synthetic ECM. By day six, cells that failed to form enteroids were still viable, as analyzed by live-dead staining. Viable single cells that did not form enteroids were observed in multiple different human donors.

As enteroids in the synthetic ECM, on average, had a delayed emergence, the enteroid diameter analysis was extended for up to ten days. Although enteroids in the synthetic ECM continued to emerge and grow (FIG. 8A), the size distribution of the overall population at day 10 did not reach that of the population in MATRIGEL® at day 6. The median enteroid diameter in the PEG-20-GFOGER at day 6, 8 and 10 were 65, 91 and 97 µm. The median enteroid diameter in MATRIGEL® at day 6 was 167 µm. Interestingly, enteroids in MATRIGEL® at days 8 and 10 started to fuse and created a mass of interconnected cells at the bottom of the well accompanied by significant cell death, possibly due to MATRIGEL® degradation and dissolution. This phenomenon was not observed in the synthetic ECM, which is an important feature for long-term culture and potential applications of organoids.

Time-lapse live cell imaging from day 4 to 6 both confirmed the clonal nature of growth, and also revealed a striking pulsing growth rate of the enteroid diameters, showing fluid pressure oscillations (Ruiz-Herrero et al., *Development*, 144(23):4422-4427 (2017); and Dasgupta et al., *Proc. Natl. Acad. Sci.* 115:E4751-E4757 (2018)). Enteroids in MATRIGEL® had relatively variable, low-amplitude pulses occurring over 4-9 hr, compared to pulses in synthetic ECM, which had more regular, sharp, high amplitude pulses approximately every 7 hr. Time-lapse live cell imaging also captured epithelial cells being extruded into the lumen in MATRIGEL® and the synthetic ECM, showing the establishment of a functional and polarized epithelial layer (FIGS. 8B and 8C). These emergent enteroids retained proper polarization across multiple donors as evidenced by apical localization of actin.

Properly polarized and functional organoids can be used to study adaptive epithelial responses. To test if enteroids in the synthetic ECM were functionally responsive to basolateral stimulation, six-day old enteroids were treated with prostaglandin E2 ($PGE_2$) and forskolin (FKL). $PGE_2$ and FKL have been shown to induce rapid morphological changes characterized by an increase in organoid diameter (Boj et al., J. Vis. Exp., (120):55159 (2017)). After six hours of $PGE_2$ and FKL treatment, a 1.2-fold increase in diameter of the overall enteroid population with $PGE_2$ and 1.5-fold increase in enteroid diameter on the overall population with FKL in enteroids grown in the PEG-20-GFOGER was observed. These results are comparable to the fold increase in enteroid diameter of organoids grown in MATRIGEL®, 1.4-fold for $PGE_2$ and 1.5-fold for FKL after treatment (FIGS. 8D and 8E). This increase in diameter is independent of cell proliferation as enteroids treated with $PGE_2$ and FKL increased in size rapidly and did not follow the typical oscillation growth observed before.

This response showed that the synthetic ECM not only supported functionally responsive enteroids but was also flexible enough to accommodate a rapid increase in enteroid size that was independent of matrix degradation.

Undifferentiated enteroids in the synthetic ECM express crypt markers and retain their proliferative capacity across passages. Epithelial organoids can be cultured continuously due to an undifferentiated stem cell population that, when re-embedded in MATRIGEL®, gives rise to new organoids (Sato et al., Gastroenterology, 141:1762-1772 (2011)). The stem cell population in vitro, like that in vivo, is interspersed with Paneth cells that engage in metabolic cross talk with stem cells and produce WNTs and other growth factors necessary for stem cell maintenance (Date et al., Annu. Rev. Cell Dev. Biol., 313221:1-32 (2015); and Rodriguez-Colman et al., Nature, 543:424-427 (2017)). Thus, to characterize the duodenal enteroids in the synthetic ECM with respect to this and other canonical crypt phenotypes, organoids were labeled with 5-ethynyl-2'-deoxyuridine (EdU) to identify proliferative cells, then performed immunostaining to identify Paneth cells via staining for lysozyme (Lyz). Frequent adjacent EdU+ and Lyz+cells were observed in enteroids grown in MATRIGEL® and synthetic ECM in both a normal duodenal donor and a Crohn's donor. The juxtaposition of EdU+ and Lyz+cells shows a Paneth cell-stem cell arrangement. These proliferative enteroids also exhibited positive staining for E-cadherin and villin, typical pan-crypt markers for intestinal epithelial cells. Collagen IV, a basement membrane protein, and CD44-v6, a hyaluronic acid receptor variant expressed at the bottom of the crypt were also detected in enteroids growing in the synthetic ECM.

Figure 9A:
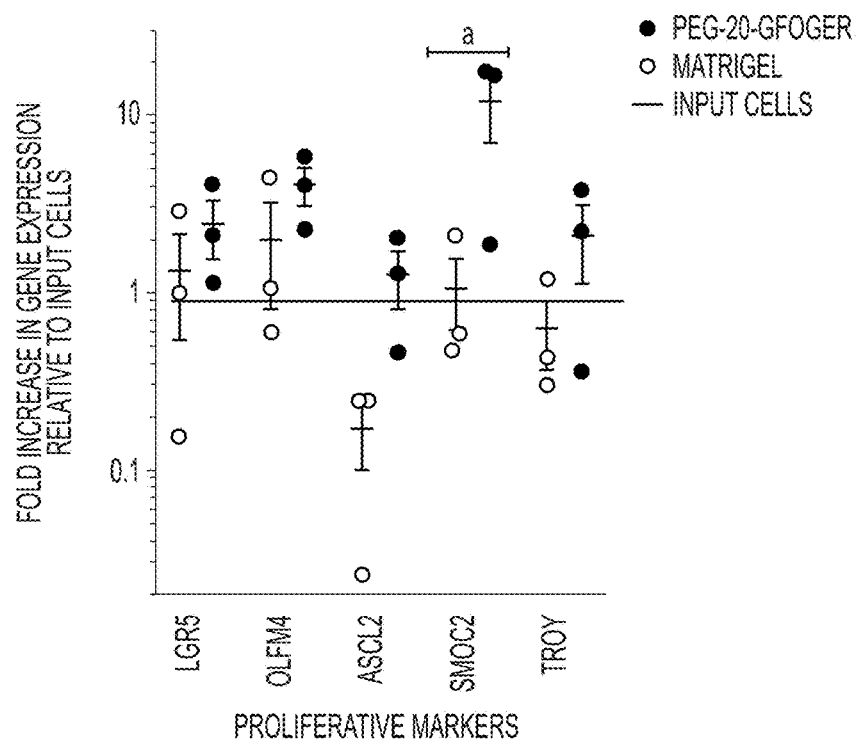
FIGS. 9A-9C are graphs showing fold change in gene expression of six-days old enteroids in the synthetic ECM or MATRIGEL® relative to cells at the time of encapsulation (day 4). Data from three independent experiments. a—P=0.0003, b—P=0.00053 using multiple t-test comparison of the mean. The PEG-20-GFOGER hydrogels was made at 0.5 mM GFOGERth, 0.25 mM BM-binder, 0.25 mM FN-binder and 50% XL-MMP-SrtA.
Figure 9B:
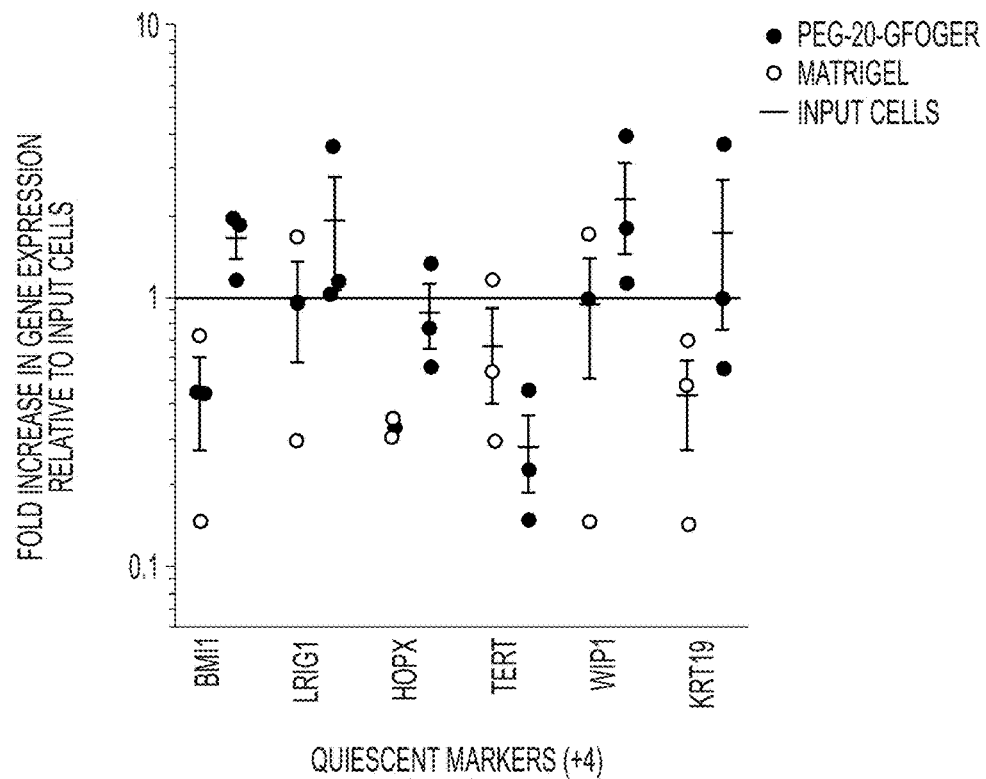
Figure 9C:
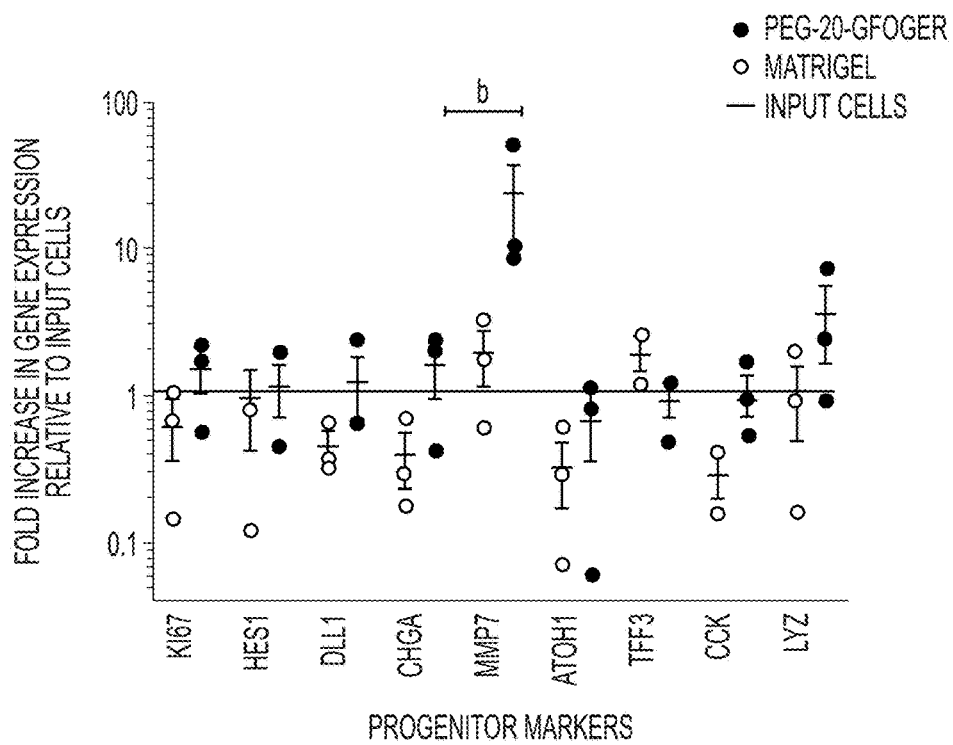

The phenotypes of cells in enteroids was investigated by quantitative PCR (qPCR) for five genes associated with active stem cells (LGR5, OLFM4, ASCL2, SMOC2, TROY), six genes associated with the +4 quiescent stem cells (BMI1, LRIG1, HOPX, TERT, WIP1, KRT19) and nine genes associated with progenitor cells (KI67, HES1, DLL1, CHGA, MMP7, ATOH1, TFF3, CCK, LYZ). Enteroids were harvested from two duodenal donors (one unaffected, and one Crohn's disease) cultured in either synthetic ECM or MATRIGEL® on day six and compared gene expression of these harvested enteroids to that of cells at the time of encapsulation, which had been derived from day four organoids in MATRIGEL®. In the non-diseased donor, although expression of most genes trended higher for enteroids in the synthetic gel (often due to repressed expression in MATRIGEL® relative to baseline, as best exemplified by the active stem cell marker ASCL2), only the active stem cell marker SMOC2 and the progenitor marker MMP7, a gene highly expressed in Paneth cells (Tong et al, Cell Stem Cell., 23:46-59.e5 (2018)) showed significant differences between MATRIGEL® and the synthetic ECM, with greater expression for both in the synthetic ECM and enhanced more than 2-fold beyond the baseline (FIGS. 9A-9C). Immunostaining analysis of six-day old enteroids in the PEG-20-GFOGER and MATRIGEL® also showed proliferative cells (EdU), Paneth cells (Lyz), epithelial markers (E-cad and Villin) and basolateral markers (C-IV and CD44-v6).These findings may reflect a more delayed growth pattern in synthetic gels, and the enrichment may be attributed to the relative abundance of single, viable cells in the synthetic ECM compared to MATRIGEL® at this time point.

Enteroids from the Crohn's donor in general showed more variability among expression levels for each gene, and only the progenitor marker ATOH1 was significantly different in the two conditions, expressed at much higher levels in MATRIGEL®. Immunostaining analysis of six-day-old enteroids in the synthetic ECM and MATRIGEL® showed proliferative cells (EdU), Paneth cells (Lyz), and epithelial markers (E-cad and Villin).

As enteroids in the synthetic ECM appear to retain a similar gene expression profile to enteroids in MATRIGEL® including enhanced expression of some stem cell markers, they contained a proliferative cell population capable of forming new enteroids when dispersed into single cells, then encapsulated in either a new synthetic ECM or MATRIGEL®. Six-day old enteroids were collected from the synthetic ECM and then processed (see Methods) to generate single cells to re-embed into new synthetic ECM or MATRIGEL®. This procedure was performed for three consecutive passages with the two duodenal donors (FIG. 10 and data not shown). Quantification of the total number of cells recovered at each passage after 6 days of culture in the synthetic ECM revealed a 1.5 to 2-fold increase in cell number relative to the initial number of encapsulated cells (FIG. 11). As described before, a population of cells that failed to form enteroids but remained viable was also noted. This cell population was also included in the calculation of fold increase in FIG. 11. Interestingly, when single cells from enteroids grown in the synthetic ECM were embedded in MATRIGEL®, they emerged and formed enteroids similarly to cells retrieved from MATRIGEL®: cells from both the control and the Crohn's donor formed enteroids with high efficiency, doubling in diameter every 2 days; enteroids emerging in the synthetic ECM double in diameter every 4 days. The delayed growth in the synthetic matrix preserved the enteroids in an immature state (stem cell enrichment) as trends for greater expression of proliferative gene markers by qPCR was noted (FIGS. 9A-9C). The robust proliferation of cells harvested from the synthetic ECM and transferred back into MATRIGEL® showed the cells that did not form enteroids in synthetic ECM retained their proliferative capacity, and were stimulated by the permissive environment of MATRIGEL® and perhaps by additional growth factors present in MATRIGEL® (Bankaitis et al., Gastroenterology, 155:1348-1361 (2018); and Ayyaz et al, Nature, 569:121-125(2019)). This observation furthers highlighted the significance of developing a suitable matrix to uncover biological processes in epithelial organoids masked when using ill-defined MATRIGEL® hydrogels.

Quantification of enteroid diameters after each passage further revealed a wide range of sizes in the population, but similar to previous results, enteroids in MATRIGEL® were, on average, bigger than those in the synthetic ECM. The enteroid median diameters of the duodenal control donor were 78, 75, and 72 µm at each passage in the synthetic ECM, whereas in MATRIGEL® the median diameters were 137, 151 and 127 µm. The enteroid median diameters of the duodenal Crohn's donor were 73, 82, and 60 µm at each passage in the synthetic ECM, whereas in MATRIGEL® the diameters were 103, 123 and 91 µm. The wide range in enteroid diameters showed that enteroids recovered from the synthetic ECM, similar to those recovered from MATRIGEL®, contain a population of cells that vary in their proliferative capacity.

Partial removal of stem cell factors induces a differentiation phenotype in enteroids maintained in synthetic ECM. Stem-enriched enteroids in MATRIGEL® undergo differentiation when switched to differentiation medium (DM) lacking Wnt3a, a ligand for the Frizzled receptor that enhances the activity of the LGR5 ligand, R-spondin1, in LGR5-positive ISCs, or DM made with lower concentrations of L-WRN (Wnt3a, R-spondin1 and Noggin) conditioned medium (L-WRN-DM) (Sato et al., *Gastroenterology*, 141:1762-1772 (2011); and VanDussen et al., *Gut*, 64:911-20 (2015)). Stem-enriched mouse enteroids grown in a synthetic ECM, in contrast, undergo rapid cell death upon switching to DM, due to a rapid loss of resident stem cells (Gjorevski et al., *Nat. Publ. Gr.*, 539:560-564 (2016)). The culture medium cues were modulated in order to preserve a pool of stem cells while allowing the emergence of differentiated cells when cells cultured in the minimal synthetic ECM (5% PEG-20-GFOGER). Human enteroids were differentiated using L-WRN conditioned medium at half the concentration used for human enteroid expansion. Human duodenal and colon enteroids were grown for six days in EM (50% L-WRN) then switched to L-WRN-DM (25% L-WRN) or DM. Removal of Wnt3a (DM) caused rapid cell death of human enteroids that was not observed in enteroids differentiated in MATRIGEL®. When human enteroids grown in the 5% PEG-20-GFOGER for six days in expansion medium were switched to L-WRN-DM they adopted diverse phenotypes with some enteroids showing typical hallmarks of differentiation (thick columnar cells and accumulation of apoptotic cells in the lumen), and in some instances adopting folded 3D structures. Bright-field images of 10-day old human enteroids growing in the PEG-20-GFOGER matrix or MATRIGEL® showed diverse phenotypes upon inducing differentiation. In MATRIGEL®, a similar phenotype was observed when switched to DM. Likewise, mouse intestinal enteroids in the synthetic ECM also showed hallmarks of differentiation.

To further characterize the differentiated organoids emerging in the PEG-20-GFOGER matrix, immunostaining analysis of organoids from a human duodenal control donor was performed, a human duodenal Crohn's donor and a human colon control donor. The presence of proliferative cells by Ki67 staining or EdU labeling was confirmed. Proliferative cells were present in differentiated organoids in the three donors analyzed, but, as expected, were less frequent than number of proliferative cells observed in the undifferentiated enteroids, which showed than the proliferative cells observed in the undifferentiated enteroids underwent differentiation upon reduction of the Wnt3a concentration. Likewise, a reduction in the number of proliferative cells in organoids grown in MATRIGEL® upon switching to differentiation medium was observed.

In addition to proliferative cells, Lyz+cells (Paneth cells) were also detected in the differentiated organoids in the two duodenal donors, in both the synthetic ECM and MATRIGEL®. These differentiated duodenal organoids also exhibited positive staining for E-cadherin and villin, typical markers for intestinal epithelial cells. Mucus producing goblet cells (Muc2 immunostaining) were identified in the human duodenal control donor grown in the synthetic ECM, characteristic of the more mature luminal cells. Further, immunostaining also detected markers of mature enterocytes: dipeptidyl peptidase IV (DPPIV) in the colon donor, in both MATRIGEL® and the synthetic ECM, and $Na^+/H^+$ exchanger 3 (NHE3) in the three donors (two duodenal and one colon), in both MATRIGEL® and the synthetic ECM. Immunostaining analysis of 10-day old organoids in the PEG-20-GFOGER and MATRIGEL® showed proliferative cells (Ki67, EdU), S secretory cells, (Paneth cells (Lyz) and Goblet cells (Muc2)). Epithelial marker (E-cad), and enterocyte mature markers (NHE3) and basolateral markers (CD44v6, C-IV, and LMN).

Apico-basolateral markers in the three donors were analyzed. Actin was detected in the apical side in the colon organoids grown in the synthetic ECM and MATRIGEL®. Likewise, apical actin was detected in the two duodenal donors in organoids grown in MATRIGEL® or the synthetic ECM. Collagen IV and Laminin, basement membrane proteins, and CD44-v6, a hyaluronic acid receptor variant expressed at the bottom of the crypt were also detected in the two duodenal organoids growing in the synthetic ECM. Accumulation of basement membrane proteins Collagen IV and LMN produced by the epithelial cells showed formation of a basement membrane that offers a richer ECM signaling compared to the defined short adhesion peptides. In summary, the data showed that enteroids emerging in the synthetic ECM were composed of stem cells that underwent early stages of differentiation (prior to crypt morphogenesis) to a similar extent as enteroids emerging in MATRIGEL®. This process was reproducible as shown by using two duodenal donors and one colon donor.

Synthetic ECM Supports Human-Derived Endometrial Organoid Culture.

The endometrium is a highly dynamic mucosal barrier tissue which sheds about 1 cm of glandular and luminal epithelia along with supporting stroma each month and then regenerates the tissue from remaining pools of stem and progenitor cells. Regeneration and growth is primarily fueled by estradiol, and tissue differentiation processes (i.e. decidualization) commences upon the onset of progesterone after ovulation. A study to include human endometrial organoids was conducted, as they exhibit many similarities to intestinal organoids when cultured in MATRIGEL®: a single layer of epithelium surrounding a lumen; strongly proliferative in a culture medium favoring stem cells; responsive to differentiation cues; robust to serial passage for 5+ months without changes in DNA; and robust recovery after a freeze/thaw cycle.

Organoids were established derived from endometrial biopsies obtained from the stratum functionalis of human donors. In comparison to intestine, the endometrial stem cell compartment is relatively poorly defined, and the tissue exhibits dramatic steroid hormone responses. One study using in situ hybridization for LGR-5 RNA showed that the endometrium potentially has stem/progenitor pools in the functionalis region of the endometrium, from which the donor tissue was harvested, throughout the menstrual cycle. The geographical location of putative stem/progenitor cell compartments aids selection of synthetic ECM components in light of reported integrin expression profiles in the endometrium. Integrin α2β1 is expressed throughout all phases of the menstrual cycle and is strongly expressed in luminal and glandular epithelia, thus motivating the inclusion of the GFOGER peptide. The RGD-binding vitronectin receptor, integrin αvβ3, has an unusual cyclical expression profile. In healthy women, it is expressed in mid-secretory phase throughout implantation and may play a role in embryo implantation. Its expression in the endometrial organoids would not be expected due to control over sex hormone concentrations in the in vitro model. While it is well-established that the endometrial stromal cells express the canonical fibronectin-binding receptor, integrin α5β1, its expression in the epithelia is controversial. Integrin α6, which functions as a LMN receptor when paired with β1 or β4, is expressed in basolateral fashion throughout the endometrium in proliferative and secretory phases. A screen of ECMs containing PEG-20-GFOGER, PEG-20-PHSRN-K-RGD, PEG-20-RGD, PEG-20-G11RGD, and PEG-20-CM-PRGD yielded a formulation suitable for culture of endometrial organoids.

Figure 12:
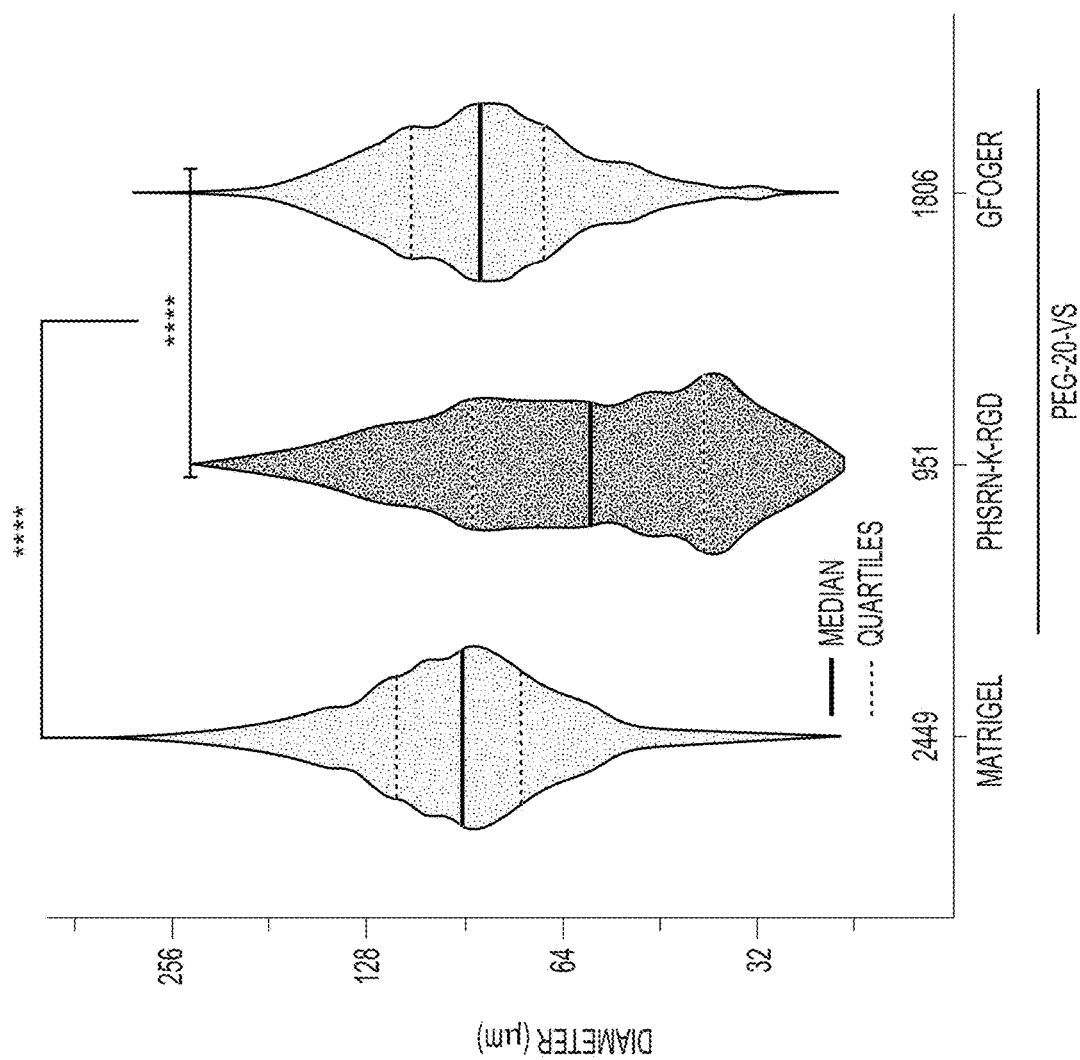
FIG. 12 shows human endometrial organoids can be cultured in synthetic ECMs. The hydrogels were made at 5% PEG-20 with nominal concentrations of 1.5 mM integrin binder peptide, 0.25 mM BM-binder, 0.25 mM FN-binder and 50% XL-MMP-SrtA crosslinker. The diameter (μm) of eight-day old endometrial organoids (n=2 independent experiments) growing in the synthetic matrices is shown. ****$P<0.0001$, using Kruskal-Wallis multiple comparison of the mean ranks. The number of organoids measured per ECM condition is depicted under each violin plot.

Single cells obtained from dissociation of endometrial organoids were embedded in the synthetic ECMs, where they proliferated and formed lumenized cystic organoids with thick columnar cells. Among the formulations tested, the best synthetic ECM formulation for supporting robust growth of polarized endometrial organoids was identical to the best synthetic ECM for enteroids (FIG. 12). Similar to intestinal enteroids, endometrial organoids in MATRIGEL® appeared larger and more abundant than organoids in the synthetic matrices eight days after encapsulation. In the PEG-20-GFOGER, the organoid median diameter was 85 μm, compared to 58 μm for the PEG-20-PHSRN-K-RGD. In MATRIGEL® the median diameter was 91 μm (FIG. 12). Approximately 38% of all endometrial organoids counted in the PEG-20-GFOGER matrix reached sizes above 90 microns, compared to 21% in the PEG-20-PHSRN-K-RGD. Both synthetic ECMs, however, were lower than MATRIGEL® in which 46% of the organoid population reached diameters above 90 microns (FIG. 12). Finally, endometrial organoids, in the PEG-20-GFOGER matrix, showed proliferative cells (EdU), epithelial EpCAM, apical actin, and basal LMN deposition similar to those grown in MATRIGEL®. Immunostaining analysis of organoids in the PEG-20-GFOGER matrix made at 1.5 mM (0.5 mM GFOGERth), 0.25 mM BM-binder, 0.25 FN-binder and 50% XL-MMP-SrtA crosslinker, showed proliferative cells (EdU), apical markers (actin), epithelial marker (EpCAM), and basolateral marker (LMN). Collectively, these data showed that a defined intestinal formulation of a synthetic hydrogel can be applicable to additional epithelial-rich tissues.

In summary, a fully synthetic ECM was developed that supported growth and serial passaging of primary postnatal human enteroids derived from the upper and lower intestinal track and primary human postnatal endometrial epithelial organoids, starting with single cells. This synthetic ECM also supported culture of mouse enteroids. In the context of this minimal synthetic ECM, incorporation of the collagen-derived peptide recognized by integrin α2β1, GFOGER (which self assembles into the triple helix GFOGER$_{th}$) provided a robust growth of organoids from individual cells. Gels incorporating an MMP-sensitive peptide crosslinker were significantly more effective in fostering enteroid emergence and growth than gels incorporating a crosslinker that could not be remodeled by cellular action.

The dependence of human enteroid emergence on the presence of GFOGER, which exists in the gel as the triple helix GFOGER$_{th}$, was evident from experiments using an inactive variant, GFOGDR$_{th}$. The GFOGDR$_{th}$ variant is known to abolish integrin α2β1 binding (Knight et al. *J. Biol. Chem.* 275:35-40 (2000)). Titration of the active GFOGER$_{th}$ moiety with inactive GFOGDR$_{th}$ to compare gels with identical biophysical properties but different biochemical properties further established reliance on this peptide as an active gel constituent, with maximal effectiveness at the maximum tested concentration of 0.5 mM GFOGERth (1.5 mM GFOGER).

Human enteroids emerged more efficiently and achieved larger diameter distributions when a degradable crosslinker was used, compared to a non-degradable crosslinker. Interestingly, the enteroids in the synthetic ECM had significantly greater expression of MMP-7, a marker of Paneth cells (FIG. 9C). The degradation susceptibility did not appear to influence enteroid fusion, a problem noted in MATRIGEL®, as clonal growth and distinct enteroids were observed via time lapse video microscopy and other images at different time points.

There are several notable similarities and differences between the growth, gene expression, and phenotypic behaviors of cells cultured in the preferred synthetic ECM (5% PEG-GFOGER) and those cultured in MATRIGEL®, and these inform the potential uses of this synthetic ECM. Enteroid and organoid emergence from single cells in synthetic ECM was generally less efficient than in MATRIGEL® (FIGS. 2C, 4C, and 6B), where efficiency is defined as the percentage of enteroids with a clear lumen relative to the total number of enteroids, single cells, and cell clumps at the chosen time point. Efficiencies for individual donors varied 28-48% in synthetic ECMs, compared to 71-89% for MATRIGEL®. Abundant viable single cells were observed in synthetic ECM cultures at time points 6 days and later, and the proliferative potential of these single cells is shown by the prolific expansion of cells passaged from the synthetic ECM back into MATRIGEL® (FIG. 11). Cells derived from dissociated enteroids have a spectrum of different phenotypes, resulting in a functionally heterogeneous population at the time of single cell encapsulation, thus requiring a spectrum of different cues in order to stimulate proliferation and enteroid formation from the single cell state. MATRIGEL® provides hundreds of additional matrix and growth factor cues compared to synthetic ECM, and thus contains sufficient cues to stimulate almost the entire cell population at the time of encapsulation. For example, MATRIGEL® contains full-length LMN for engagement of integrin α6β4, which is implicated in proliferation of intestinal crypt cells. The synthetic ECM does not explicitly contain LMN-derived cues, though cell-produced LMN accumulates at the basolateral surface of enteroids as the enteroids and organoids grow in synthetic ECM. The synthetic ECM thus stratifies the starting cell population into a group that remains in limbo, unable to respond to the minimal cues offered by the combined ECM and culture medium-derived growth factor cues in the microenvironment, and a highly proliferative, enteroid-forming group. This stratification property of the synthetic ECM may be a useful feature in parsing plasticity of human intestinal stem cells, as the synthetic ECM can be gently dissolved with SrtA to recover the two cell populations intact for downstream transcriptomics at single cell resolution.

Once enteroids emerge in synthetic ECM, their properties appear similar to enteroids in MATRIGEL®. Enteroids and endometrial organoids in synthetic ECM exhibit proper apical-basolateral polarity, which is an important finding, as enteroids in the absence of a supportive and biologically functional matrix can acquire reverse polarity (apical-out). Enteroids in the synthetic ECM exhibit a similar distribution of proliferative and more differentiated cell types compared to MATRIGEL®. Their phenotypic similarity is also shown by gene expression analysis (FIGS. 9A-9C), which for the synthetic ECM case is dominated by enteroid expression as the total number of cells in enteroids far exceeds the individual cells at the time point of harvest. Likewise, endometrial organoids show a population of proliferative cells and markers for mature differentiated cells in both MATRIGEL® and the synthetic ECM.

One additional phenotypic difference between enteroids in the synthetic ECM and MATRIGEL® is their responses to withdrawal of WNT to induce differentiation into intestinal or colonic organoids. Unlike enteroids in MATRIGEL® that undergo differentiation upon complete withdrawal of Wnt (while preserving Rspo1 and Noggin), enteroids emerging in the synthetic ECM underwent fast apoptotic cell death upon Wnt withdrawal. Using a lower concentration of Wnt the differentiation of enteroids emerging in the synthetic ECM was achieved. With the reduced-Wnt protocol immunostaining of cell-specific and apico-basolateral markers demonstrated that the proliferative cells observed in undifferentiated enteroids undergo differentiation to similar extent as organoids emerging in MATRIGEL®. As enteroids underwent differentiation a switch from globular cyst-like morphology to thicker columnar cysts was observed and in some cases with twisted and folded morphology, in both MATRIGEL® and the synthetic ECM.

A fully synthetic matrix is described that supports primary, human tissue-derived, enteroids from the upper and lower intestinal track and primary, human tissue-derived, endometrial epithelial organoids. The local biophysical presentation of an α2β1 integrin-binding peptide (GFOGER) in the presence of peptides that sequester cell-produce ECM appear as the dominant variables governing epithelial cell proliferation and organoid formation in PEG-based synthetic ECMs. While the synthetic matrix does not match MATRIGEL® benchmarks by some metrics (rate of human organoid emergence and overall proliferation over 6-8 days), it is superior to MATRIGEL® by other metrics, in applications that require (i) a rigorously defined microenvironment to interrogate basic human stem cell biology; (ii) long-term growth of human organoids beyond 6 days; and (iii) in vivo human applications where MATRIGEL® would violate GMP protocols.

The synthetic ECM offers additional benefits such as on-demand dissolution to recover intact organoids and other co-cultured cells for in depth omics analysis and downstream cell-secreted metabolites quantification. This feature is of great utility to uncover complex and dynamic cell-cell communications in emerging stromal-epithelial co-culture systems.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize or be able to ascertain using no more than routine experimentation, many equivalents to the specific embodiments of the invention described herein. Such equivalents are intended to be encompassed by the following claims.

---

We claim:

1. A biodegradable synthetic hydrogel cell culture matrix comprising: branched synthetic polymers and binders bound via a vinyl sulfone linkage to the branched synthetic polymers, the binders comprising both the amino acid sequence GFOGER (SEQ ID NO: 1) in a nominal amount of between about 1.5 mM and 5 mM of synthetic hydrogel cell culture matrix at the time of crosslinking and one or more extracellular matrix or integrin peptide binder.

2. The synthetic hydrogel cell culture matrix of claim 1, wherein the branched synthetic polymers comprise one or more polyalkylene glycols.

3. The synthetic hydrogel cell culture matrix of claim 2, wherein the polyalkylene glycol is one or more polyethylene glycol having a molecular weight between about 2 kDa and about 100 kDa.

4. The synthetic hydrogel cell culture matrix of claim 2, wherein the polyalkylene glycol polymers are 4, 6, or 8-arm branched polyalkylene glycol polymers.

5. The synthetic hydrogel cell culture matrix of claim 1, wherein the molar ratio of the GFOGER (SEQ ID NO:1) binders to the extracellular matrix or integrin peptide binder is greater than 1:1.

6. The synthetic hydrogel cell culture matrix of claim 1, comprising one or more extracellular matrix or integrin peptide binders at a molar ratio between about 2:1 and about 5:1.

7. The synthetic hydrogel cell culture matrix of claim 1, wherein the one or more extracellular matrix or integrin peptide binders comprise amino acid sequence PHSRN (SEQ ID NO:2), RGD, GCRG (SEQ ID NO: 3), and combinations thereof.

8. The synthetic hydrogel cell culture matrix of claim 1, wherein the peptide binder is an extracellular protein-binding peptide comprising $NH_2$-GCRE-ISAFLGIPFAE-PPMGPRRFLPPEPKKP(Am) (SEQ ID NO:4) and $NH_2$-GCRE-TLQPVYEYMVGV-COOH (SEQ ID NO:5).

9. The synthetic hydrogel cell culture matrix of claim 1, wherein the hydrogel comprises an 8-arm polyethylene glycol polymer, GFOGER (SEQ ID NO:1) in an amount of between about 1.5 mM and 3 mM and one or more extracellular matrix or integrin peptide binders selected from the group consisting of RGD (SEQ ID NO:14), PHSRN-K-RGD, G11RGD (SEQ ID NO:11), CMPRGD (SEQ. ID NO: 12) or GFOGDR (SEQ ID NO:16) covalently linked via vinyl sulfone moieties in the polyethylene glycol polymer.

10. The synthetic hydrogel of claim 9, comprising PEG-20 and PEG-40.

11. The synthetic hydrogel cell culture matrix of claim 9, further comprising cross linkers, wherein the one or more cross linkers comprise a protease-, proteinase-, or transpeptidase-cleavable motif.

12. The synthetic hydrogel cell culture matrix of claim 11, wherein the one or more cross linkers are cleavable by a matrix-metalloproteinase (MMP) or a Sortase A transpeptidase.

13. The synthetic hydrogel cell culture matrix of claim 1, further comprising one or more inhibitors of dissociation-induced apoptosis.

14. The synthetic hydrogel cell culture matrix of claim 13, wherein the one or more inhibitors comprise protein kinase inhibitors.

15. The synthetic hydrogel cell culture matrix of claim 13, further comprising cells, tissues, organs, or combinations thereof.

16. The synthetic hydrogel of claim 1 comprising one or more inhibitors of apoptosis.

17. A method of forming a synthetic polymeric hydrogel cell culture matrix of claim 1 comprising (i) combining a plurality of branched synthetic polymers and binders comprising both the amino acid sequence GFOGER (SEQ ID NO:1) and one or more extracellular matrix or integrin peptide binders to form an adduct, wherein the branched synthetic polymers comprise a first linking moiety and the binders comprise a second linking moiety, wherein the binders are bound via vinyl sulfone linkages to the branched synthetic polymers in a nominal amount of between at least about 1.5 mM and 5 mM of synthetic hydrogel cell culture matrix at the time of crosslinking.

18. The method of claim 17, further comprising (ii) combining the adduct of step (i) and one or more crosslinkers, wherein the crosslinkers comprise a crosslinking moiety.

19. The method of claim 18, wherein the second crosslinking moiety is a thiol group.

20. The method of claim 18, wherein each cross linker has two cross linking moieties at each terminus, wherein the crosslinking moiety is a thiol group.

21. The method of claim 18, wherein the ratio of crosslinking moiety to first linking moiety is between 0.1 and 1.

22. The method of claim 21, wherein the ratio of crosslinking moiety to first linking moiety is between 0.35 and 1.

23. The method of claim 22, wherein the ratio of crosslinking moiety to first linking moiety is about 0.5.

24. The method of claim 17, further comprising step (ia) combining cells, one or more inhibitors of apoptosis, and the adduct of step (i).

25. The method of claim 17, wherein the first linking moiety of the branched synthetic polymers is a vinyl sulfone group.

26. The method of claim 17, wherein the branched synthetic polymers are at a concentration between about 2% and about 10% (weight/volume).

27. The method of claim 26, wherein the synthetic polymers are at a concentration between about 2% and about 6% (weight/volume).

28. The method of claim 17, wherein the GFOGER (SEQ ID NO:1) binders have a concentration between about 1.5 mM and about 3 mM.

29. The method of claim 28, wherein the one or more extracellular matrix or integrin peptide binders have a concentration between about 0.1 mM and about 3.5 mM.

30. The method of claim 17, wherein the binders comprise adhesion ligands at a concentration between 0.25 mM and about 3 mM, or extracellular protein-binding peptides at a concentration between about 0.25 mM and 1 mM.

* * * * *

SEQUENCE LISTING

```
<160> NUMBER OF SEQ ID NOS: 35

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X is hydroxyproline

<400> SEQUENCE: 1

Gly Phe Xaa Gly Glu Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Pro His Ser Arg Asn
1               5

<210> SEQ ID NO 3
<211> LENGTH: 4
```

```
<212> TYPE: PRT
<213> ORGANISM: Artificial Sequence
<220> FEATURE:
<223> OTHER INFORMATION: Synthetic Peptide

<400> SEQUENCE: 3

Gly Cys Arg Gly
1

<210> SEQ ID NO 4
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 4

Gly Cys Arg Glu Ile Ser Ala Phe Leu Gly Ile Pro Phe Ala Glu Pro
1               5                   10                  15

Pro Met Gly Pro Arg Arg Phe Leu Pro Pro Glu Pro Lys Lys Pro
            20                  25                  30

<210> SEQ ID NO 5
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 5

Gly Cys Arg Glu Thr Leu Gln Pro Val Tyr Glu Tyr Met Val Gly Val
1               5                   10                  15

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X is any one of the natural amino acids, but
      preferably arginine (Arg, R)

<400> SEQUENCE: 6

Leu Pro Xaa Thr Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X is any one of the natural amino acids, but
      preferably arginine (Arg, R)

<400> SEQUENCE: 7

Leu Pro Xaa Ser Gly
1               5

<210> SEQ ID NO 8
<211> LENGTH: 5
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X is any one of the natural amino acids, but
      preferably arginine (Arg, R)

<400> SEQUENCE: 8

Leu Ala Xaa Thr Gly
1               5

<210> SEQ ID NO 9
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 9

Gly Cys Arg Asp Gly Pro Gln Gly Ile Ala Gly Gln Asp Arg Cys Gly
1               5                   10                  15

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X is hydroxyproline

<400> SEQUENCE: 10

Gly Phe Xaa Gly Asp Arg
1               5

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 11

Gly Cys Arg Glu Gly Gly Gly Gly Gly Gly Gly Gly Gly Gly Gly Arg
1               5                   10                  15

Gly Asp Ser Pro
            20

<210> SEQ ID NO 12
<211> LENGTH: 35
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is hydroxyproline
<220> FEATURE:
<221> NAME/KEY: Xaa
<222> LOCATION: (8)..(8)
<223> OTHER INFORMATION: Xaa is hydroxyproline
<220> FEATURE:
<221> NAME/KEY: Xaa
<222> LOCATION: (11)..(11)
<223> OTHER INFORMATION: X iis hydroxyproline
```

```
<220> FEATURE:
<221> NAME/KEY: Xaa
<222> LOCATION: (14)..(14)
<223> OTHER INFORMATION: Xaa is hydroxyproline
<220> FEATURE:
<221> NAME/KEY: Xaa
<222> LOCATION: (17)..(17)
<223> OTHER INFORMATION: Xaa is hydroxyproline
<220> FEATURE:
<221> NAME/KEY: Xaa
<222> LOCATION: (20)..(20)
<223> OTHER INFORMATION: Xaa is hydroxyproline
<220> FEATURE:
<221> NAME/KEY: Xaa
<222> LOCATION: (23)..(23)
<223> OTHER INFORMATION: X is hydroxyproline
<220> FEATURE:
<221> NAME/KEY: Xaa
<222> LOCATION: (26)..(26)
<223> OTHER INFORMATION: X iis hydroxyproline
<220> FEATURE:
<221> NAME/KEY: Xaa
<222> LOCATION: (29)..(29)
<223> OTHER INFORMATION: Xaa is hydroxyproline

<400> SEQUENCE: 12

Cys Gly Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Arg Gly
            20                  25                  30

Asp Ser Pro
        35

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Gly Cys Arg Glu Arg Asp Gly Ser Pro
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Gly Cys Arg Glu Arg Gly Asp Ser Pro
1               5

<210> SEQ ID NO 15
<211> LENGTH: 47
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (26)..(26)
<223> OTHER INFORMATION: Xaa is hydroxyproline

<400> SEQUENCE: 15

Gly Gly Tyr Gly Gly Gly Pro Gly Gly Pro Pro Gly Pro Pro Gly Pro
1               5                   10                  15
```

```
Pro Gly Pro Pro Gly Pro Pro Gly Phe Xaa Gly Glu Arg Gly Pro Pro
            20                  25                  30

Gly Pro Pro Gly Pro Pro Gly Pro Pro Gly Pro Pro Gly Pro Cys
        35                  40                  45

<210> SEQ ID NO 16
<211> LENGTH: 47
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (26)..(26)
<223> OTHER INFORMATION: Xaa is hydroxyproline

<400> SEQUENCE: 16

Gly Gly Tyr Gly Gly Gly Pro Gly Gly Pro Gly Pro Pro Gly Pro
1               5                   10                  15

Pro Gly Pro Pro Gly Pro Pro Gly Phe Xaa Gly Asp Arg Gly Pro Pro
            20                  25                  30

Gly Pro Pro Gly Pro Pro Gly Pro Pro Gly Pro Pro Gly Pro Cys
        35                  40                  45

<210> SEQ ID NO 17
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 17

Gly Cys Arg Gly Pro Pro Phe Leu Met Leu Leu Lys Gly Ser Thr Arg
1               5                   10                  15

<210> SEQ ID NO 18
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 18

Val Pro Gln Ile His Gly Gln Asn Lys Gly Asn Gln Ser Phe Glu Glu
1               5                   10                  15

Asp Thr Glu

<210> SEQ ID NO 19
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 19

Val Pro Gln Ile Gln Gly Gln Asn Lys Gly Asn Gln Ser Phe Glu Glu
1               5                   10                  15

Asp Thr Glu

<210> SEQ ID NO 20
<211> LENGTH: 19
<212> TYPE: PRT
<213> ORGANISM: Artificial Sequence
<220> FEATURE:
<223> OTHER INFORMATION: Synthetic Peptide
```

<400> SEQUENCE: 20

Val Pro Gln Ile His Gly Gln Asn Asn Gly Asn Gln Ser Phe Glu Glu
1               5                   10                  15

Asp Thr Glu

<210> SEQ ID NO 21
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 21

Val Pro Gln Ile Gln Gly Gln Asn Asn Gly Asn Gln Ser Phe Glu Glu
1               5                   10                  15

Asp Thr Glu

<210> SEQ ID NO 22
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 22

Val Pro Gln Ile His Gly Gln Asn Ile Gly Asn Gln Ser Phe Glu Glu
1               5                   10                  15

Asp Thr Glu

<210> SEQ ID NO 23
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 23

Val Pro Gln Ile Gln Gly Gln Asn Ile Gly Asn Gln Ser Phe Glu Glu
1               5                   10                  15

Asp Thr Glu

<210> SEQ ID NO 24
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 24

Val Pro Gln Ile Ala Gly Gln Asn Lys Gly Asn Gln Ser Phe Glu Glu
1               5                   10                  15

Asp Thr Glu

<210> SEQ ID NO 25
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 25

Val Pro Gln Ile Ala Gly Gln Asn Ala Gly Asn Gln Ser Phe Glu Glu

```
1               5                  10                 15
Asp Thr Glu

<210> SEQ ID NO 26
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 26

Leu Pro Arg Thr Gly Gly Gly
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X is any amino acid

<400> SEQUENCE: 27

Leu Pro Xaa Thr
1

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 28

Leu Pro Glu Thr Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 29

Leu Pro Arg Thr Gly
1               5

<210> SEQ ID NO 30
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 30

Gly Cys Arg Glu Leu Pro Arg Thr Gly Gly Gly Lys
1               5                   10

<210> SEQ ID NO 31
<211> LENGTH: 16
<212> TYPE: PRT
```

```
<213> ORGANISM: Artificial Sequence
<220> FEATURE:
<223> OTHER INFORMATION: Synthetic Peptide

<400> SEQUENCE: 31

Gly Cys Arg Asp Val Pro Met Ser Met Arg Gly Gly Asp Arg Cys Gly
1               5                   10                  15

<210> SEQ ID NO 32
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 32

Gly Cys Arg Asp Leu Pro Arg Thr Gly Gly Pro Gln Gly Ile Trp Gly
1               5                   10                  15

Gln Asp Arg Cys Gly
            20

<210> SEQ ID NO 33
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 33

Gly Cys Arg Asp Leu Pro Arg Thr Gly Gly Pro Gln Gly Ile Ala Gly
1               5                   10                  15

Gln Asp Arg Cys Gly
            20

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 34

Val Pro Met Leu Lys
1               5

<210> SEQ ID NO 35
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 35

Gly Cys Arg Asp Leu Pro Arg Thr Gly Asp Arg Cys Gly
1               5                   10
```